(12) United States Patent
Zha et al.

(10) Patent No.: US 12,611,489 B2
(45) Date of Patent: Apr. 28, 2026

(54) METHODS FOR GENERATING SURFACE COATINGS VIA SELF-ASSEMBLY OF SILK FIBROIN AND SILK FIBROIN-LIKE MACROMOLECULES

(71) Applicant: RENSSELAER POLYTECHNIC INSTITUTE, Troy, NY (US)

(72) Inventors: Runye Helen Zha, Troy, NY (US); Tanner D. Fink, Troy, NY (US); Caleb Wigham, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 998 days.

(21) Appl. No.: 17/640,595

(22) PCT Filed: Sep. 8, 2020

(86) PCT No.: PCT/US2020/049683
§ 371 (c)(1),
(2) Date: Mar. 4, 2022

(87) PCT Pub. No.: WO2021/046520
PCT Pub. Date: Mar. 11, 2021

(65) Prior Publication Data
US 2022/0331493 A1 Oct. 20, 2022

Related U.S. Application Data

(60) Provisional application No. 63/074,555, filed on Sep. 4, 2020, provisional application No. 62/896,824, filed on Sep. 6, 2019.

(51) Int. Cl.
*A61L 27/54* (2006.01)
*A61L 27/34* (2006.01)
*C09D 189/00* (2006.01)

(52) U.S. Cl.
CPC .............. *A61L 27/54* (2013.01); *A61L 27/34* (2013.01); *C09D 189/00* (2013.01)

(58) Field of Classification Search
None
See application file for complete search history.

(56) References Cited

U.S. PATENT DOCUMENTS

| | | | |
|---|---|---|---|
| 6,497,893 B1 | 12/2002 | Everhart et al. | |
| 7,521,228 B2 | 4/2009 | Lewis et al. | |
| 8,666,471 B2 | 3/2014 | Rogers et al. | |
| 9,034,816 B2 * | 5/2015 | Scheibel .......... | C07K 14/43563 |
| | | | 514/1.1 |
| 9,254,333 B2 | 2/2016 | Wang et al. | |
| 9,603,243 B2 | 3/2017 | Kaplan et al. | |
| 9,623,147 B2 | 4/2017 | Kaplan et al. | |
| 9,731,052 B2 | 8/2017 | Kaplan et al. | |
| 9,771,400 B2 | 9/2017 | Kurland et al. | |
| 9,993,527 B2 | 6/2018 | Kaplan et al. | |
| 10,314,938 B2 | 6/2019 | Kaplan et al. | |
| 2004/0266992 A1 | 12/2004 | Migliaresi et al. | |
| 2009/0162439 A1 | 6/2009 | Gobin | |
| 2015/0183841 A1 | 7/2015 | Lo et al. | |
| 2015/0231311 A1 | 8/2015 | Kaplan et al. | |
| 2017/0296696 A1 * | 10/2017 | Kaplan .............. | A61L 27/3604 |
| 2019/0151505 A1 | 5/2019 | Hedhammar et al. | |

FOREIGN PATENT DOCUMENTS

| | | |
|---|---|---|
| EP | 2509994 B1 | 9/2018 |
| JP | H03123561 A | 5/1991 |
| WO | 2008083908 A1 | 7/2008 |
| WO | 2017030197 A1 | 2/2017 |

OTHER PUBLICATIONS

Zha, R. H., et al., "Universal Nanothin Silk Coatings via Controlled Spidroin Self-Assembly," Biomaterial Science, vol. 7, pp. 683-695, Jan. 29, 2019.

Nilebäck, L., et al., "Self-Assembly of Recombinant Silk as a Strategy for Chemical-Free Formation of Bioactive Coatings: A Real-Time Study," Biomacromolecules, vol. 18, pp. 846-854, 2017.

Nilebäck, L., et al., "Bioactive Silk Coatings Reduce the Adhesion of *Staphylococcus aureus* while Supporting Growth of Osteoblast-like Cells," American Chemical Society, Applied Materials & Interfaces, vol. 11, pp. 24999-25007, 2019.

Fink, T. D., et al., "Silk and silk-like supramolecular materials," Macromolecular Rapid Communications, vol. 39, pp. 1-17, 2018.

Motta, A., et al., "Regenerated silk fibroin films: Thermal and dynamic mechanical analysis, " Macromolecular Chemistry and Physics, vol. 203, pp. 1658-1665, 2002.

Kapoor, S., et al., "Silk protein-based hydrogels: Promising advanced materials for biomedical applications," Acta Biomaterialia, vol. 31, pp. 17-32, 2016.

Zhou, C., et al., "Silk fibroin: Structural implications of a remarkable amino acid sequence," Proteins: Structure, Function, and Genetics, vol. 14, pp. 119-122, 2001.

(Continued)

*Primary Examiner* — Nicole P Babson
(74) *Attorney, Agent, or Firm* — Barclay Damon LLP; Anthony P. Gangemi

(57) ABSTRACT

Coatings are disclosed that include a solvent and a silk fibroin and/or a silk fibroin-like macromolecule. These coatings are provided via self-assembly on a target surface, or co-assembly with one or more functionally active additive compounds such as organic or inorganic therapeutics. Coating growth is facilitated by the addition of effective concentrations of kosmotropic agents, such as potassium phosphate, and provide coatings that are smooth on the nanometer length scale and free of inhomogeneities. Because the method grows the coating from the surface in a non-covalent bottom-up approach, it is suitable for coating surfaces that have high curvature or complex geometry, such as porous materials or those with nano or micron-scale diameter features. These coatings can be grown on both organic and inorganic surfaces without the need for specific covalent chemistry of the surface or activation of the surface by irradiation or chemical treatment.

25 Claims, 38 Drawing Sheets

(56)                References Cited

OTHER PUBLICATIONS

Guerette, P. A., et al., "Silk properties determined by gland-specific expression of a spider fibroin gene family," Science, vol. 272, pp. 112-115, Apr. 5, 1996.

Hijirida, D. H., et al., "13C NMR of Nephila clavipes major ampullate silk gland," Biophysical Journal, vol. 71, pp. 3442-3447, Dec. 1996.

Zhou, C. Z., et al., "Fine organization of Bombyx mori fibroin heavy chain gene," Nucleic Acids Research, vol. 28, No. 12, pp. 2413-2419, 2000.

Winkler, S., et al., "Molecular biology of spider silk," Reviews in Molecular Biotechnology, vol. 74, pp. 85-93, 2000.

Andersson, M., et al., "Silk spinning in silkworms and spiders, " International Journal of Molecular Science, vol. 17, pp. 1-14, 2016.

Knight, D. P., et al., "Changes in element composition along the spinning duct in a Nephila spider," Naturwissenschaften, vol. 88, pp. 179-182, 2001.

Tillinghast, E. K., et al., "Water extraction by the major ampullate duct during silk formation in the spider, *Argiope aurantia Lucas*," Journal of Insect Physiology, vol. 30, No. 7, pp. 591-596, 1984.

Askarieh, G., et al., "Self-assembly of spider silk proteins is controlled by a pH-sensitive relay," Nature, vol. 465, pp. 236-238, May 13, 2010.

Bauer, J., et al., "Acidic residues control the dimerization of the N-terminal domain of black widow spiders' major ampullate Spidroin 1," Scientific Reports, vol. 6, pp. 1-9, Sep. 29, 2016.

Hagn, F., et al., "A conserved spider silk domain acts as a molecular switch that controls fibre assembly," Nature, vol. 465, pp. 239-242, May 13, 2010.

Scheibel, T., "Spider silks: recombinant synthesis, assembly, spinning, and engineering of synthetic proteins," vol. 3, pp. 1-10, Nov. 16, 2004.

Rammensee, S., et al., "Assembly mechanism of recombinant spider silk proteins," PNAS, vol. 105, No. 18, pp. 6590-6595, May 6, 2008.

Humenik, M., et al., "Ion and seed dependent fibril assembly of a spidroin core domain," Journal of Structural Biology, vol. 191, pp. 130-138, 2015.

Schacht, K., et al., "Controlled hydrogel formation of a recombinant spider silk protein," Biomacromolecules, vol. 12, pp. 2488-2495, 2011.

Danner, E. W., et al., "Adhesion of mussel foot protein Mefp-5 to mica: an underwater superglue," Biochemistry, vol. 51, No. 33, pp. 1-20, Aug. 21, 2012.

Lee, H., et al., "Single-molecule mechanics of mussel adhesion," PNAS, vol. 103, pp. 12999-13003, Aug. 29, 2006.

Hong, S., et al., "Non-covalent self-assembly and covalent polymerization co-contribute to polydopamine formation," Advanced Functional Materials, vol. 22, pp. 4711-4717, 2012.

Hwang, D. S., et al., "Three intrinsically unstructured mussel adhesive proteins, mfp-1, mfp-2, and mfp-3: Analysis by circular dichroism," The Protein Society, vol. 21, pp. 1689-1695, 2012.

Wang, X., et al., "Adsorption of intrinsically disordered barnacle adhesive proteins on silica surface," Applied Surface Science, vol. 427, pp. 942-949, 2018.

Barlow, D. E., et al., "Characterization of the adhesive plaque of the barnacle balanus amphitrite: Amyloid-like hanofibrils are a major component," American Chemical Society, Langmuir Article, vol. 26, No. 9, pp. 6549-6556, 2010.

Petrone, L., et al., "Mussel adhesion is dictated by time-regulated secretion and molecular conformation of mussel adhesive proteins," Nature Communications, vol. 6, pp. 1-12, Oct. 28, 2015.

Wilker, J. J., "The iron-fortified adhesive system of marine mussels," Biological Materials Chemistry, Angewandte Chemical International Edition, vol. 49, pp. 8076-8078, 2010.

Doraiswamy, A., et al., "Matrix-assisted pulsed-laser evaporation of DOPA-modified poly(ethylene glycol) thin films," Journal of Adhesion Science and Technology, vol. 21, No. 3-4, pp. 287-299, 2007.

Goli, K. K., et al., "Formation and antifouling properties of amphiphilic coatings on polypropylene fibers," Biomacromolecules, vol. 13, pp. 3769-3779, 2012.

Wu, Z., et al., "Simple multipurpose surface functionalization by phase transited protein adhesion," Advanced Materials Interfaces, vol. 2, 1400401-11, 2015.

Rabe, M., et al., "Understanding protein adsorption phenomena at solid surfaces," Advances in Colloid and Interface Science, vol. 162, pp. 87-106, 2011.

International Search Report and The Written Opinion of the International Searching Authority, International Application No. PCT/US2020/049683, mailed Jan. 27, 2021.

* cited by examiner

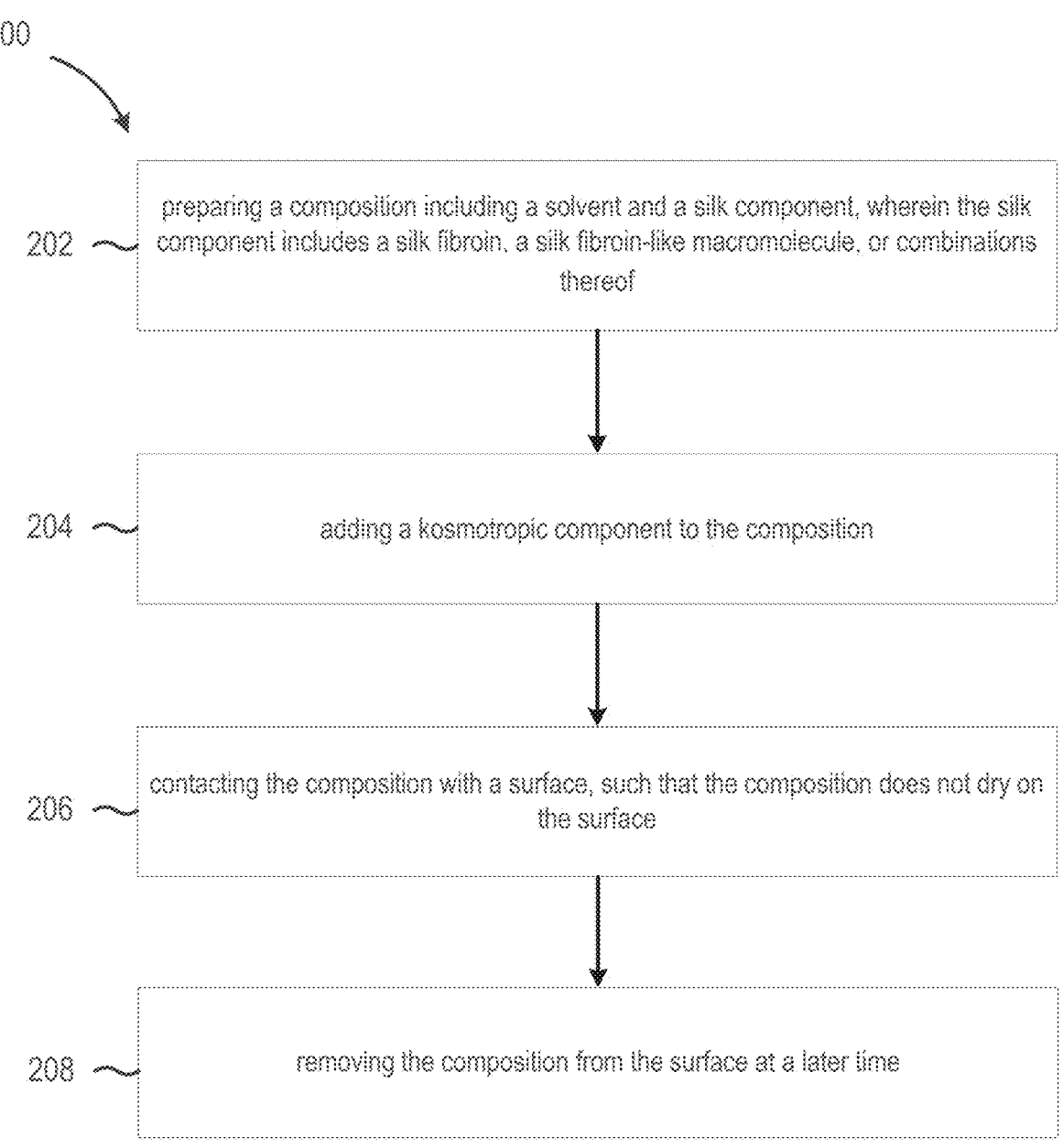

200

202 preparing a composition including a solvent and a silk component, wherein the silk component includes a silk fibroin, a silk fibroin-like macromolecule, or combinations thereof 204 adding a kosmotropic component to the composition 206 contacting the composition with a surface, such that the composition does not dry on the surface 208 removing the composition from the surface at a later time

FIG. 2A

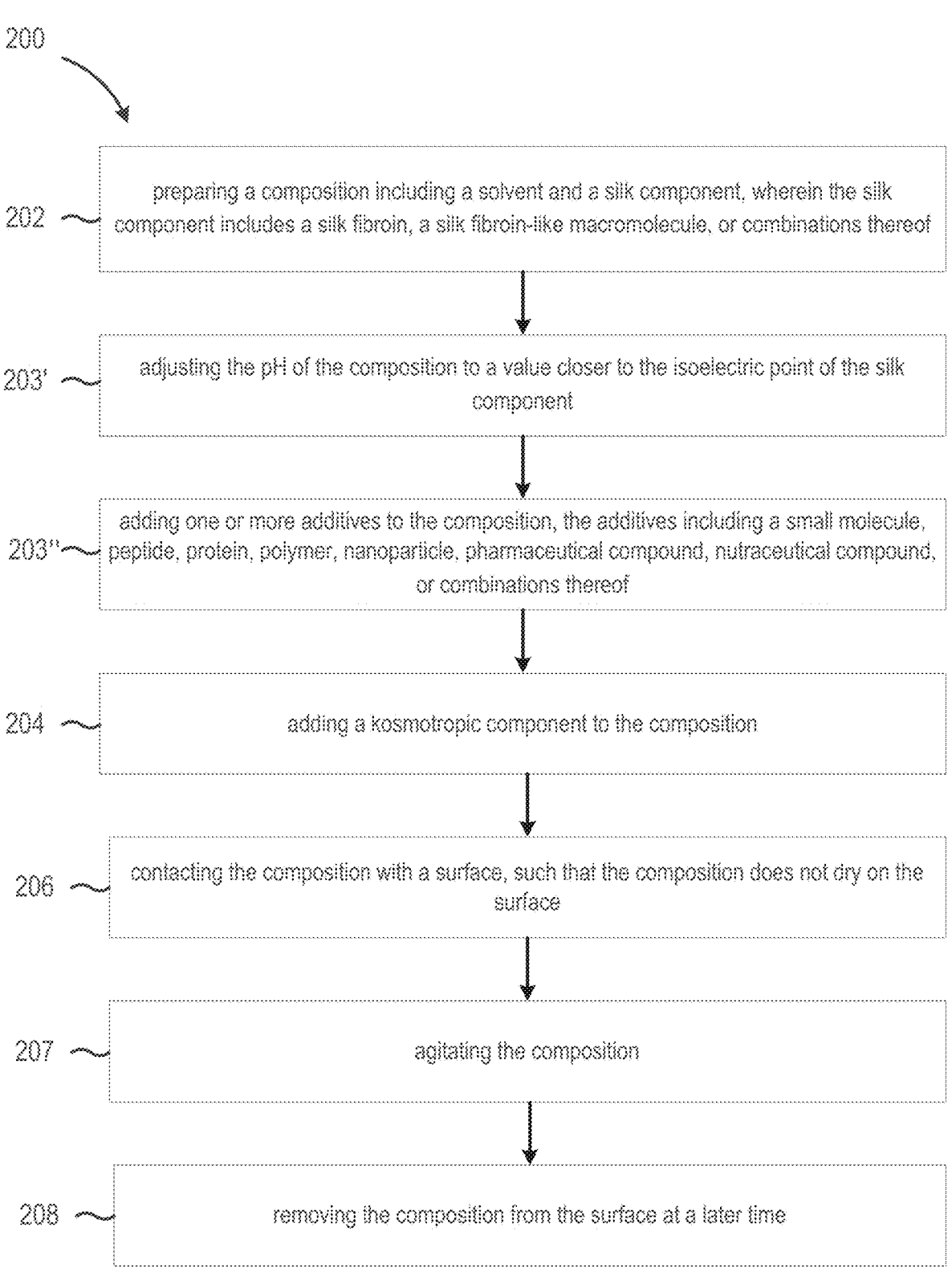

200

202 — preparing a composition including a solvent and a silk component, wherein the silk component includes a silk fibroin, a silk fibroin-like macromolecule, or combinations thereof 203' — adjusting the pH of the composition to a value closer to the isoelectric point of the silk component 203'' — adding one or more additives to the composition, the additives including a small molecule, peptide, protein, polymer, nanoparticle, pharmaceutical compound, nutraceutical compound, or combinations thereof 204 — adding a kosmotropic component to the composition 206 — contacting the composition with a surface, such that the composition does not dry on the surface 207 — agitating the composition 208 — removing the composition from the surface at a later time

FIG. 2B

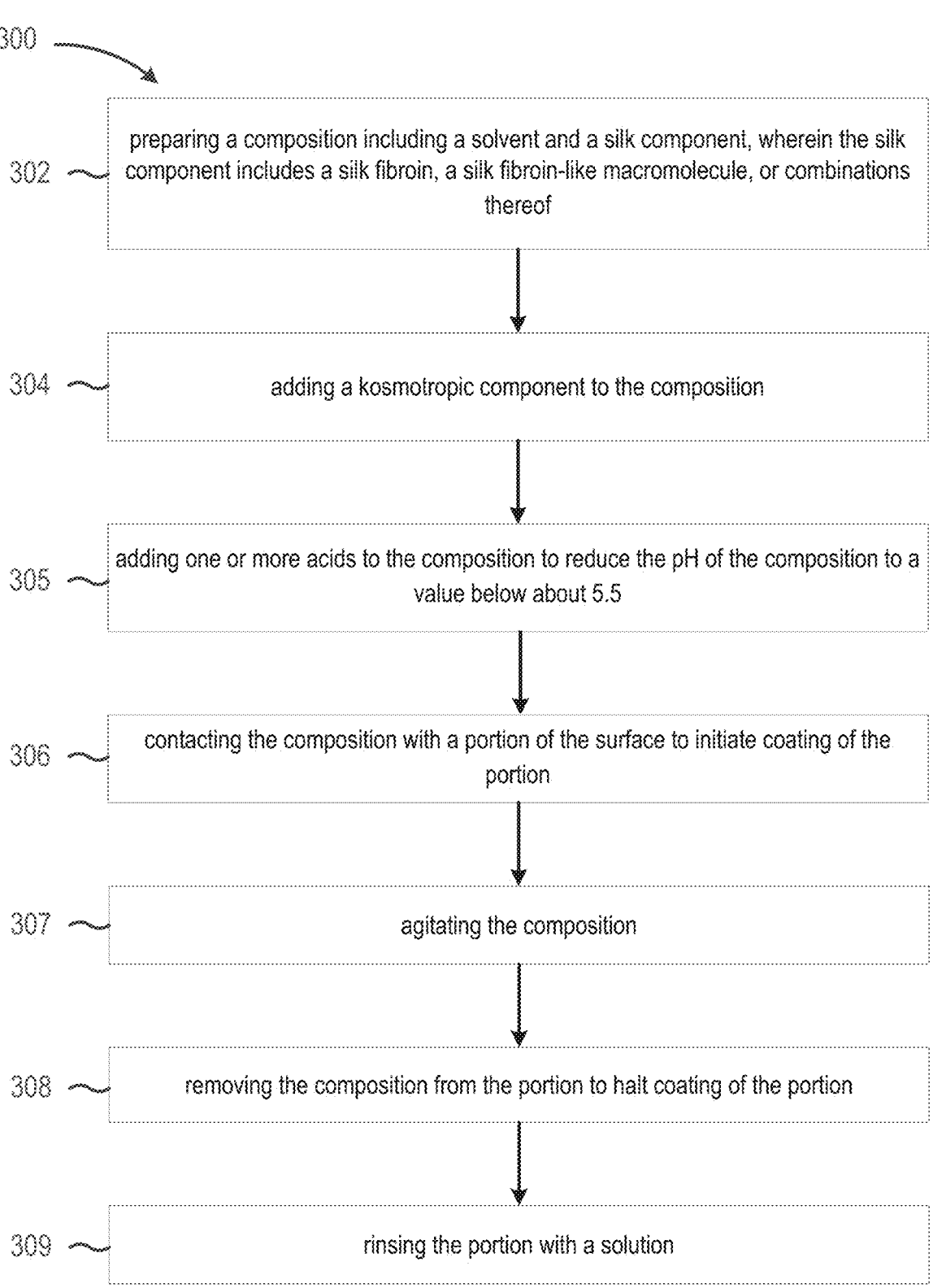

300

302 — preparing a composition including a solvent and a silk component, wherein the silk component includes a silk fibroin, a silk fibroin-like macromolecule, or combinations thereof 304 — adding a kosmotropic component to the composition 305 — adding one or more acids to the composition to reduce the pH of the composition to a value below about 5.5

306 — contacting the composition with a portion of the surface to initiate coating of the portion 307 — agitating the composition 308 — removing the composition from the portion to halt coating of the portion 309 — rinsing the portion with a solution

| Sample | β-sheet | α-helix | Random Coil | β-turn | Other |
|---|---|---|---|---|---|
| 24hr SF | 31.5±1.2 | 23.4±1.7 | 8.0±3.3 | 36.1±2.4 | 0.9±0.7 |
| 24hr SF ETOH | 38.2±1.5 | 23.2±0.1 | 6.4±0.4 | 29.3±0.4 | 2.9±0.8 |

| Material | IEP Uncoated | IEP Coated |
|---|---|---|
| TiO2 | 4.27 | 4.32 |
| Glass | 5.75 | 3.14 |
| PLLA | 2.96 | 3.94 |
| PTFE | <2.00 | 3.69 |
| PDMS | <2.00 | 3.90 |
| HDPE | <2.00 | 3.32 |

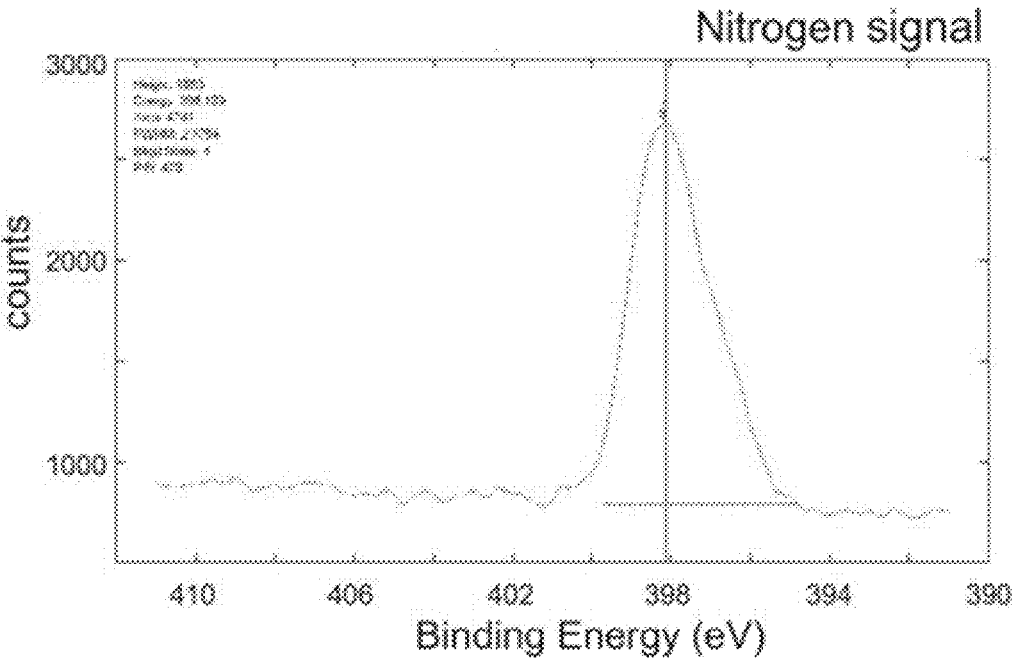
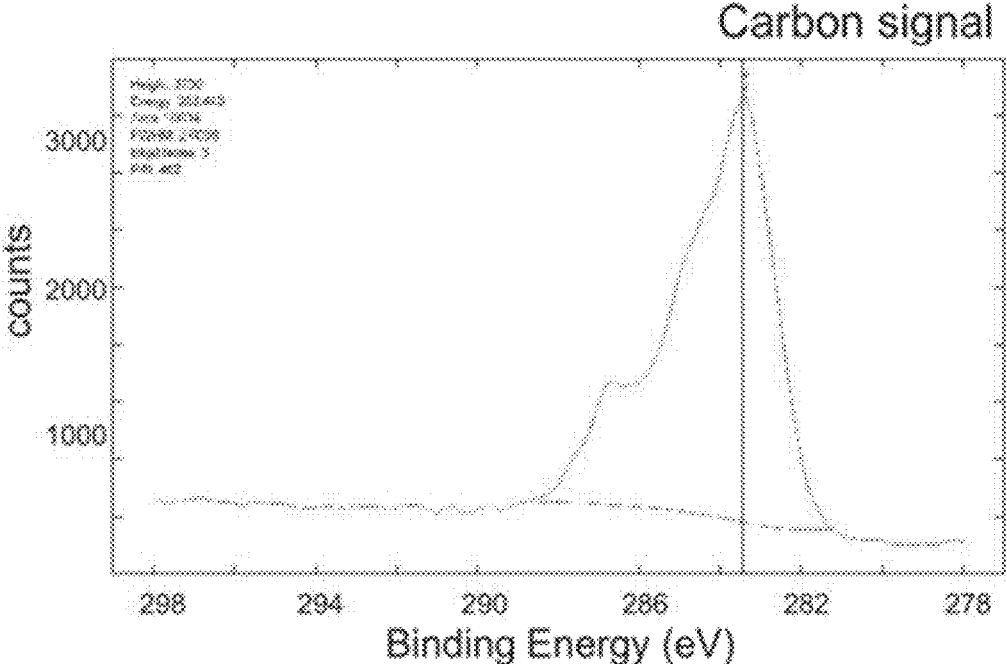
FIG. 17A

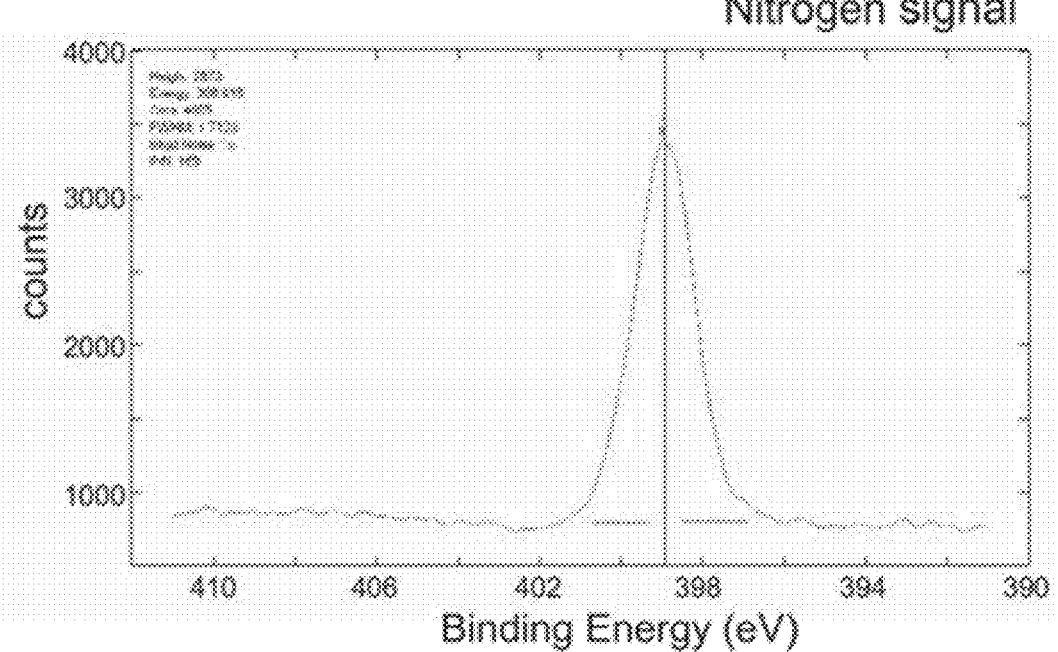
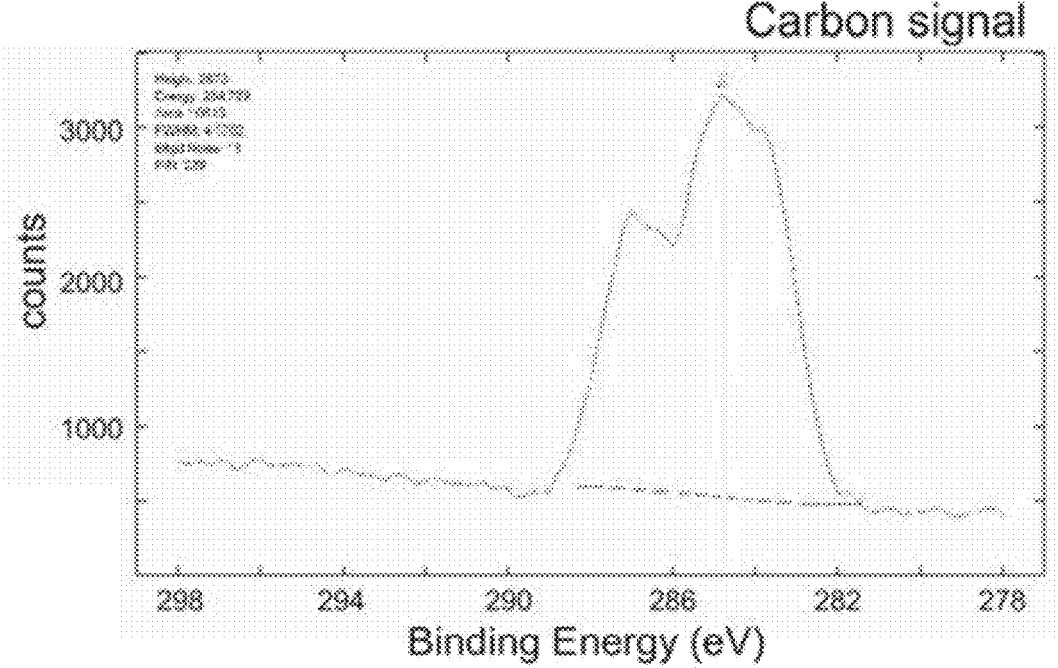
FIG. 17B

METHODS FOR GENERATING SURFACE COATINGS VIA SELF-ASSEMBLY OF SILK FIBROIN AND SILK FIBROIN-LIKE MACROMOLECULES

CROSS REFERENCE TO RELATED APPLICATION(S)

This application is a national stage patent application filing of International Application No. PCT/2020/049683, filed Sep. 8, 2020, which claims the benefit of U.S. Provisional Application Nos. 62/896,824, filed Sep. 6, 2019, and 63/074,555, filed Sep. 4, 2020, which are incorporated by reference as if disclosed herein in their entireties.

BACKGROUND

For many applications in healthcare and sustainability, such as catalysis, separations, drug delivery, biosensing, and regenerative medicine, the surface properties of a material are critical for performance. Numerous top-down and bottom-up methods for surface modification have been developed, encompassing both covalent and non-covalent approaches. However, covalent methods, such as "grafting from/to," utilize specific surface chemistries and often utilize reagents or solvents that are incompatible with biological components. Significant effort in developing appropriate chemistries is used for each system, with notable difficulties in achieving high grafting density and derivatizing chemically inert surfaces. Alternatively, non-covalent approaches such as dip or spin coating can be applied to a variety of surface chemistries, but non-planar substrates or fine topographical features pose problems, while the use of organic solvents further limits application scope. Ultimately, the challenges faced in surface modification severely limit the fabrication of materials with complex multi-component surface activity.

Few truly universal strategies that can modify a wide range of surfaces, regardless of chemistry or geometry, with dense and stable macromolecular coatings have been demonstrated. One such strategy is to use oxidative polymerization of dopamine, a molecule that mimics the adhesion motifs in mussels, to generate polydopamine coatings with nanoscale thickness on substrates ranging from $TiO_2$ to Teflon. Plant-derived polyphenols, such as tannic acid and pyrogallol, can demonstrate similar coating behavior. These coatings can increase surface wettability and allow further grafting from the surface. However, polyphenol and polydopamine coatings provide undesirable cell-surface interactions for certain biomedical applications, are readily fouled by serum proteins, and are often plagued by strongly adhered particulates from solution-phase aggregation.

More recently, non-specific protein adsorption has been explored as a potential non-covalent substrate-tolerant method for modifying surfaces. Decoration of polypropylene surfaces with fibrinogen and lysozyme acting as a "grafting from" polymerization initiator has been demonstrated. However, these adsorbed proteins did not provide complete surface coverage and required covalent crosslinking by glutaraldehyde, a toxic chemical reagent, for stability. Similar work showed that β-sheet-rich fibrils formed by lysozyme can adhere to a variety of surfaces, including glass, gold, quartz, silicon, and polytetrafluoroethylene, and present biotin for further conjugation to streptavidin-bearing components. However, this adsorbed protein layer also suffered from patchy, incomplete surface coverage.

"Layer-by-layer" is another method that has been developed for generating coatings on surfaces without the use of covalent chemistry. This method typically dips a substrate repeatedly in solutions containing macromolecules of opposing charges to deposit a coating which grows in thickness with the number of dipping cycles. Layer-by-layer can be used to coat surfaces with a variety of chemistries and geometries and can also be loaded with functionally active molecules, such as organic or inorganic therapeutics, during the coating process. However, layer-by-layer coating processes use hundreds of dipping cycles to create robust coatings that have sufficient retention of the loaded molecules. Thus, layer-by-layer methods are labor-intensive, costly, and can suffer from batch-to-batch variability.

Silk fibroins are structure-bearing proteins found naturally in the core of silk threads spun by insects and arachnids. Silk fibroin materials can resist dissolution in most organic solvents, withstand temperatures up to 285° C. without melting, and exhibit suitable properties for drug delivery and tissue engineering applications. Though the cell-material interactions of silk fibroins vary with protein sequence, they generally exhibit low cytotoxicity and elicit lower inflammatory response than common biomedical materials such as collagen and polylactic acid. Studies have shown that silk fibroin derived from *Bombyx mori* cocoon threads causes minimal thrombogenicity, foreign body response, inflammation, and fibrosis when implanted. Thus, coatings comprised of silk fibroin can potentially be used to improve the surface biocompatibility and bioactivity of materials and devices used in biomedical applications, such as implants, diagnostic devices, sensors, drug delivery devices and materials, and scaffolds for regenerating tissue.

Coatings of silk-like polypeptides have been generated in which a liquid solution including the silk-like polypeptide is applied to a substrate, including chemically inert materials, by dip coating or spray coating. Dip coating refers to immersing the substrate into a liquid coating solution, e.g., for up to 10 minutes, removing the substrate from the liquid, allowing the liquid to drain from the substrate, and then drying the substrate. Spray coating refers to exposing the substrate to an aerosol of the liquid coating solution, followed by drying of the material. These methods can create coatings with thickness from several nanometers to tens of micrometers. However, these methods offer poor control of coating thickness and furthermore cannot easily yield homogeneous coatings on objects with complex geometries or surfaces with fine topographical features, such as patterned surfaces, porous materials, or fibrous materials.

Coatings of silk fibroin have also been generated by chemically grafting a titanium-binding peptide onto silk fibroin derived from *Bombyx mori* cocoons. Titanium surfaces exposed to a liquid solution containing this chemically altered silk fibroin for 1 hour can be coated by a thin layer of the altered silk fibroin. However, this method does not provide a way to control coating thickness or create coatings thicker than one monolayer of protein.

A modified layer-by-layer method for generating coatings of silk fibroin derived from *Bombyx mori* cocoons has been disclosed. This method entails dipping substrates in a liquid solution including the silk fibroin for 2 minutes, removing the material and washing it with water or a mixture of methanol and water, drying the material, then repeating the dip-wash-dry cycle as needed to build up a coating. This method can generate coatings tens of nanometers thick. Similarly, a modified layer-by-layer method has been disclosed for generating films of natural and recombinant spider silk proteins using solutions including spider silk proteins dissolved in formic acid to be cast on a substrate, followed by evaporating the formic acid solvent, and subsequently repeating the casting and drying steps to create a thick multilayer film. These layer-by-layer methods for fabricating silk films and coatings suffer from the same issues as other layer-by-layer methods, such as being highly labor-intensive.

Another method for functionalizing surfaces with recombinant silk fibroin-like protein has been described where the protein is allowed to adsorb by non-specific interactions onto surfaces. This method can modify the properties of a variety of surfaces, though it is not known if complete surface coverage by the protein can be achieved, fine control over coating thickness was not reported, and no additive agents were used to control coating formation.

Despite these advances in methods to produce coatings of silk fibroin and silk fibroin-like macromolecules, there is still a technological need for methods that can generate coatings that are tenacious, provide complete surface coverage, have physicochemical properties such as thickness that are easily tunable, and are able to be loaded with diverse therapeutic molecules for sustained delivery over time. Furthermore, it is advantageous, particularly in biomedical applications, for these coating methods to be efficacious on chemically inert substrates, use solvents and reagents that do not cause inactivation of biologically active components, and accommodate substrates that are geometrically and/or topographically complex.

Without wishing to be bound by theory, silk fibroins are distinguishable from non-fibroin silk proteins and can be classified as fibrillar or network-forming proteins. Though primary sequence differs amongst silk fibroins from various species and silk thread types, a linear architecture comprised of non-repetitive N-terminus and C-terminus domains and a highly repetitive core domain is generally observed. The repetitive core domain, which accounts for the majority of the protein sequence (see FIG. 1A), includes regularly alternating hydrophobic-hydrophilic peptide segments and is predominantly disordered while stored in the spinning gland, though some α-helical secondary structures may exist. Importantly, the hydrophobic segments assemble into β-sheets that stack into rigid inter-chain nanocrystals during the spinning process. In contrast, the hydrophilic segments form an amorphous matrix surrounding the nanocrystals (see FIG. 1B). Consequently, silk materials are elastomers with β-sheet nanocrystals acting as supramolecular crosslinks. In the natural spinning process, silk proteins solubilized in an aqueous spinning dope undergo self-assembly to form these elastomers in response to kosmotropic factors, including an influx of phosphate anions. Recombinant silk fibroins, which are not derived from nature but are synthesized according to man-made genes by genetically engineered organisms, and other silk fibroin-like macromolecules, which may be synthesized abiotically using techniques common to polymer or organic chemistry, often mimic the sequence of the repetitive core domain with varying degrees of homology.

The transition of silk fibroins from a soluble protein to a robust β-sheet-rich material is a complex supramolecular assembly phenomenon. In natural silk spinning, changes in pH, ion composition, and hydration occur as the spinning dope passes through the spinning duct. For example, a pH gradient of 7 to 6.5 from the posterior to the anterior silk gland has been found in Bombyx mori silkworm larvae and in several spider species. Increasing phosphate ion and decreasing sodium chloride levels have been observed along the major ampullate spinning ducts of spiders, while microvilli lining the lumen of the anterior silk gland are thought to absorb water molecules from the dope. The overall effect of these factors is to promote rapid supramolecular aggregation and β-sheet assembly.

SUMMARY

Some embodiments of the present disclosure are directed to a method of providing a coating to a surface, the method comprising preparing a composition including a solvent and a silk component, wherein the silk component includes a silk fibroin, a silk fibroin-like macromolecule, or combinations thereof; adding a kosmotropic component to the composition; and contacting the composition with a portion of the surface, such that the composition does not dry on the surface, to initiate the coating process. In some embodiments, the method includes adjusting the pH of the composition to a value closer to the isoelectric point of the silk component. In some embodiments, the pH of the composition is between about 4 and 6. In some embodiments, the pH of the composition is below about 5.5. In some embodiments, the method includes adding one or more acids to the composition to reduce the pH of the composition to a value below about 5.5.

In some embodiments, the method includes adding one or more additives to the composition, the additives including a small molecule, peptide, protein, polymer, nanoparticle, pharmaceutical compound, nutraceutical compound, or combinations thereof. In some embodiments, the additives are provided in the composition at a concentration of less than about 30% by weight of the silk component. In some embodiments, the kosmotropic component is added to the composition after adding the one or more additives.

In some embodiments, the silk component includes silk fibroin derived from the cocoons of Bombyx mori silkworks, recombinantly produced silk fibroin, or combinations thereof. In some embodiments, the kosmotropic component includes phosphate, hydrogen phosphate, dihydrogen phosphate, $KH_2PO_4$, $K_2HPO_4$, or combinations thereof. In some embodiments, the concentration of silk component in the composition is about 0.1 mg/mL to about 2 mg/mL. In some embodiments, the concentration of silk component is about 0.5 mg/ml. In some embodiments, the concentration of kosmotropic component in the composition is between about 150 mM and about 300 mM. In some embodiments, the concentration of kosmotropic component is about 200 mM.

Some embodiments of the present disclosure are directed to a method of generating a surface coating on a surface, the method comprising preparing a composition including a solvent and a silk component, wherein the silk component includes a silk fibroin, a silk fibroin-like macromolecule, or combinations thereof; adding a kosmotropic component to the composition; contacting the composition with a portion of the surface to initiate coating of the portion; and removing the composition from the portion to halt coating of the portion. In some embodiments, contacting the composition with a portion of the surface to initiate coating of the portion includes agitating the composition. In some embodiments, removing the composition from the portion to halt coating of the portion includes rinsing the portion with a solution. In some embodiments, the temperature of the composition is between about 20° C. to about 25° C.

Some embodiments of the present disclosure are directed to an article comprising at least one surface and a coating deposited thereon, the coating being obtained by the methods described above. In some embodiments, the coating has a root mean square roughness less than about 5 nm. In some embodiments, the coating has a thickness in the dry state of less than 50 nm.

BRIEF DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings, wherein:

FIG. 2A is a chart of a method for providing a coating to a surface according to some embodiments of the present disclosure;

FIG. 2B is a chart of a method for providing a coating to a surface according to some embodiments of the present disclosure;

FIG. 3 is a chart of a method for generating a surface coating on a surface according to some embodiments of the present disclosure;

FIGS. 17A and 17B are graphs of x-ray photoelectron spectroscopy (XPS) analysis of drop-cast bulk silk fibroin coatings (FIG. 17A) and coatings according to some embodiments of the present disclosure (FIG. 17B);

DETAILED DESCRIPTION

Figure 1A:
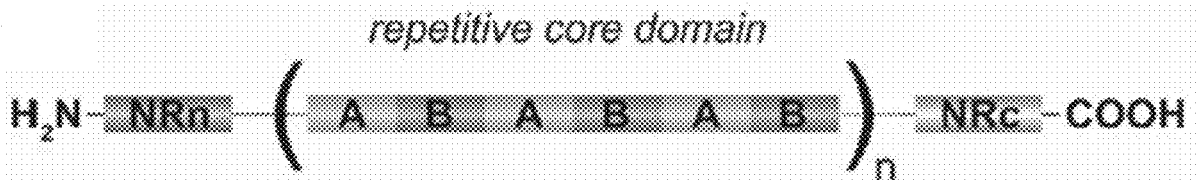
FIG. 1A is a schematic depiction of a protein primary structure for silk fibroin.
Figure 1B:
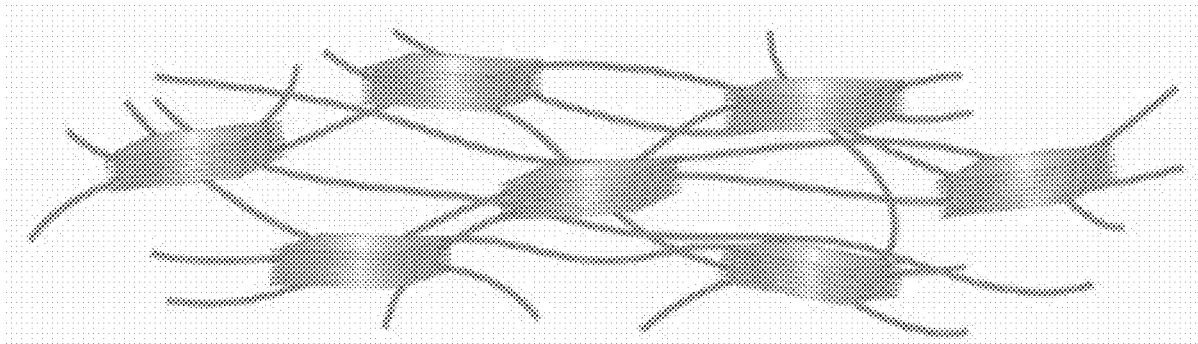
FIG. 1B is a schematic depiction of the nanoscale structure formed by silk fibroin and silk fibroin-like macromolecules, consisting of β-sheet nanocrystals in an amorphous matrix.

Referring now to FIG. 2A, some aspects of the present disclosure are directed to a method 200 of providing a coating to a surface. As used herein, the term "coating" refers to a cohesive or semi-cohesive layer of material covering at least a portion of a surface, e.g., of a substrate. In some embodiments, the coating completely covers the surface. In some embodiments, the coating is substantially free of defects, e.g., through which the surface can be detected by means of analytical techniques specific for the top layer of atoms or molecules of a surface. In some embodiments, as will be discussed in greater detail below, the coating has a thickness between about 1 nm and about 50 nm when measured in a dry state. In some embodiments, the coating is substantially free of features and adhered particulates significantly larger than the typical features of the coating. In some embodiments, the coating has a root mean square roughness less than 5 nm. As will be discussed in greater detail below, in some embodiments, the coating is sufficiently adherent and stable to resist delamination, degradation, and/or dissolution when immersed in or rinsed with flowing water for at least 30 seconds. In some embodiments, the coating is sufficiently adherent and stable to resist delamination, degradation, and/or dissolution when immersed in or rinsed with flowing water for at least 2 weeks. In some embodiments, the coating follows the topography of the surface with high fidelity on the nanometer length scale.

In some embodiments, the surface is an organic substrate, e.g., includes hydrocarbon as a principle element, an inorganic substrate, e.g., does not include hydrocarbon as the principle element, or combinations thereof. In some embodiments, the surface remains solid when exposed to aqueous solvents. In some embodiments, the surface is cleaned prior to contacting the composition provided by method 200 in this disclosure. In some embodiments, the surface includes a polymer, e.g., nylon, polypropylene, polycarbonate, polylactic acid, polyethylene, polyethylene terephthalate, polytetrafluorethylene, or combinations thereof. In some embodiments, the surface is an inorganic substrate that includes an inorganic polymer, e.g., polydimethylsiloxane, a noble metal, e.g., gold, an oxide, e.g., titanium dioxide or silicon dioxide, or combinations thereof. In some embodiments, the surface is hydrophobic, hydrophilic, or combinations thereof. In some embodiments, the surface is planar; curved; topographically complex, e.g., includes nano- or micron-scale features, such as curvature, roughness, patterns, and geometric shapes; porous, or combinations thereof. In some embodiments, the surface includes structural features that are purposefully engineered, occur naturally, are a byproduct of other processing methods unrelated to the present disclosure, or combinations thereof. As discussed in greater detail below, method 200 provides the coating to the surface using a bottom-up approach and is suitable for providing defect-free, complete coatings even to surfaces with high curvatures or complex geometries, such as tissue engineering scaffolds with arrays of fibers, nano or micron-scale diameters, porous materials, etc.

Referring again to FIG. 2A, in some embodiments, method 200 includes preparing 202 a composition including a solvent and a silk component. In some embodiments, the solvent includes a polar protic solvent or polar aprotic solvent. In some embodiments, the solvent is water.

In some embodiments, the silk component includes a silk fibroin, a silk fibroin-like macromolecule, or combinations thereof. In some embodiments, the concentration of the silk component in the composition is about 0.1 mg/mL to about 2 mg/mL. In some embodiments, the concentration of silk component is about 0.5 mg/mL. As used herein, a silk fibroin includes fibrous protein derived from materials synthesized by non-genetically engineered biological organisms in nature that is capable of forming β-sheet secondary structures. In some embodiments, the silk fibroin is substantially isolated and purified from cellular material or other macromolecular contaminants. Without wishing to be bound by theory, silk fibroin has a primary structure including segments of hydrophobic amino acids that can form β-sheet conformations alternating regularly with segments of hydrophilic amino acids that can form random coil or α-helix conformations. The β-sheets of one silk fibroin protein chain interact non-covalently with the β-sheets of one or more other protein chains. A "tandem repeat" refers to one tandem concatenation of the hydrophobic segment and hydrophilic segment. In some embodiments, the silk fibroin is a linear polypeptide with at least four tandem repeats and can form materials with at least 30% β-sheet content. In some embodiments, the silk fibroin includes a hydrophobic segment rich in alanine amino acids that forms β-sheets. In some embodiments, the silk fibroin is an approximately 100 kilodalton fragment of fibroin heavy chain.

As used herein, a silk fibroin-like macromolecule includes artificially synthesized macromolecule, such as a polypeptide, protein, or polymer, that has tandem repeats and is capable of forming β-sheet secondary structures. In some embodiments, the silk fibroin-like macromolecule is synthesized by means of abiotic chemical methods, such as organic synthesis, polymer synthesis, solid-phase peptide synthesis, solution-phase peptide synthesis, etc.; synthesized by a living organism genetically engineered to express the silk fibroin-like macromolecule, or combinations thereof. In some embodiments, the silk fibroin-like macromolecule is substantially purified and free of substantial amounts of macromolecular contaminants. In some embodiments, the silk fibroin-like macromolecule is linear with at least four tandem repeats and can form β-sheets, where the β-sheets of one macromolecule chain interact non-covalently with the β-sheets of one or more other chains.

In some embodiments, the silk component includes *Bombyx mori* silk fibroin, recombinant silk mimicking spider-derived silk fibroin, e.g., functional equivalents thereof, or combinations thereof.

Referring again to FIG. 2A, at 204, a kosmotropic component is added to the composition. Without wishing to be bound by theory, a kosmotropic agent is a molecule or atom that increases stability and structure of the interaction between water molecules. Kosmotropic agents increase the intramolecular and intermolecular interactions of silk fibroin and silk fibroin-like macromolecules, contributing to self-assembly or co-assembly of the silk component, as will be discussed in greater detail below. In some embodiments, the kosmotropic component includes phosphate, hydrogen phosphate, dihydrogen phosphate, or combinations thereof. In some embodiments, the kosmotropic component includes $KH_2PO_4$, $K_2HPO_4$, or combinations thereof. In some embodiments, the concentration of the kosmotropic component in the composition is between about 150 mM and about 300 mM. In some embodiments, the concentration of the kosmotropic component is about 200 mM.

At 206, the composition is contacted with a surface, e.g., a portion of the surface, such that the composition does not dry on the surface. In some embodiments, contacting 206 of the composition with the surface initiates growth of a coating on the surface. In some embodiments, the composition is contacted 206 with the entire surface to be coated, e.g., via immersion. In some embodiments, the composition is flowed over the surface. In some embodiments, the flowrate of composition over the surface is between about 10 μL/min and about 200 μL/min. In some embodiments, the flowrate of composition over the surface is about 100 ρL/min. In some embodiments, the composition is brought in contact with the surface in a way that does not result in significant evaporation of the solvent, which would change the concentration of components dissolved in the composition. In some embodiments, the surface is immersed in a larger volume of composition to begin the coating growth process and is removed from the composition and rinsed to end the coating growth process, as will be discussed in greater detail below. In some embodiments, method 200 is performed at temperature ranges from about 20° C.-75° C. In some embodiments, method 200 is performed at temperature ranges from about 20° C.-25° C. In some embodiments, method 200 is performed at a temperature of about 22° C.

In some embodiments, the composition is contacted with the surface for about 1 hour. In some embodiments, the composition is contacted with the surface for least 3 hours.

At 208, the composition is removed from the surface. In some embodiments, removing 208 the composition from the surface halts the coating process. In some embodiments, the surface is rinsed with flowing water, e.g., for at least 30 seconds, or by moving the surface into another solution that significantly dilutes the composition. In some embodiments, the surface may then be stored in water or dried by air or nitrogen flow before storage in ambient conditions.

Without wishing to be bound by theory, the mechanism of coating growth underlying methods consistent with the present disclosure utilize non-specific adsorption of silk fibroin and/or silk fibroin-like macromolecules onto a surface of a substrate occurring concurrently with a balanced level of supramolecular self-assembly. Non-specific adsorption uses non-covalent attractive interactions between the macromolecule and the surface, such as hydrophobic forces, hydrogen bonding, electrostatic interactions, and Van der Waals interactions, wherein substantially irreversible attachment of the macromolecule can occur on a variety of surfaces without requiring a specific atomic or molecular composition of the surface. In typical adsorption, the coverage of the surface by macromolecules is often patchy and non-complete. The adsorbed macromolecules may readily desorb from the surface when rinsed or exposed to liquid flow. Furthermore, due to repulsive interactions between macromolecules on the surface, the amount of macromolecule adsorbed plateaus at a finite quantity, typically corresponding to a few monolayers at most, and the rate of adsorption decreases to zero, typically within hours. Previous work has shown that silk fibroin adsorption without the addition of kosmotropic agents does not naturally generate more than one monolayer of protein on a surface and the protein layer does not continue to grow in mass and thickness past that saturation point.

As discussed above, methods consistent with some embodiments of the present disclosure provide a coating to a surface via self-assembly of silk fibroin molecule and/or silk fibroin-like macromolecule from the composition, without the need for formation of covalent bonds to generate cohesion between the silk components of the composition or adhesion of the silk components of the composition to the surface. Without wishing to be bound by theory, the mechanism of coating formation utilizes self-assembly, i.e., the interaction of silk fibroin molecules, silk fibroin-like macromolecules, or combinations thereof with one or more silk fibroin molecules, silk fibroin-like macromolecules, or combinations thereof to form an entity composed of multiple silk fibroins, silk fibroin-like macromolecules, or combinations thereof, where the self-assembly is controlled by a kosmotropic component. The interactions are non-covalent, e.g., hydrophobic forces, electrostatic interactions, Van der Waals forces, hydrogen bonding, π-π interaction, and other attractive interactions that do not directly result in the formation of a covalent bond. The self-assembly occurs in bulk solution, in solution on or near the surface, or combinations thereof. In some embodiments, self-assembly of silk fibroin or silk fibroin-like macromolecules results in entities such as nanofibers, micelles, or aggregates that do not precipitate from aqueous solution to form aggregates which have at least one characteristic dimension smaller than 100 nm.

Without wishing to be bound by theory, coating growth can proceed without drying steps that remove solvent.

Coating growth begins as soon as the surface is exposed to the composition and continues until the composition is removed from the surface. The kosmotropic component and other stimuli, e.g., pH, temperature, etc. cause and control attractive interactions between silk fibroin or silk fibroin-like macromolecules during adsorption, which enables the growth of coatings that are tenacious against rinsing, provide complete surface coverage without defects, and increase in thickness and mass indefinitely as long as the surface or coated surface is in contact with the composition. These interactions arise from the formation of β-sheets and the attractive interaction of β-sheets of one silk fibroin or silk fibroin-like macromolecule chain with the β-sheets of other silk fibroin or silk fibroin-like macromolecule chains. Coating thickness can be controlled by changing, for example, the amount of exposure time to the composition, the make-up of the composition, such as concentration of the silk fibroin or silk fibroin-like macromolecule, concentration of kosmotropic component, concentration of other salts that contribute to the ionic strength of the solution, or combinations thereof.

In some embodiments, the kosmotropic component and other stimuli for self-assembly are used at a level that provides a balance between protein-protein attraction and protein-surface attraction to enable indefinite growth of coatings with complete and tenacious surface coverage as described herein. Without wishing to be bound by theory, levels of kosmotropic component or other stimuli that cause too much or too little assembly do not lead to indefinite coating growth, and instead result in minimal amounts of macromolecule adhered to the surface. In an exemplary embodiment, the composition included *Bombyx mori* silk fibroin at 0.5 mg/mL, potassium phosphate at 200 mM, a pH of 5, at a temperature of 22° C. In this exemplary embodiment, complete coverage of the surface by silk fibroin is achieved in 3 hours, with coatings reaching 19.6±1.2 nm thickness after 24 hours.

In some embodiments, coating formation also involves co-assembly, i.e., the interaction of silk fibroin or silk fibroin-like macromolecules with one or more non-silk fibroin or non-silk fibroin-like components to form an entity composed of silk fibroin and/or silk fibroin-like macromolecule and the dissimilar component. Without wishing to be bound by theory, this interaction is non-covalent, e.g., uses hydrophobic forces, electrostatic interactions, Van der Waals forces, hydrogen bonding, π-π interaction, and other attractive interactions that do not directly result in the formation of a covalent bond. The co-assembly occurs in bulk solution, in solution on or near the surface, or combinations thereof. In some embodiments, co-assembly of silk fibroin or silk fibroin-like macromolecules with the non-silk fibroin component results in entities such as nanofibers, micelles, or aggregates that do not precipitate from aqueous solution and have at least one characteristic dimension smaller than 100 nm. In some embodiments, the non-silk fibroin component includes one or more additives, e.g., a small molecule, peptide, protein, polymer, or nanoparticle with therapeutic, sensing, diagnostic, or catalytic function, as will be discussed in greater detail below. In some embodiments, methods of the present disclosure provide a coating to a surface via self-assembly and co-assembly, i.e., at least a portion of the coating is self-assembled and at least a portion of the coating is co-assembled. In some embodiments, the composition further comprises one or more components to facilitate self-assembly and/or co-assembly. In some embodiments, the composition further comprises an acid, a base, an alcohol, or combinations thereof.

Referring now to FIG. 2B, in some embodiments of method 200, at 203', the pH of the composition is adjusted to a value closer to the isoelectric point of the silk component. In some embodiments, the pH of the composition is adjusted via addition of one or more acids, bases, or combinations thereof. In some embodiments, the pH of the composition is adjusted to between about 4 and 6. In some embodiments, the pH of the composition is adjusted to be below about 5.5.

Referring again to FIG. 2B, in some embodiments, at 203", one or more additives is added to the composition. In some embodiments, the one or more additives are a non-silk fibroin or non-silk fibroin-like component with activity desirable for a specified application that is co-assembled with silk fibroin or silk fibroin-like macromolecules and integrated as part of the coating. In some embodiments, the one or more additives include small molecules, peptides, proteins, polymers, nanoparticles, pharmaceutical compounds, nutraceutical compounds, or combinations thereof. In some embodiments, the one more additives functionalize the coatings with pharmaceutical properties, such as anti-microbial, anti-inflammatory, or anti-cancer drugs; surface-altering physicochemical properties, such as polyethylene glycol or hyaluronic acid; cell-signaling activity, such as growth factors; catalytic activity, such as glucose oxidase or lysozyme; and functional properties of nanoparticles, such as carbon nanotubes, graphene sheets, metal nanoparticles, or combinations thereof. In some embodiments, the kosmotropic component is added to the composition after adding the one or more additives (at 203"). In some embodiments, the composition is centrifuged to remove large aggregates immediately prior to adding the kosmotropic component (at 204). In some embodiments, the time between adding the kosmotropic component, e.g., at 204, to the composition, and exposing the composition to the surface, e.g., at 206, is less than about 1 hour. In some embodiments, the time between adding the kosmotropic component, e.g., at 204, to the composition, and exposing the composition to the surface, e.g., at 206, is less than about 15 minutes.

In some embodiments, the additives are provided in the composition at a concentration not greater than that of the silk component. In some embodiments, the additives are provided in the composition at a concentration of less than about 30% by weight of the silk component. In some embodiments, the one or more additives elute from the coating over time. In some embodiments, the one or more additives are released from the coating over a period of at least 1 day. In some embodiments, the one or more additives are released from the coating over a period of at least 14 days. In some embodiments, the one or more additives are retained substantially indefinitely within the coating. In some embodiments, some additives are retained indefinitely within the coating, while other additives are released from the coating over time. In some embodiments, the one or more additives are dissolved into the composition prior to exposure of the composition to the surface.

Again, without wishing to be bound by theory, some embodiments of the present disclosure are directed to coatings including one or more additives that are integrated or loaded into the coating during coating growth by non-covalent attractive interactions with silk fibroin or silk fibroin-like macromolecules, such as electrostatic or hydrophobic interactions. Silk fibroin and silk fibroin-like macromolecules are amphiphilic polypeptides and can participate in a variety of non-covalent interactions; thus, their interactions with the additives depends primarily on the hydrophobicity, size, and charge of the additives. Generally, a higher concentration of the additives results in a greater quantity loaded into the coating, though some components may see a saturation in loading above a certain concentration relative to the silk fibroin concentration. In some embodiments, the one or more additives do not significantly change the nature of interactions between silk fibroin or silk fibroin-like macromolecules with the surface, or the nature of self-assembly of silk fibroin or silk fibroin-like macromolecules. As coating growth occurs, the one or more additives interacting with the silk fibroin or silk fibroin-like macromolecules become incorporated into the coating by non-covalent interactions. Physical entrapment within the coating may also occur. The quantity of the additives incorporated in the coating increases in time along with the thickness of the coating. These methods of integrating additives in a silk fibroin coating is distinct from other methods that use covalent chemistry to graft functional components onto the silk fibroin or silk fibroin-like macromolecule chain.

In some embodiments, one or more additives are released from the coating in a sustained manner over time into a surrounding media. Without wishing to be bound by theory, the rate of release is determined by the strength of interactions between the additives and the silk fibroin or silk fibroin-like macromolecules that comprise the coating, as well as the size of the additives. For example, small molecules may release rapidly from the coating, potentially with a burst-release profile, while large proteins may release over an extended period of 14 days or more. More hydrophobic proteins may have more extended release profiles due to stronger interactions with the hydrophobic domains of the silk fibroin or silk fibroin-like macromolecules. Additionally, environmental conditions that cause coating degradation may also increase release rates.

In some embodiments, the composition is agitated 207 while in contact with the surface. In some embodiments, the composition is contacted with the surface with circular shaking, e.g., at 60 RPM.

Referring now to FIG. 3, some aspects of the present disclosure are directed to a method 300 of generating a surface coating on a surface. At 302, a composition is prepared. As discussed above, in some embodiments, the composition includes a solvent and a silk component, wherein the silk component includes a silk fibroin, a silk fibroin-like macromolecule, or combinations thereof. In some embodiments, the concentration of the silk component in the composition is about 0.1 mg/mL to about 2 mg/mL. In some embodiments, the concentration of silk component is about 0.5 mg/mL. At 304, a kosmotropic component is added to the composition. As discussed above, in some embodiments, the kosmotropic component includes phosphate, hydrogen phosphate, dihydrogen phosphate, or combinations thereof. In some embodiments, the kosmotropic component includes $KH_2PO_4$, $K_2HPO_4$, or combinations thereof. In some embodiments, the concentration of the kosmotropic component in the composition is between about 150 mM and about 300 mM. In some embodiments, the concentration of the kosmotropic component is about 200 mM. At 305, one or more acids or bases are added to adjust the pH of the composition. In some embodiments, the pH of the composition is adjusted to be between about 4 and 6. In some embodiments, the pH of the composition is adjusted to be below about 5.5. In some embodiments, the temperature of the composition is between about 20° C. to about 25° C. In some embodiments, the temperature of the composition is about 22° C.

At 306, the composition is contacted with a portion of the surface to initiate coating of the portion. At 307, the composition is agitated. In some embodiments, the composition is agitated in an orbital shaker, e.g., at between about 50 RPM and about 100 RPM. In some embodiments, the composition is agitated in an orbital shaker at about 60 RPM. At 308, the composition is removed from the portion to halt coating of the portion. In some embodiments, the composition is removed, e.g., at 308, by significantly diluting the composition, e.g., with water or another solution. At 309, the portion is rinsed with a solution, e.g., to remove or substantially dilute composition in contact with the surface.

Figure 4:
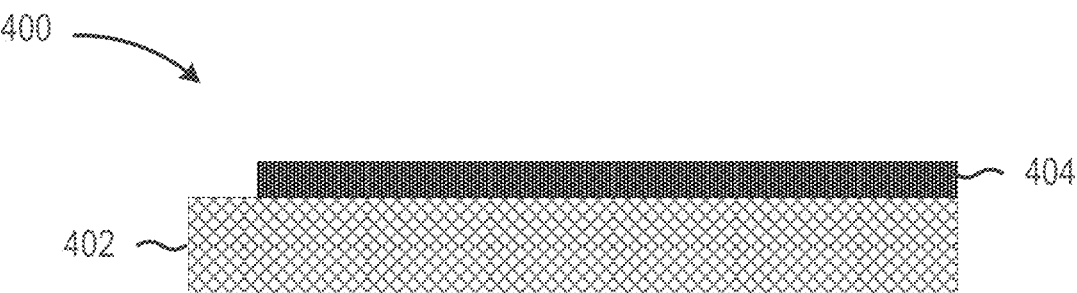
FIG. 4 is a schematic of a coating according to some embodiments of the present disclosure.

Referring now to FIG. 4, some embodiments of the present disclosure are directed to an article 400 having at least one surface 402. In some embodiments, a coating 404 is deposited on at least a portion of surface 402. In some embodiments, coating 404 is provided to surface 402 consistent with the methods discussed above. In some embodiments, coating 404 has a root mean square roughness less than about 5 nm. In some embodiments, coating 404 has a thickness between about 1 nm and about 50 nm when measured in a dry state. In some embodiments, coating 404 has a thickness greater than about 30 nm. In some embodiments, the coating has a thickness less than about 50 nm.

In some embodiments, article 400 is any structure where coating 404 and its associated advantages would confer advantageous properties thereto. In some embodiments, article 400 is an implant, diagnostic device, sensor, drug delivery device, drug delivery material, scaffold for regenerating tissue, or combinations thereof. In some embodiments, coating 404 adjusts the physicochemical properties of article 400, surface 402, or combinations thereof. In some exemplary embodiments, coating 404 adjusts the hydrophobicity of article 400, as measured by water contact angle on the article before and after coating. Without wishing to be bound by theory, the hydrophobicity of a coated surface matches that of a bulk film made from the silk fibroin or silk fibroin-like macromolecule used. Thus, extremely hydrophilic surfaces become more hydrophobic after coating, while extremely hydrophobic surfaces become more hydrophilic. In some exemplary embodiments, coatings 404 endow a surface with new chemical composition, e.g., as characterized by surface-sensitive techniques such as X-ray photoelectron spectroscopy or fluorophore labeling of chemical groups. Without wishing to be bound by theory, the chemical composition of the coating reflects the chemical composition of the silk fibroin or silk fibroin-like macromolecule used. In some embodiments, coatings 404 change the mechanical properties of article 400, surface 402, or combinations thereof, e.g., as characterized by nanoindentation. The mechanical properties of the coating depend on the material properties of the silk fibroin or silk fibroin-like macromolecule used. In an exemplary embodiment, coating is soft and hydrated in water, such as with a hydrogel material. In some embodiments, coatings 404 are effective to change the interaction of cells with the surface based on the properties of the coating. For example, coating 404 may increase the adhesion of mammalian nerve cells on surface 402, increase the bioactivity of surface 402, decrease the adhesion of bacteria on surface 402, or combinations thereof.

EXAMPLES

Materials. For the examples described herein, silk fibroin extracted from *Bombyx mori* cocoon threads was obtained commercially from Advanced BioMatrix as a 50 mg/mL aqueous solution. This *Bombyx mori* silk fibroin was degummed and had a molecular weight of approximately 100 kilodaltons. Recombinant silk fibroin, denoted eADF4 (C16), was obtained from AMSilk GmbH. As discussed above, eADF4(C16) is a 47.7 kilodalton protein that mimics the repetitive core domain of *Araneus diadematus* dragline spidroin and has 16 repeats of an amphiphilic β-sheet forming 35-amino acid sequence with an artificial N-terminal T7 tag. TiO$_2$-coated QCM-D sensors (QSX 310 Ti) were obtained from Biolin Scientific AB. TiO$_2$ substrates were obtained from University Wafers (Boston, MA) as polished Si wafers with 100 nm TiO$_2$ deposited by e-beam evaporation. Polymer and stainless substrates were obtained from McMaster-Carr (Robbinsville, NJ). Ultrapure water was obtained from a Labconco WaterPro BT benchtop water purification system, which produces water with a resistivity of >18 MΩ-cm, a conductivity of <0.056 μS/cm and <50 ppb of Total Organic Carbons. Unless otherwise noted, all reagents and solvents used were obtained from Fisher Scientific (Waltham, MA).

Experimental Section: Quartz Crystal Microbalance with Dissipation (QCM-D). QCM-D utilizes the piezoelectric properties of an AT-cut quartz crystal by applying a pulsating voltage and monitoring changes in crystal oscillation frequency and dissipation of the shear propagation wave. This technique allows simultaneous real-time monitoring of surface adsorption kinetics and film structural properties. Mass adsorption to the sensor surface decreases oscillation frequency and increases dissipation. Comparing changes in frequency and dissipation allows for determination of viscoelastic characteristics of the adsorbed layer. TiO$_2$-coated QCM-D sensors were cleaned in accordance with manufacturer specifications. Sensors were immersed in 1% Hellmanex II for 30 minutes at room temperature, rinsed with ultrapure water and dried with nitrogen gas, then sonicated in 99% ethanol for 10 minutes, rinsed with ultrapure water and dried with nitrogen gas, and finally UV-ozone treated for 10 minutes. All sensors were used immediately after UV-ozone treatment without further modification. QCM-D measurements were obtained using a Q-Sense E4 instrument. Sensors were calibrated in both air and liquid to ensure quality control. The flow rate was set to 100 μL/min and the temperature maintained at 25° C. Baseline equilibrium was obtained by flowing buffer including a mixture of KH$_2$PO$_4$ and K$_2$HPO$_4$ over the sensors until an adequate baseline was established (ΔHz <2 Hz/hr). Protein solution was then flowed through the system and frequency and dissipation changes were recorded. Mass deposited over time was then calculated from the raw data using a viscoelastic modeling package in Q-Sence Dfind software.

Thioflavin T (ThT) Assay. ThT is a benzothiazole salt commonly used to quantify the presence of β-sheet secondary structure in proteins. The binding of ThT to a β-sheet structure induces a red shift of its emission spectrum with excitation and emission signal at 450 and 482 nm, respectively. Thus, the evolution of signal at 482 nm can be used to monitor β-sheet driven protein assembly. To prepare assays, ThT and silk fibroin were mixed in an aqueous solution including a mixture of KH$_2$PO$_4$ and K$_2$HPO$_4$ that buffers the solution at pH 5 such that the final ThT concentration was 40 μM. KH$_2$PO$_4$/K$_2$HPO$_4$ was the last component added to the solution and was added immediately prior to the start of data collection. Black-wall clear-bottom 96 well plates were used to minimize fluorescent bleeding between samples. To prevent evaporation, acetate plate sealers were used, and optical probes were set to read from plate bottom to avoid potential condensation signal interference. All wells were kept at room temperature and scanned every 30 minutes over a period of 6 days. Select sample volumes were measured at the end of the experiment and to confirm that no evaporation had occurred. Data was analyzed by subtracting baseline signals of solutions without silk fibroin from the emission spectra of each sample.

Dynamic Light Scattering (DLS). DLS is an optical technique used to determine the hydrodynamic size distribution of particles suspended in solution. DLS uses a monochromatic laser passing through a sample onto a detector. Particles moving through the beam by Brownian motion cause scattering and fluctuations in intensity. These temporal fluctuations are analyzed by an autocorrelation function to determine diffusion coefficients, from which particle sizes are then calculated. Experiments were conducted using a Litesizer 500 (Anton Paar). Disposable polystyrene cuvettes were used for all samples. Temperature was maintained at 25° C. and the detector angle was set to side scatter (90°). Refractive indices of 1.45 and 1.33 were used for protein and water/phosphate buffer, respectively. All other optical settings were set to automatic and were determined by the software for best quality data collection. Ultrapure water and a mixture of $KH_2PO_4$ and $K_2HPO_4$ adjusted to buffer at various pH values were filtered using a 0.2 μm polyethersulfone syringe filter prior to analysis. All polystyrene cuvettes were blown with air filtered through 0.2 μm polyethersulfone syringe filter before sample addition. Solutions including silk fibroin and $KH_2PO_4/K_2HPO_4$ at set pH levels were added to the cuvette, capped to prevent evaporation, and allowed to equilibrate in Litersizer for 2 minutes before data acquisition.

Coating Stability Studies. Stability studies were performed to evaluate the tenacity and resistance to desorption of silk fibroin coatings in aqueous and organic solvents. To prepare samples, $TiO_2$ substrates (1 cm²) were cleaned and coated for 24 hours according to one exemplary embodiment of the present disclosure, which immerses the substrate in a composition including 0.5 mg/mL *Bombyx mori* silk fibroin and 200 mM phosphate ions, provided by a mixture of $KH_2PO_4$ and $K_2HPO_4$ that buffers the solution at pH 5. Substrates were kept at 25° C. and agitated at 60 RPM using an orbital shaker during the coating time. Coated substrates were then gently washed with ultrapure water and dried with air. Initial coating thickness was measured using spectroscopic ellipsometry. Coated substrates were then placed in a small petri dish or glass vial filled with 5 mL solvent, capped, and stored in ambient conditions or set in an orbital shaker at 60 RPM agitation at 25° C. or 37° C. At each time point, coated substrates were removed from the solvent, gently submerged in ultrapure water, then dried using flowing nitrogen gas. Coating thicknesses were again measured using ellipsometry and compared to the initial thicknesses.

Spectroscopic Ellipsometry. Ellipsometry utilizes the change in polarization of light reflected from a sample to estimate various physical parameters, such as sample thickness and refractive index. Thicknesses of dried coatings were measured on atomically flat Si wafers coated with 100 nm $TiO_2$ using an M-44 ellipsometer (J. A. Woollam). Spectra were obtained between 400-750 nm at 55°, 65°, and 75° and were fit in WVASE software using a multilayer model consisting of a silicon substrate, a $TiO_2$ layer, and a Cauchy layer that represented the coating. For each sample, the thicknesses of the $TiO_2$ and coating layers were fit. A refractive index of 1.45, a value typically used for proteins, was assumed for the coating layer. Typical fits resulted in a mean squared error of less than 10. Each condition was measured with at least 3 replicates per sample.

Fourier-Transform Infrared Spectroscopy (FTIR). FTIR is a nondestructive spectroscopic technique used for characterizing the secondary structures found in proteins and polypeptides. FTIR data acquisition was performed with a Bruker Vertex 70 Spectrometer equipped with a Bruker Platinum attenuated total reflection (ATR) diamond crystal cell. Measurements of coatings on $TiO_2$-coated Si wafers were performed with 100 scans and a resolution of 4 cm$^{-1}$ between a wavenumber range of 600-4000 cm$^{-1}$. Deconvolution surrounding the Amide I region (1595-1705 cm$^{-1}$) was performed using Igor Pro to determine relative secondary structure content found within the coatings. Second derivatives of the spectra were used to calculate peak positions, which were fit with Gaussian distributions. Bands within the frequency range of 1616-1637 cm$^{-1}$ and 1695-1705 cm$^{-1}$ represented β-sheet structures while bands in the frequency range of 1638-1655 cm$^{-1}$ were attributed to random coil, 1656-1663 cm$^{-1}$ were attributed to α-helices, and 1663-1695 cm$^{-1}$ were attributed to β-turns. Three replicates per condition were measured.

Atomic Force Microscopy (AFM). AFM is a technique that produces nanometer resolution images of a sample though measuring the deflection of a tip in close proximity to the sample surface. Height images of dry coatings on $TiO_2$-coated Si wafers were obtained using an Asylum MFP3D AFM operated in tapping mode with Tap150AI-G AFM cantilevers. Images were collected at 512×512 pixel resolution with a scanning rate around 1 Hz. Size analysis of features was done using ImageJ software by measuring the apparent diameter of 100 random and individual globules found throughout the image and are given as average and standard deviation.

AFM nanoindentation was performed in ultrapure water using a JPK ForceRobot 300 (JPK Instruments AG, Berlin, Germany). Soft spherical silicon cantilevers (Nanotools, Munich, Germany) with a spring constant of 0.2 N/m were used with a tip velocity of 1000 nm/s over a z-piezo distance of 500 nm with no dwell time. The contact force was limited to a few nN to minimize indentation depth. The spring constant was determined using the thermal tune method and the tip radius was measured by SEM imaging to be 23 nm in diameter. To extract the Young's modulus, the force-distance curves were fitted with the Hertz model.

Liquid AFM imaging was performed using a NanoWizard IIIa AFM (JPK Instruments AG, Berlin, Germany) operated in tapping mode. Imaging in dry state was performed utilizing SSS-NCHR super sharp silicon cantilevers (Nanosensors, Neuchâtel, Switzerland) with a nominal radius of less than 2 nm. Then, images of hydrated samples in 150 mM NaCl aqueous solution were obtained using ScanAsyst Fluid+cantilevers (Bruker Nano Inc., Tucson, AZ) with 2 nm radius tip, enabling high-resolution imaging in fluid.

Water Contact Angle Measurement. Surface wettability of clean and coated substrates was assessed by measuring static water contact angle using a Kruss DSA100 Drop Shape Analyzer using the Sessile Drop method. Three microliters of water were deposited onto each sample, and the image of the droplet was captured on camera. The angle of the solid-liquid and liquid-vapor interface was fitted using the Drop Shape Analysis 4 software. The angles on the left and right sides of the droplet were averaged for each droplet. A minimum of 3 replicates were measured.

Streaming Potential Measurement. Streaming potential provides insight into the overall surface charge of a substrate by measuring the voltage gradient as an electrolyte solution is flown past the sample to provide information on the zeta potential of the sample. Surfaces that differ in surface charge or isoelectric point can be understood to have distinct surface chemistries, for example, due to coating or other modifications. To investigate the change in surface charge of uncoated and coated substrates, zeta potential measurements were performed using the Anton Paar SurPASS 3 Electrokinetic Analyzer equipped with an integrated titration unit and adjustable gap cell. Experiments on uncoated and coated samples were run using a 10 mM KCl electrolyte solution with a pH scan from 2.0 to 10.0 and a pH step of 0.5, with 4 measurements taken at each pH.

Scanning Electron Microscopy (SEM). SEM provides topographical images of a surface by scanning the surface with a beam of focused electrons. Poly-L-lactic acid electrospun fiber scaffolds with and without coatings were sputter coated with approximately 0.75 nm Au/Pd using a Hummer V Technics sputter coater, and a FEI Versa 3D dual Beam SEM was used to image the surface morphology of fiber scaffolds using an accelerating voltage of 2 kV.

X-ray Photoelectron Spectroscopy (XPS). Based on the photoelectric effect, XPS provides an analysis of the chemical composition of approximately the top 5-10 nm of a surface. The signal intensity at energies associated with each element present can be integrated to provide quantitative composition information. XPS experiments were performed using a PHI VersaProbe operating at ultrahigh vacuum ($10^{-10}$ Torr) with a monochromatic Al Kα X-ray source. Survey scans were taken from a binding energy range of 0-1000 eV, and high resolution energy scans were taken for C 1s (282-292 eV), O 1s (526-536 eV), and N 1s (396-404 eV) regions.

Fluorescence Imaging of Coated Scaffolds. To examine the uniformity of the silk fibroin coatings on electrospun poly-L-lactic acid scaffolds, the scaffolds with and without silk coatings were immersed in 1.5 mL of a solution including 0.2 mg fluorescein (FITC) isothiocyanate in 100 mM sodium bicarbonate buffer at pH 9.0. Under these basic conditions, FITC covalently conjugates to the primary amines of proteins. The conjugation reaction was covered with aluminum foil and allowed to incubate at room temperature for 1 hour. The scaffolds were then removed from the solution and heavily washed with 25 ml of ultrapure water for 30 seconds to remove any unattached FITC. The scaffolds were then dried under steady air flow and protected from light until imaging. The coated and uncoated scaffolds were then imaged in brightfield and fluorescence modes on an Olympus IX-81 Confocal Microscope. Using Metamorph Premier 7.7.30 imaging software, scaffolds were imaged at 40× magnification to visualize individual fibers. Images were first taken using brightfield microscopy and subsequently the FITC filter was used to image the FITC-labeled coating. A Z-series stack was taken for each field of view of fibers using the same gain (200) and exposure time (250 ms) setting.

Dorsal Root Ganglia (DRG) Culture and Analysis. To determine the effect of coated poly-L-lactic acid electrospun scaffolds on neurite outgrowth compared to uncoated scaffolds, lumbar and thoracic DRG extracted from P1 Sprague-Dawley rats were cultured on the surface of the scaffolds. Two DRG were plated in the middle of each scaffold and cultured in neurobasal medium including B27 supplement (2% v/v), L-glutamine (0.5 mM), penicillin-streptomycin (1% v/v), and nerve growth factor (50 ng/ml) for 72 hours at 37° C. Immunocytochemistry was used to assess neurite outgrowth on coated and uncoated scaffolds. DRG were fixed with paraformaldehyde (4% v/v in phosphate buffered saline; PBS) for 15 minutes, then washed with PBS twice.

DRG were then incubated for 1 hour at room temperature with PBS including bovine serum albumin (BSA, 5% w/v) and Triton X-100 (0.01% v/v) to prevent non-specific binding of primary antibody. This was followed by overnight incubation (18 hours) at 4° C. with primary antibody RT-97 against neurofilament (1:250 in PBS) including BSA (5% w/v) and Tween-20 (1% v/v). DRG were then washed with PBS twice and incubated for 2 hours with Alexafluor-488 donkey antimouse secondary antibody (1:1000) at room temperature. DRG were washed with 4',6-diamidino-2-phenylindole (DAPI; 1:1000 in PBS) then twice with PBS prior to imaging. The number of adhered DRG on coated and uncoated scaffolds was counted at this point. A minimum of n=6 DRG from 4 separate animals were assess for DRG adhesion.

DRG adhered on coated and uncoated scaffolds were visualized using an Olympus IX-81 Confocal Microscope and Metamorph Premier 7.730 imaging software. Imaging for analysis was done at 4× magnification using FITC and DAPI filter sets to visualize neurons and nuclei respectively. A Z-series stack was taken for each field of view for each DRG with adjustments to gain and exposure to ensure neurites were visible in low signal areas. Consecutive fields of view were imaged to include the entire DRG and neurites. A minimum of n=6 DRG from 5 separate animals were imaged for each scaffold type. ImageJ software was used to stack confocal images of the DRG and subtract background noise. Adobe Photoshop CS2 as then used to stitch successive images together. Composite images were analyzed with ImageJ to measure neurite outgrowth; the five longest neurites on each side of the DRG body were measured and averaged. For the analysis, the average of each side of the DRG was considered a technical replicate. DRG aspect ratio was determined by dividing the longest DRG length (from the end to end of neurites) by the widest width of the DRG. A minimum of n=6 DRG from 4 animals were imaged for each fiber group.

Fluorimetry. The quantity of non-silk fibroin molecules integrated into the coating by co-assembly with silk fibroin was measured using a Fluorolog-Tau3 Fluorometer with the detector at a 90° angle from the incoming light source. First, non-silk fibroin proteins, including bovine serum albumin (BSA), α-lactalbumin (ALAC), β-lactoglobulin (BLAC), Lysozyme (LYS) were labeled with FITC following a procedure described by the ThermoFisher FluoReporter FITC Protein Labeling Kit. Proteins were added to a FITC solution (100 mM sodium bicarbonate buffer at pH 9.0) including a molar ratio of protein to FITC of 1:4 for BSA, ALAC, and BLAC, and a 2:3 ratio for LYS. The labeling reaction was covered with aluminum foil and allowed to incubate at room temperature for 1 hour. Extensive dialysis was then performed to remove the unreacted FITC using a Float-A-Lyzer dialysis unit with a 3 kDa molecular weight cut-off. To measure the fluorescence of coatings loaded with these fluorescent proteins or Rhodamine B, coated glass coverslips were placed in a sample holder with the coverslip at a 15° angle to the detector and 75° from the incoming light source. An excitation wavelength of 495 nm was used for FITC-labeled proteins and the emission spectrum from 450-650 nm was collected. An excitation wavelength of 558 nm was used for rhodamine B and the emission spectrum from 570-800 nm was collected. The normalized quantity of non-silk fibroin molecules integrated into the coating as the concentration of the molecule in the composition increased was calculated by dividing the fluorescence intensity of loaded coatings (at 524 nm for FITC or 577 nm for Rhodamine B) by the maximum fluorescence intensity achieved by any sample. Three replicates were measured for each data point.

Figure 5:
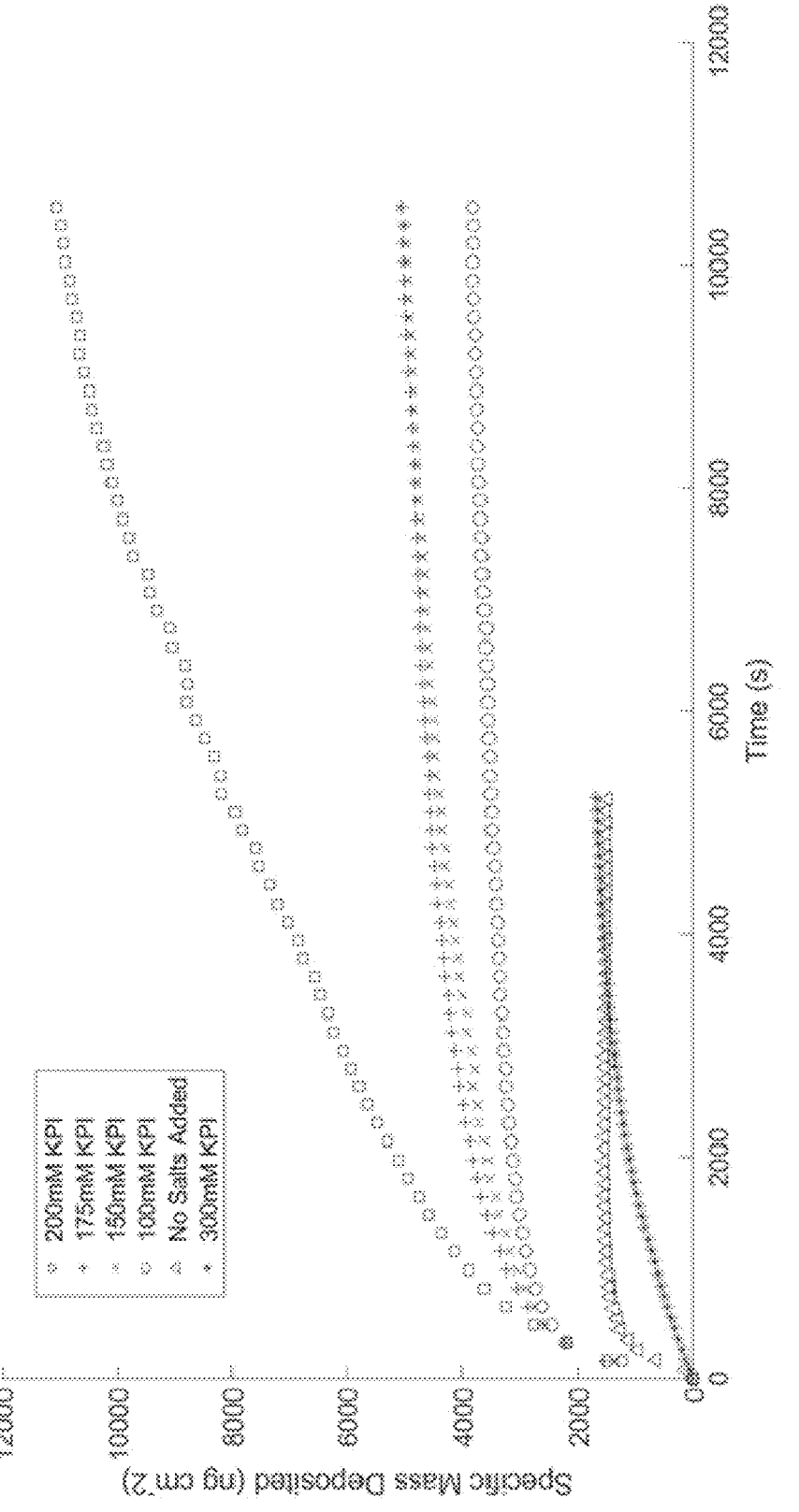
FIG. 5 is a graph of Quartz Crystal Microbalance with Dissipation (QCM-D) analysis of coating growth using a composition according to some embodiments of the present disclosure.

Example 1: Continuous Coating Growth with Phosphate as a Kosmotropic Agent. Coating growth was observed by QCM-D using a composition including 0.5 mg/mL *Bombyx mori* silk fibroin and various concentrations of potassium phosphate as a kosmotropic agent. The potassium phosphate was provided by a mixture of $KH_2PO_4$ and $K_2HPO_4$ that kept the solution buffered at pH 5. The temperature was maintained at 25° C. during the experiment. As shown in FIG. 5, compositions including 200 mM potassium phosphate yielded continuous and indefinite silk fibroin adsorption that did not reach saturation even after 3 hours. Compared to compositions with higher or lower potassium phosphate concentration, or no potassium phosphate at all, the composition including 200 mM potassium phosphate also yielded the largest amount of total adsorbed mass.

Figure 6:
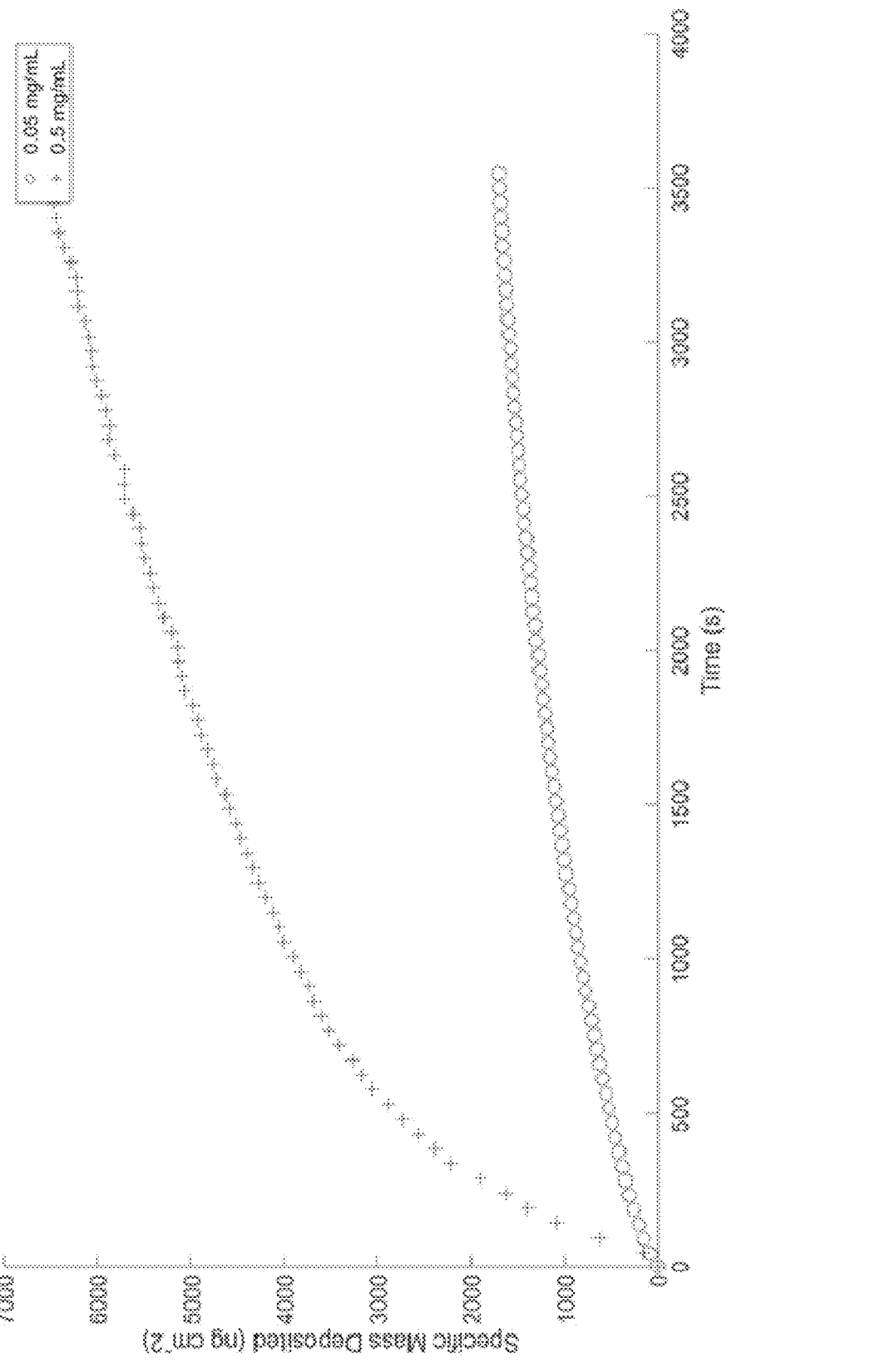
FIG. 6 is a graph of QCM-D analysis of coating growth using a composition according to some embodiments of the present disclosure.

Example 2: Dependence of Coating Growth Rate Silk Fibroin Concentration. Coating growth was observed by QCM-D using a composition including 200 mM potassium phosphate and *Bombyx mori* silk fibroin at 0.05 mg/mL or 0.5 mg/mL concentration. As shown in FIG. 6, both concentrations of silk fibroin yielded continuous and indefinite coating growth without saturation or plateau in amount. However, the higher silk fibroin concentration yielded significantly faster coating growth rates during the duration of the coating process.

Figure 7:
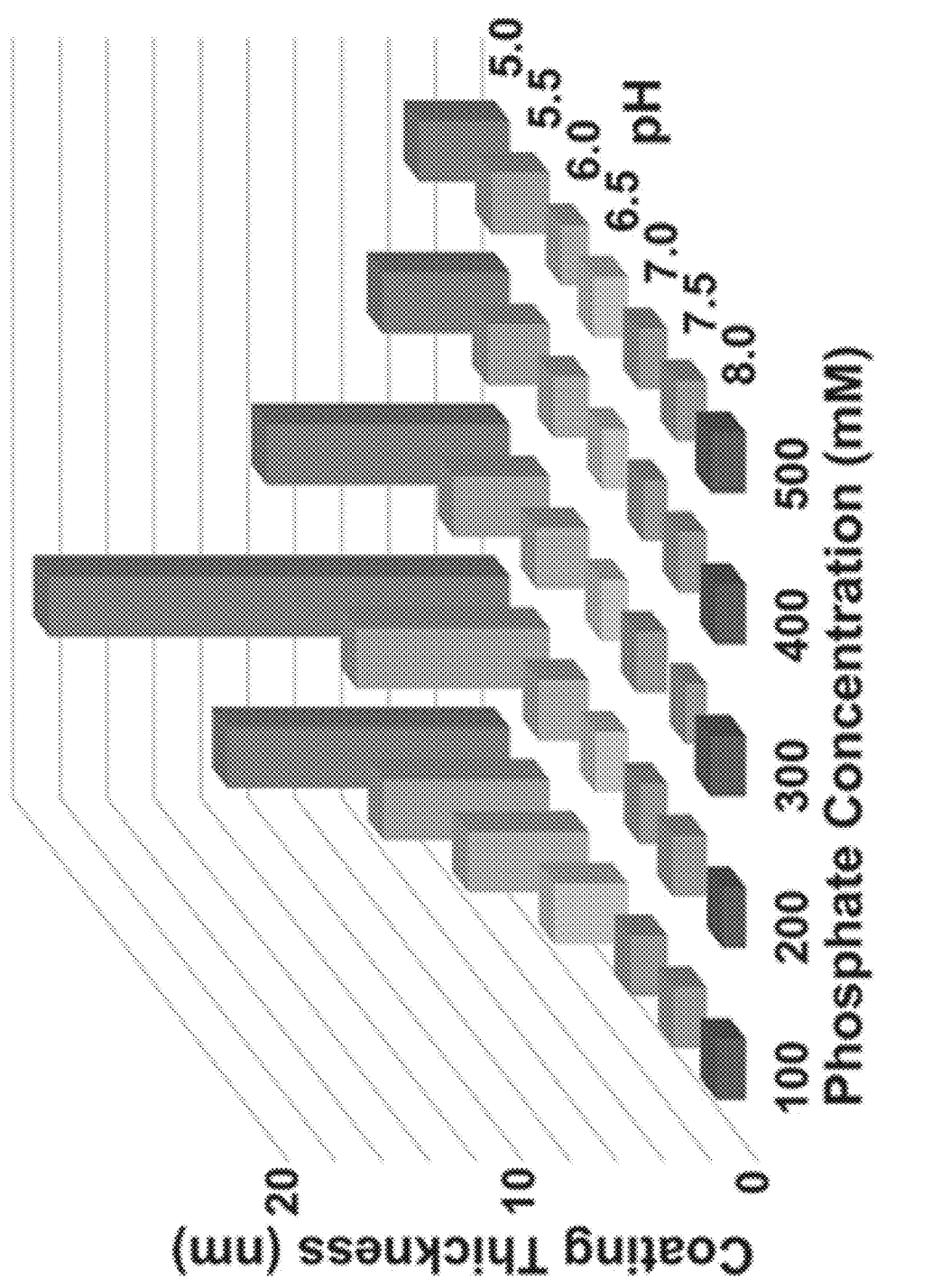
FIG. 7 is a graph of ellipsometry analysis of coatings according to some embodiments of the present disclosure.

Example 3: Dependence of Coating Growth Rate on pH and Phosphate Concentration. The growth of silk fibroin coatings at different pH and phosphate ion concentrations was assessed using spectroscopic ellipsometry. Compositions including 0.5 mg/mL *Bombyx mori* silk fibroin and varying concentrations of potassium phosphate were used to coat $TiO_2$-coated Si wafer substrates for 24 hours of coating time. The potassium phosphate was provided by mixtures of $KH_2PO_4$ and $K_2HPO_4$ that buffered the solution at pH ranging from 5-8. During the 24-hour coating time, substrates were immersed in the composition and agitated on a 22° C. orbital shaker at 60 RPM. After the coating time, the substrates were rinsed with ultrapure water for at least 30 seconds then dried using a stream of nitrogen gas. As shown in FIG. 7, thickness measurements by ellipsometry demonstrated that coating growth was maximized in a composition including 200 mM potassium phosphate at pH 5, with the coating reaching 19.6±1.2 nm after 24 hours. Compositions including more or less potassium phosphate than 200 mM or higher pH than 5 demonstrated slower coating growth rates.

Figure 8:
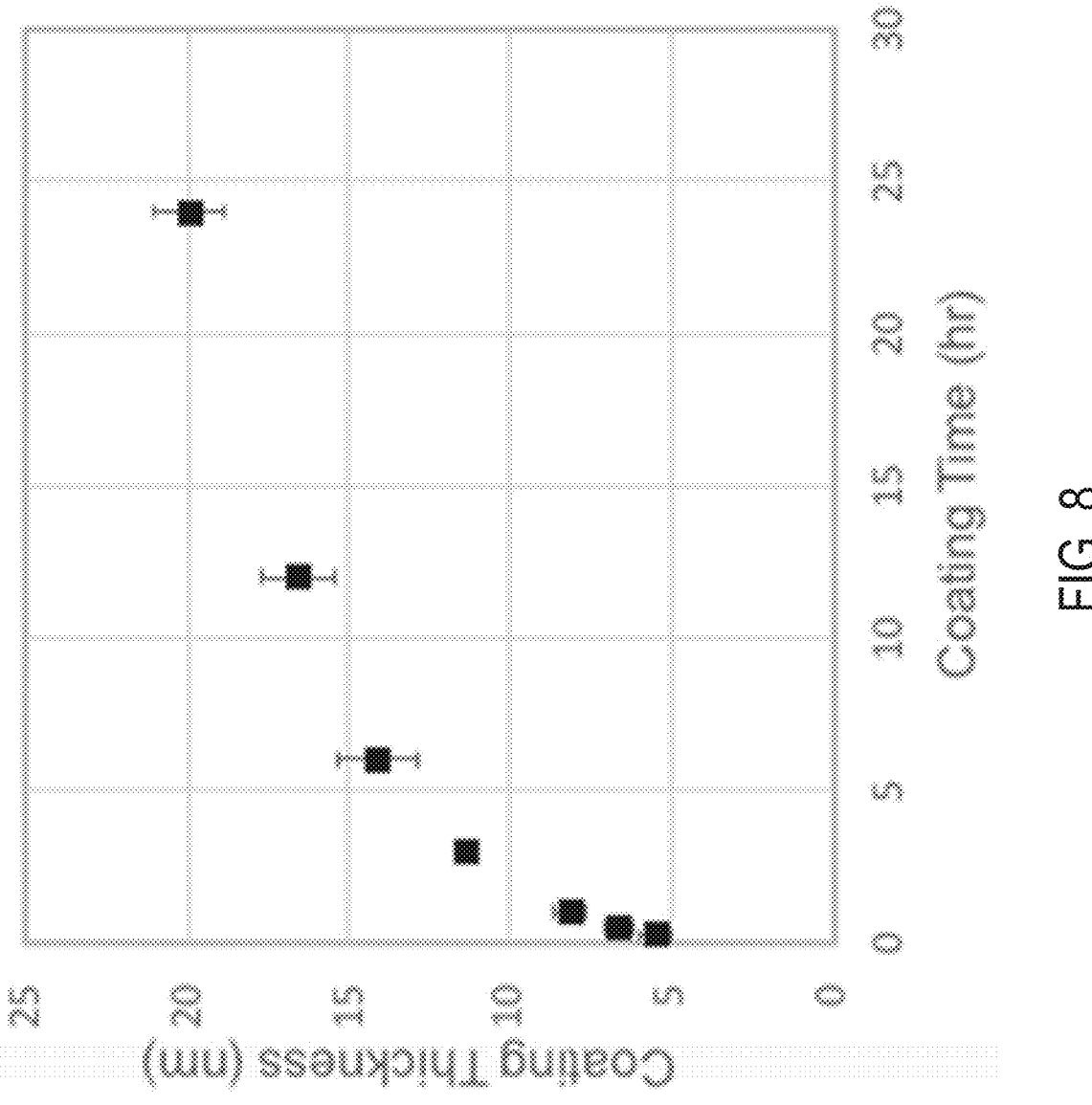
FIG. 8 is a graph of ellipsometry analysis of coatings according to some embodiments of the present disclosure.

Example 4: Dependence of Coating Thickness on Coating Time. The thickness of coatings resulting from coating times ranging from 15 minutes to 24 hours was measured by ellipsometry. Coatings were in which a $TiO_2$-coated Si wafer substrate was immersed in a composition including 0.5 mg/mL *Bombyx mori* silk fibroin with 200 mM potassium phosphate, as provided by a mixture of $KH_2PO_4$ and $K_2HPO_4$ that kept the solution buffered at pH 5, at 25° C. on an orbital shaker set at 60 RPM. As shown in FIG. 8, the results showed that coating thickness increased logarithmically with coating time. For this composition, thickness increased rapidly at early timepoints, then more slowly after 6 hours, though growth continued even after 24 hours.

Figure 9:
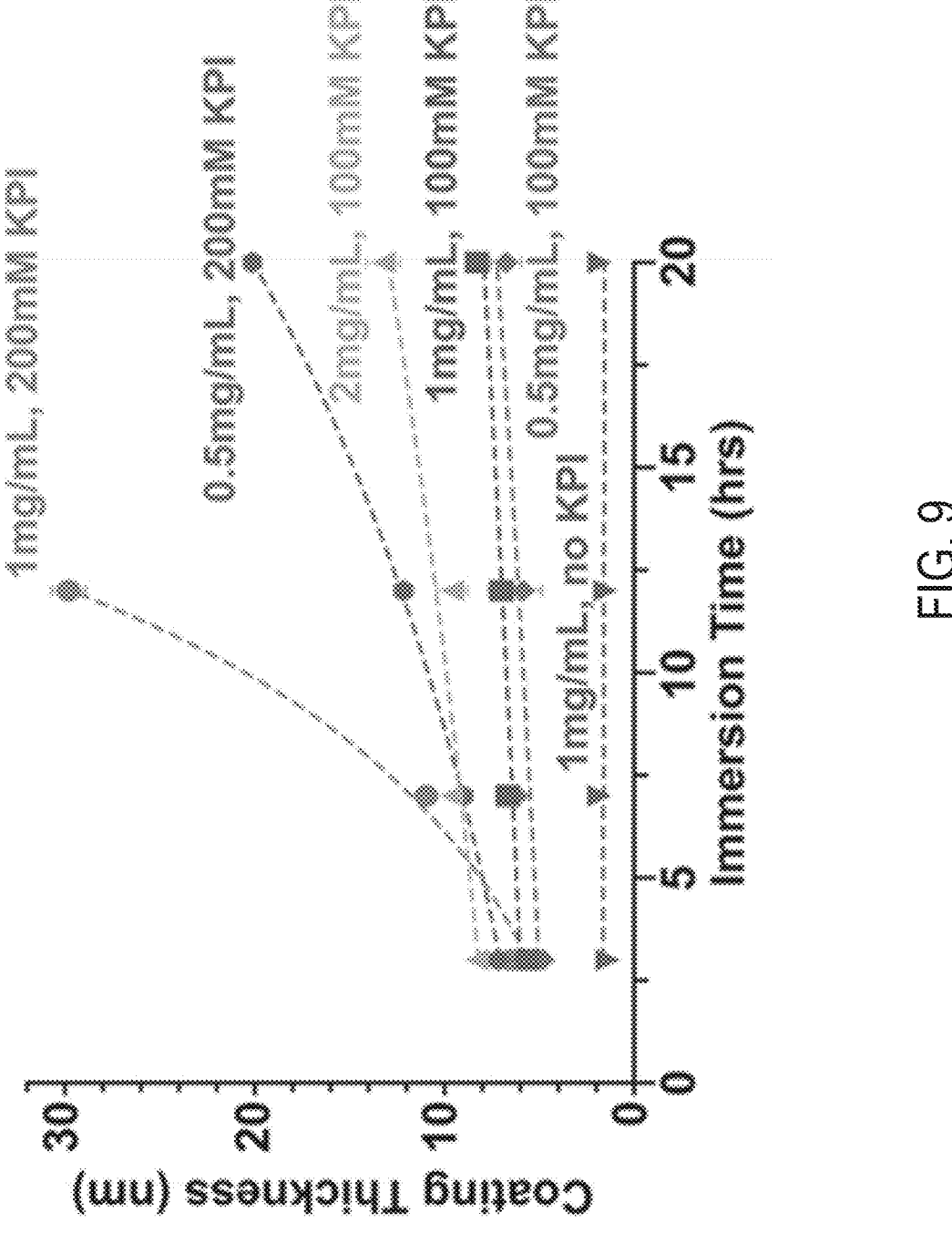
FIG. 9 is a graph of ellipsometry analysis of coatings according to some embodiments of the present disclosure.

As shown in FIG. 9, coatings made using the recombinant silk fibroin eADF4(C16) demonstrated similar coating growth in the presence of potassium phosphate used as a kosmotropic agent, whereas no coating growth was observed in the absence of potassium phosphate. For eADF4 (C16), coating growth was exponential, increasing slowly at early coating times, then more rapidly at later time points. No saturation in coating thickness or cessation of coating growth was observed. Furthermore, coating growth at 200 mM potassium phosphate was faster than at 100 mM phosphate and was also increased by higher eADF4(C16) concentration.

Figure 10:
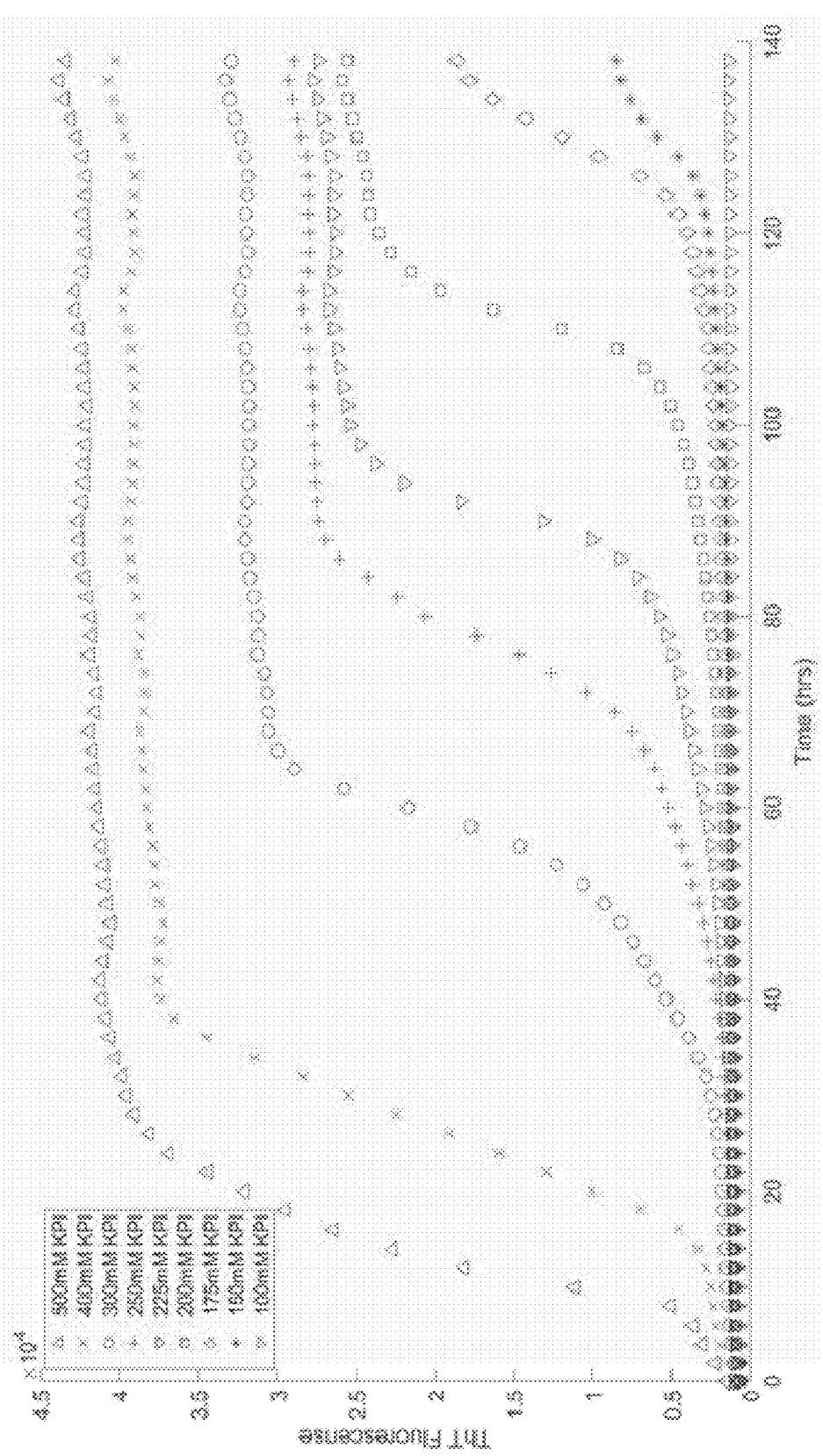
FIG. 10 is a graph of a Thioflavin T (ThT) assay of compositions according to some embodiments of the present disclosure.

Example 5: Self-Assembly Propensity of Silk Fibroin in Compositions. The solution-phase self-assembly of *Bombyx mori* silk fibroin in compositions including 0.5 mg/mL silk fibroin at pH 5 with varying potassium phosphate concentrations was assessed using ThT assays for β-sheet formation. A rapid rise in the fluorescence intensity at 482 nm corresponds to the initiation of β-sheet driven self-assembly, which is expected to occur if protein-protein interactions are sufficiently strong. Referring now to FIG. 10, for all potassium phosphate concentrations examined, a lag time was observed as expected for a nucleation-growth self-assembly mechanism. However, for potassium phosphate concentrations higher than 400 mM, the lag time was less than 16.6 hours, while the lag time for potassium phosphate concentrations 300 mM or lower was longer than 46.5 hours. Combined with results presented in Examples 1 and 3 on coating growth kinetics, without wishing to be bound by theory, this result suggests that concentrations of kosmotropic agents that generate too much self-assembly in the composition, as indicated by a short lag time, discourage coating growth.

Figure 11:
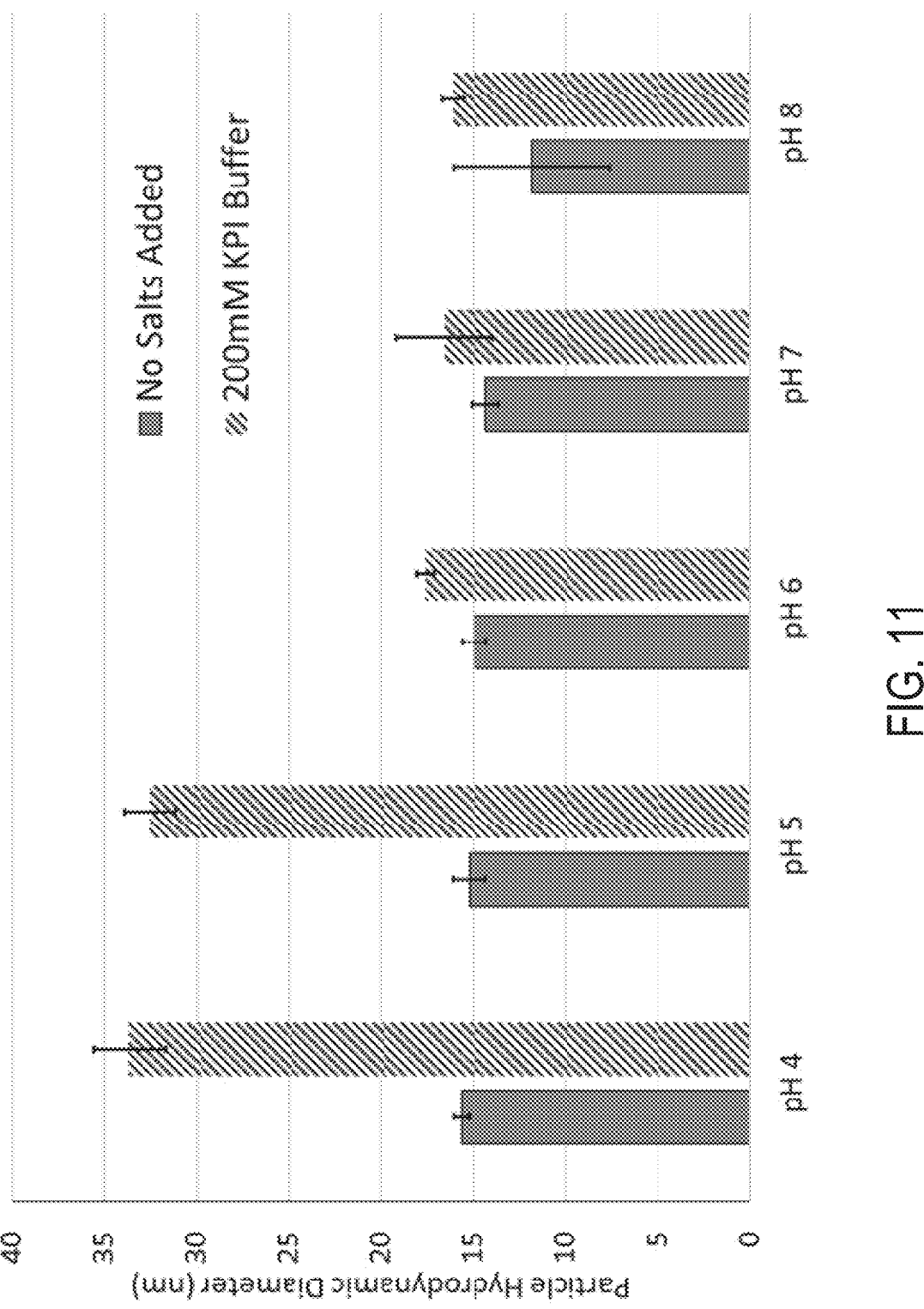
FIG. 11 is a graph of a dynamic light scattering (DLS) analysis of compositions according to some embodiments of the present disclosure.

The aggregation of silk fibroin in composition including 0.5 mg/mL *Bombyx mori* silk fibroin and 200 mM phosphate at pH 4-8 was characterized by DLS. As shown in FIG. 11, results showed that formation of an aggregate species approximately 33 nm in hydrodynamic diameter occurred if potassium phosphate was present as a kosmotropic agent and the pH was lower than 6. No aggregation occurred without potassium phosphate at any pH or with phosphate at pH higher than 6. Combined with results in Examples 1 and 3 that showed coating growth rate increasing with lower pH, without wishing to be bound by theory, these findings demonstrated that coating growth was more efficient in compositions that encourage an intermediate amount of attractive protein-protein interaction, whereas compositions that did not yield the 33 nm aggregate species also did not result in rapid coating growth in this case.

Figure 12A:
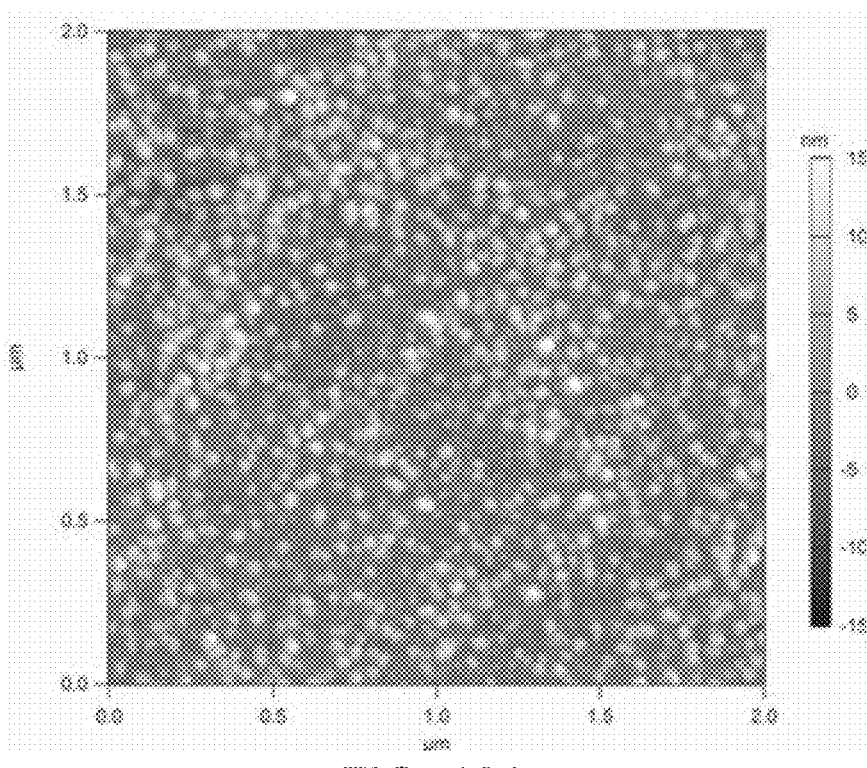
FIGS. 12A-12C portray Atomic Force Microscopy (AFM) images of coatings according to some embodiments of the present disclosure.
Figure 12B:
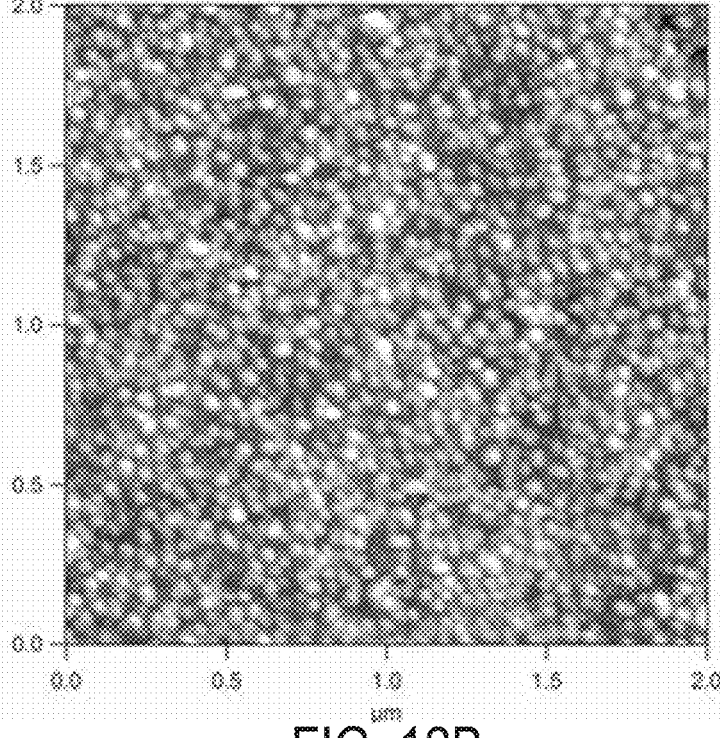
Figure 12C:
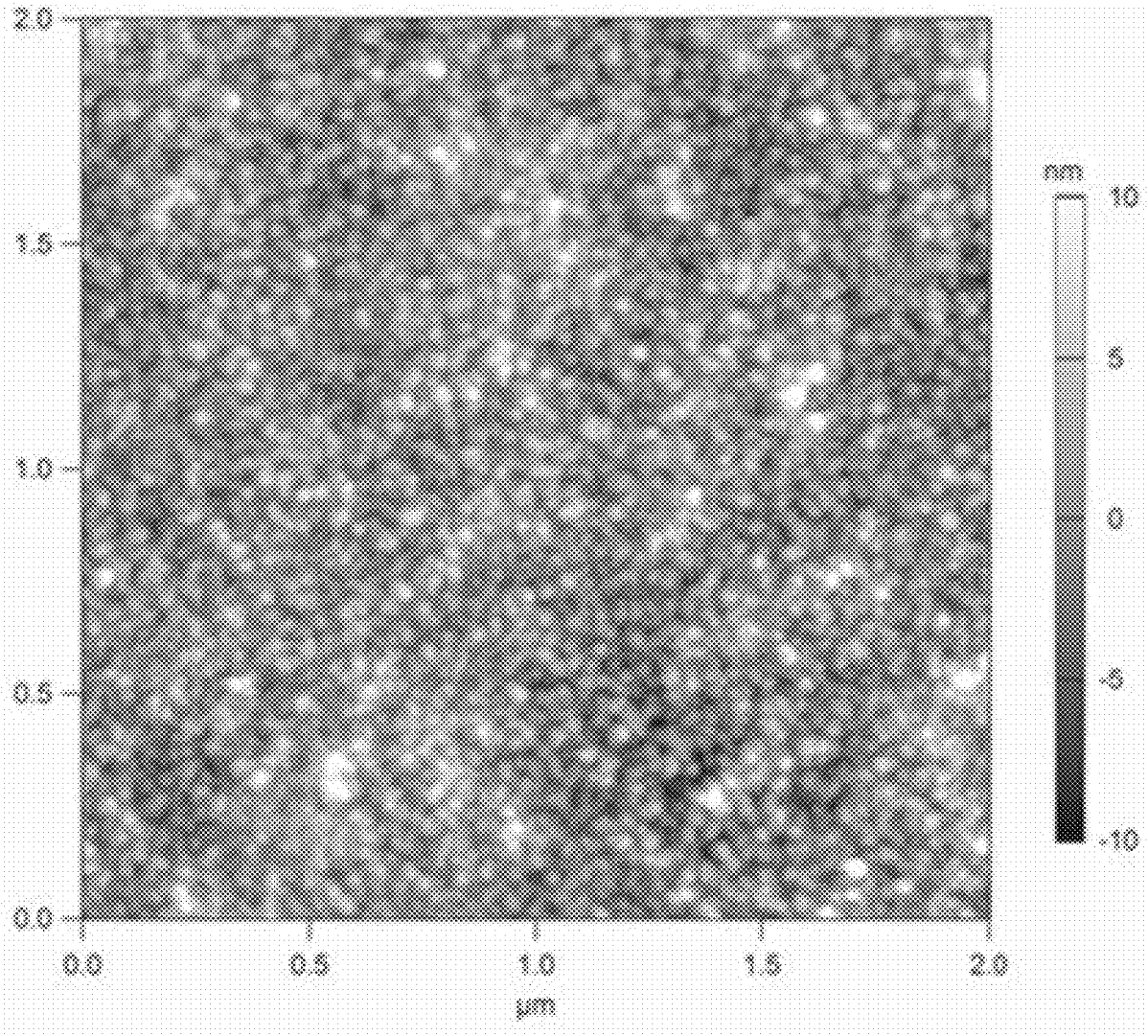

Example 6: Growth of Defect-Free Silk Fibroin Coatings. Referring now to FIGS. 12A-12C, the morphology of silk fibroin coatings was investigated by AFM. Coatings were made in which a $TiO_2$-coated Si substrate was immersed in a composition including 0.5 mg/mL *Bombyx mori* silk fibroin with 200 mM potassium phosphate, as provided by a mixture of $KH_2PO_4$ and $K_2HPO_4$ that kept the solution buffered at pH 5, for 24 hours at 22° C. on an orbital shaker set at 60 RPM. After the 24-hour coating time (FIG. 12C), the substrates were removed from the composition, rinsed with ultrapure water for at 30 seconds, and dried with a stream of nitrogen gas. AFM imaging of the coatings showed a nanoscale morphology comprising globular structures 41±7 nm in diameter. This coating morphology was homogeneous and free of features significantly larger than the globule size, such as large particles or fibers. The coating was smooth, with a root mean squared roughness of 2.8 nm without large hills or valleys across the entirety of the coating. Furthermore, AFM imaging of coatings using the same composition but with shorter coating times (1 hour (FIG. 12A) and 3 hours (FIG. 12B)) showed that coating growth in this case proceeded by accumulation of silk fibroin nanoglobules on the surface over time, with full coverage of the surface reached at approximately 3 hours.

Figure 13:
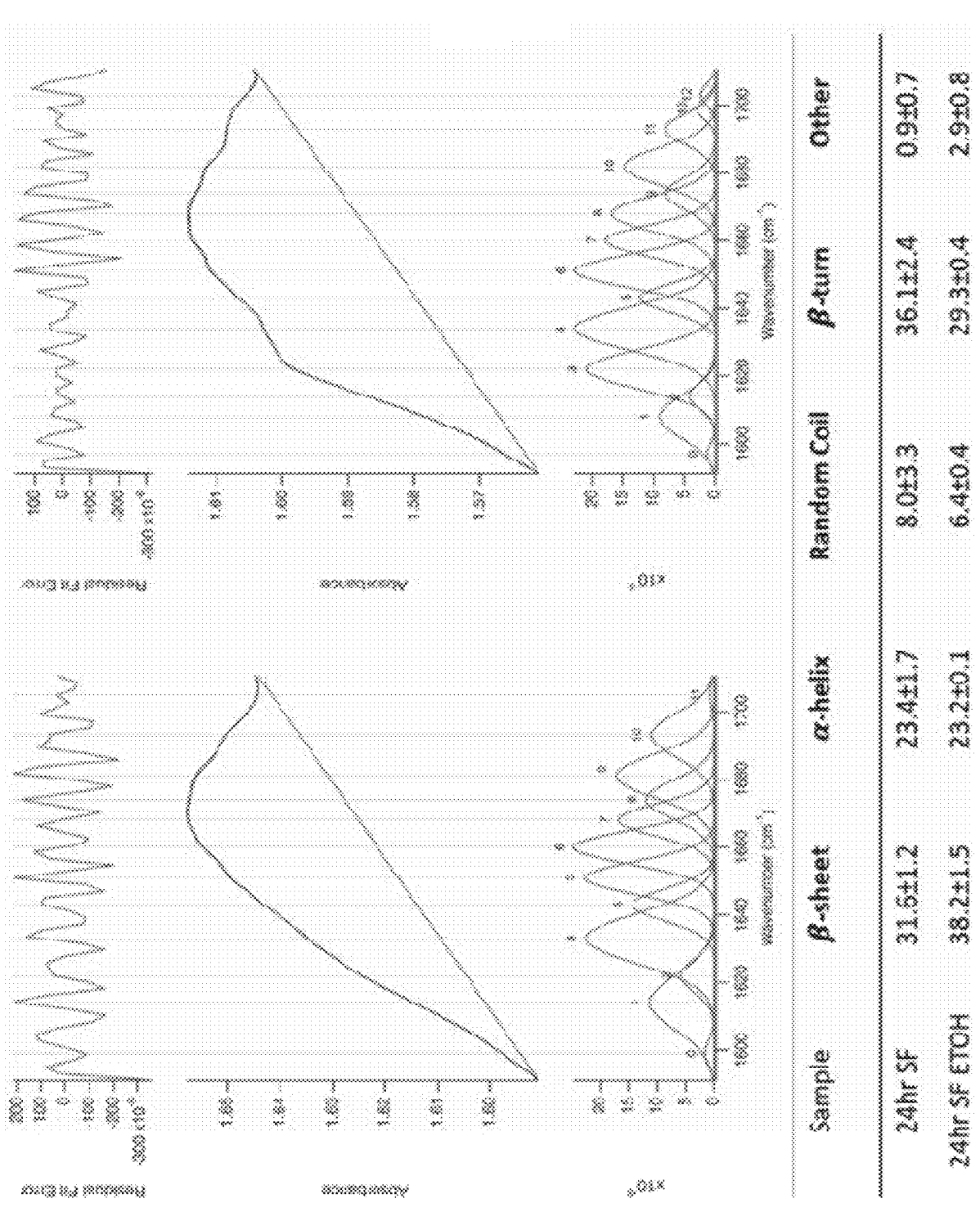
FIG. 13 portrays graphs of a Fourier-Transform Infrared Spectroscopy analysis of coatings according to some embodiments of the present disclosure.

Example 7: Growth of β-Sheet Rich Silk Fibroin Coatings. The secondary structures found within silk fibroin coatings were investigated using FTIR. Coatings were made in which a $TiO_2$ substrate was immersed in a composition including 0.5 mg/mL *Bombyx mori* silk fibroin with 200 mM potassium phosphate, as provided by a mixture of $KH_2PO_4$ and $K_2HPO_4$ that kept the solution buffered at pH 5, in aqueous solution for 24 hours at 22° C. on an orbital shaker set at 60 RPM. Referring now to FIG. 13, deconvolution of the Amide I region (1595-1705 $cm^{-1}$) suggested a high β-sheet content (31.6±1.2%) in these coatings, indicating that β-sheet driven self-assembly played an important role in the mechanism of coating growth. Additionally, further treatment of the coating with 70% ethanol, an organic solvent known to induce β-sheet formation in silk fibroin, only increased the overall β-sheet content to 38.2±1.5%.

Figure 14:
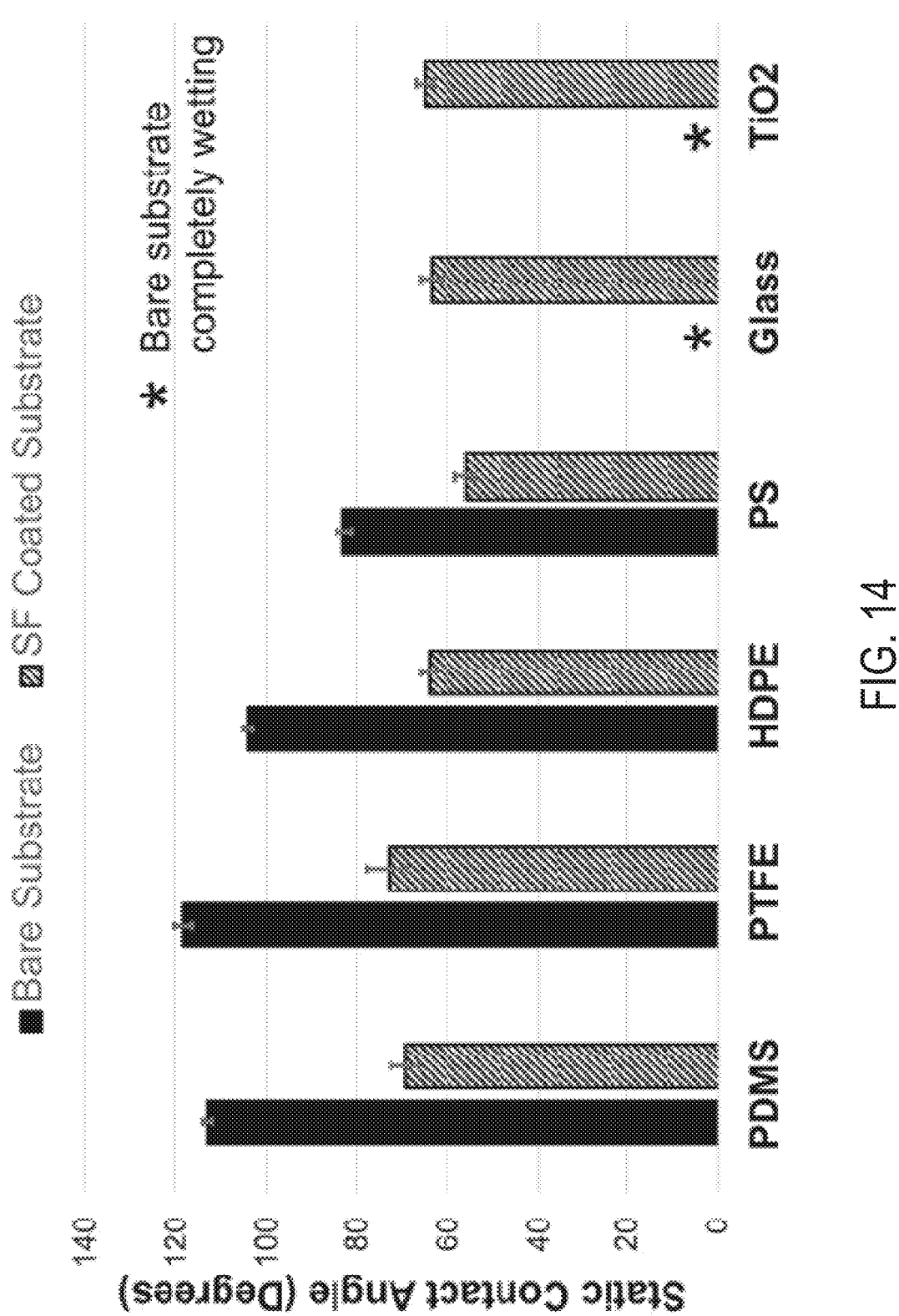
FIG. 14 is a graph of a static water contact angle analysis of coatings according to some embodiments of the present disclosure.

Example 8: Silk Fibroin Coatings Modify the Wettability of Surfaces. Referring now to FIG. 14, the ability of silk fibroin coatings to modify the wettability of organic and inorganic substrates was investigated by measuring static water contact angle on coated substrates. In one experiment, coatings were self-assembled on inorganic substrates, including polydimethylsiloxane, $TiO_2$, and glass, and organic substrates, including polystyrene, polytetrafluoroethylene, and high-density polyethylene. The coatings were made in which the substrates were immersed in a composition including 0.5 mg/mL *Bombyx mori* silk fibroin with 200 mM potassium phosphate, as provided by a mixture of $KH_2PO_4$ and $K_2HPO_4$ that keeps the solution buffered at pH 5, in aqueous solution for 24 hours at 22° C. on an orbital shaker set at 60 RPM. Static water contact angles of the substrates before coating were greater than 80° for polystyrene, polytetrafluoroethylene, high density polyethylene, and polydimethylsiloxane, which is consistent with the expected contact angles of these materials. Uncoated glass and $TiO_2$ were completely wetted by water and contact angles were close to 0° and could not be measured. After coating, all substrates demonstrated water contact angles of approximately 60°, which is consistent with the water contact angle of bulk *Bombyx mori* silk fibroin materials.

Figure 15:
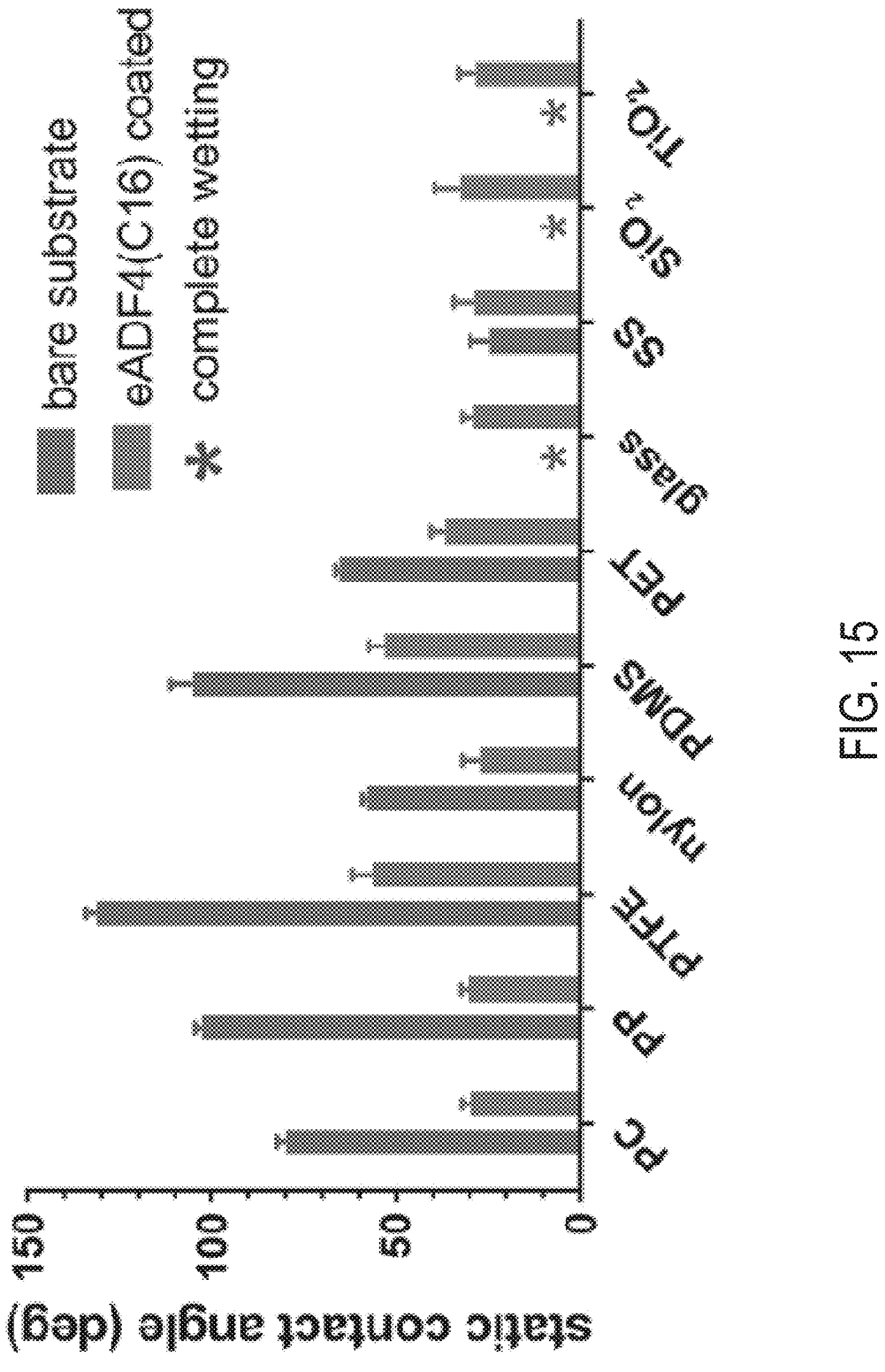
FIG. 15 is a graph of a static water contact angle analysis of coatings according to some embodiments of the present disclosure.

Referring now to FIG. 15, eADF4(C16) coatings were made on a variety of organic and inorganic substrates, including polytetrafluoroethylene, nylon, polypropylene, polydimethylsiloxane, polycarbonate, polyethylene terephthalate, glass, stainless steel, $TiO_2$, and $SiO_2$. Coatings were made by immersing substrates in an aqueous composition including 0.5 mg/mL eADF4(C16) with 200 mM $KH_2PO_4$, 25 mM bicine buffer, and 150 mM NaCl for 30 hours at 22° C. on an orbital shaker set at 60 RPM. Substrates that were hydrophobic prior to coating became more hydrophilic, while substrates that were hydrophilic and completely wet by water before coating became more hydrophobic. Generally, static water contact angles of coated substrates were ~30°, which is close to the contact angle of bulk eADF4 (C16).

Figure 16:
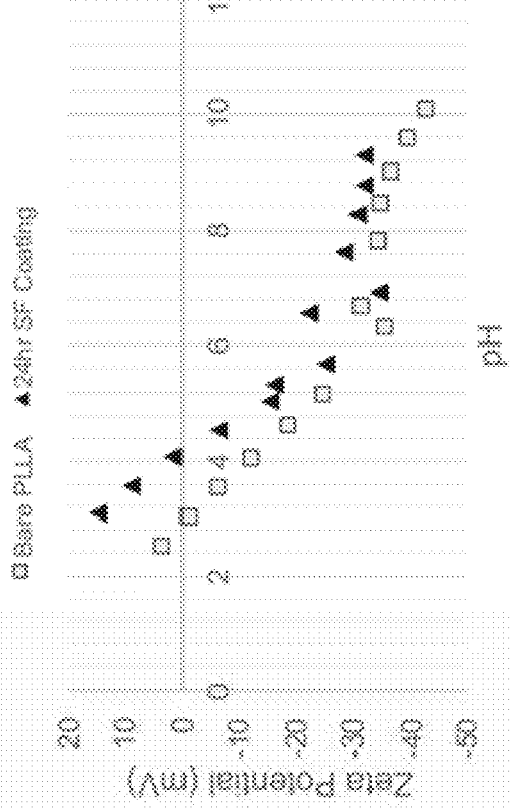
FIG. 16 is a graph of streaming potential measurement of poly-L-lactic acid (PLLA) coated with compositions according to some embodiments of the present disclosure.

Example 9: Silk Fibroin Coatings Modify the Surface Chemistry of Substrates. Referring now to FIG. 16, the ability of the self-assembled coatings to endow surfaces with new chemical functionality was examined using streaming potential analysis to measure the change in zeta potential and isoelectric point after coating. The isoelectric point of a surface is the pH at which the surface carries a zeta potential equal to zero. A poly-L-lactic acid substrate was coated in which the substrate was immersed in a composition including 0.5 mg/mL *Bombyx mori* silk fibroin with 200 mM potassium phosphate, as provided by a mixture of $KH_2PO_4$ and $K_2HPO_4$ that kept the solution buffered at pH 5, aqueous solution for 24 hours at 22° C. on an orbital shaker set at 60 RPM. Although bare and coated PLLA samples have similar zeta potential at higher pH, the isoelectric point of the coated sample is shifted from to approximately 4, which is close to the theoretical isoelectric point of *Bombyx mori* silk fibroin based on its primary sequence. A similar shift in isoelectric point after coating was also observed for polytetrafluoroethylene, polydimethylsiloxane, high density polyethylene, and $TiO_2$ substrates coated using the same method.

The ability of self-assembled silk fibroin coatings to change the surface chemistry of a substrate was also demonstrated by XPS. $TiO_2$-coated Si wafer substrates were immersed in a composition including 0.5 mg/mL *Bombyx mori* silk fibroin with 200 mM $KH_2PO_4$ and 10 mM bicine buffer for 48 hours at 22° C. on an orbital shaker set at 60 RPM. Referring now to FIGS. 17A and 17B, surface composition analysis by XPS of coated substrates showed that the ratio of carbon to nitrogen was 2.30, which closely matched the 2.25 carbon to nitrogen ratio of a drop-cast bulk silk fibroin film. Furthermore, high energy resolution spectra of the C1s region showed that bulk silk fibroin films and silk fibroin coatings formed by self-assembly have different distributions of binding energies, suggesting that the self-assembled coatings have secondary structure and bonding that is distinct from drop-cast coatings due to their method of formation.

Figure 18A:
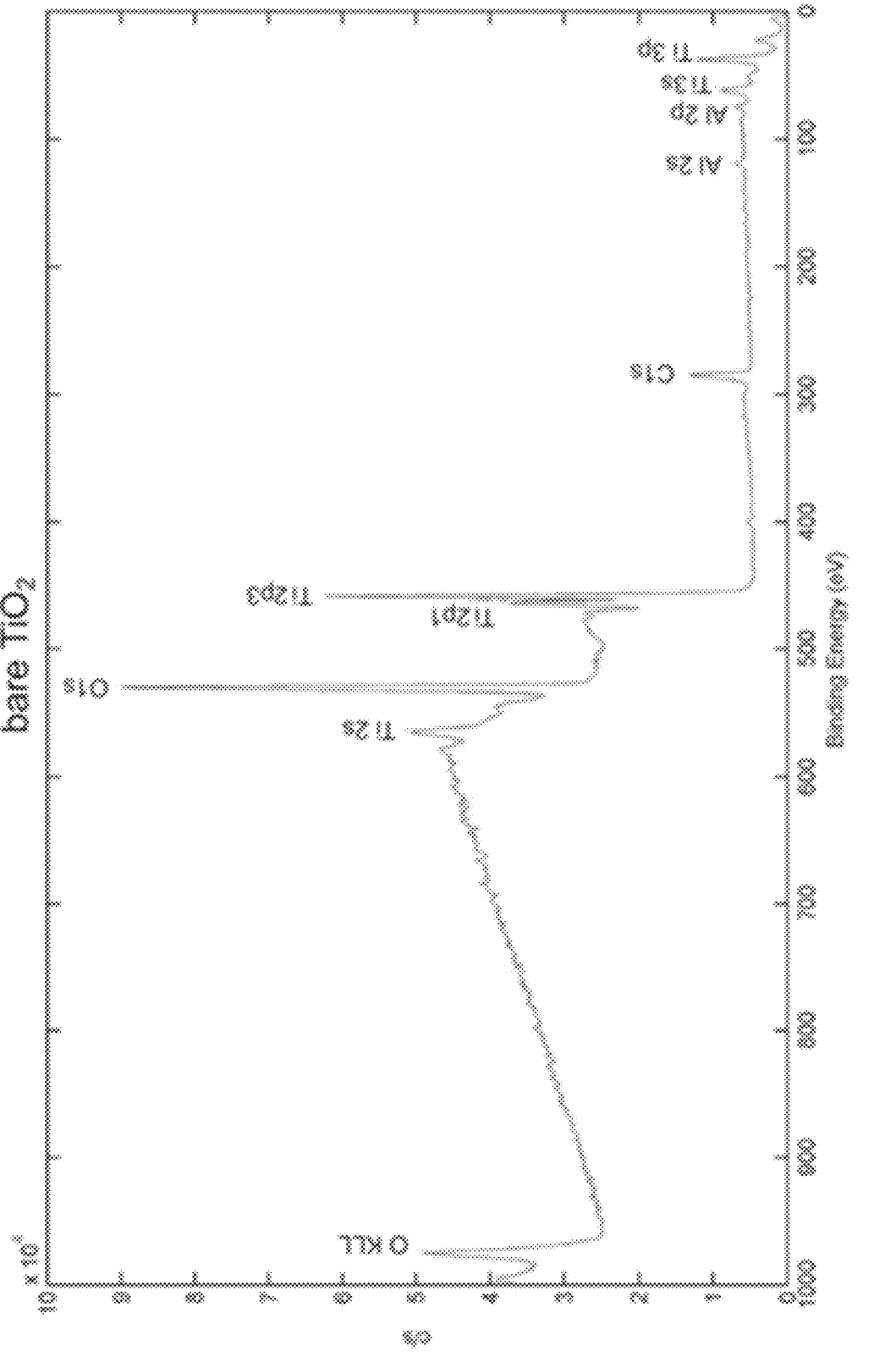
FIGS. 18A-18D are graphs of XPS analysis of bare $TiO_2$ substrate (FIG. 18A), drop-cast *Bombyx mori* silk fibroin film (FIG. 18B), and coatings according to some embodiments of the present disclosure (FIGS. 18C and 18D)
Figure 18B:
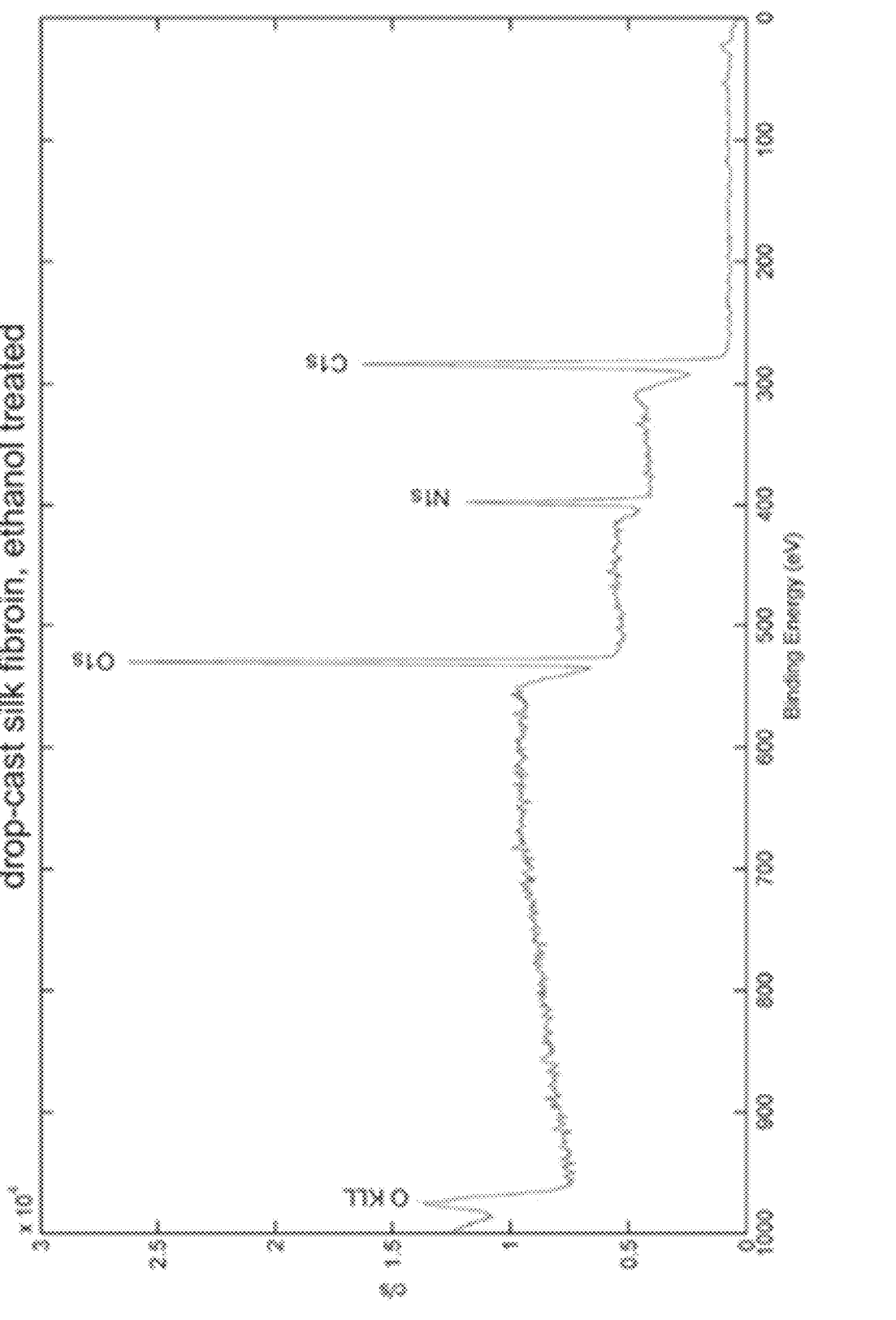
Figure 18C:
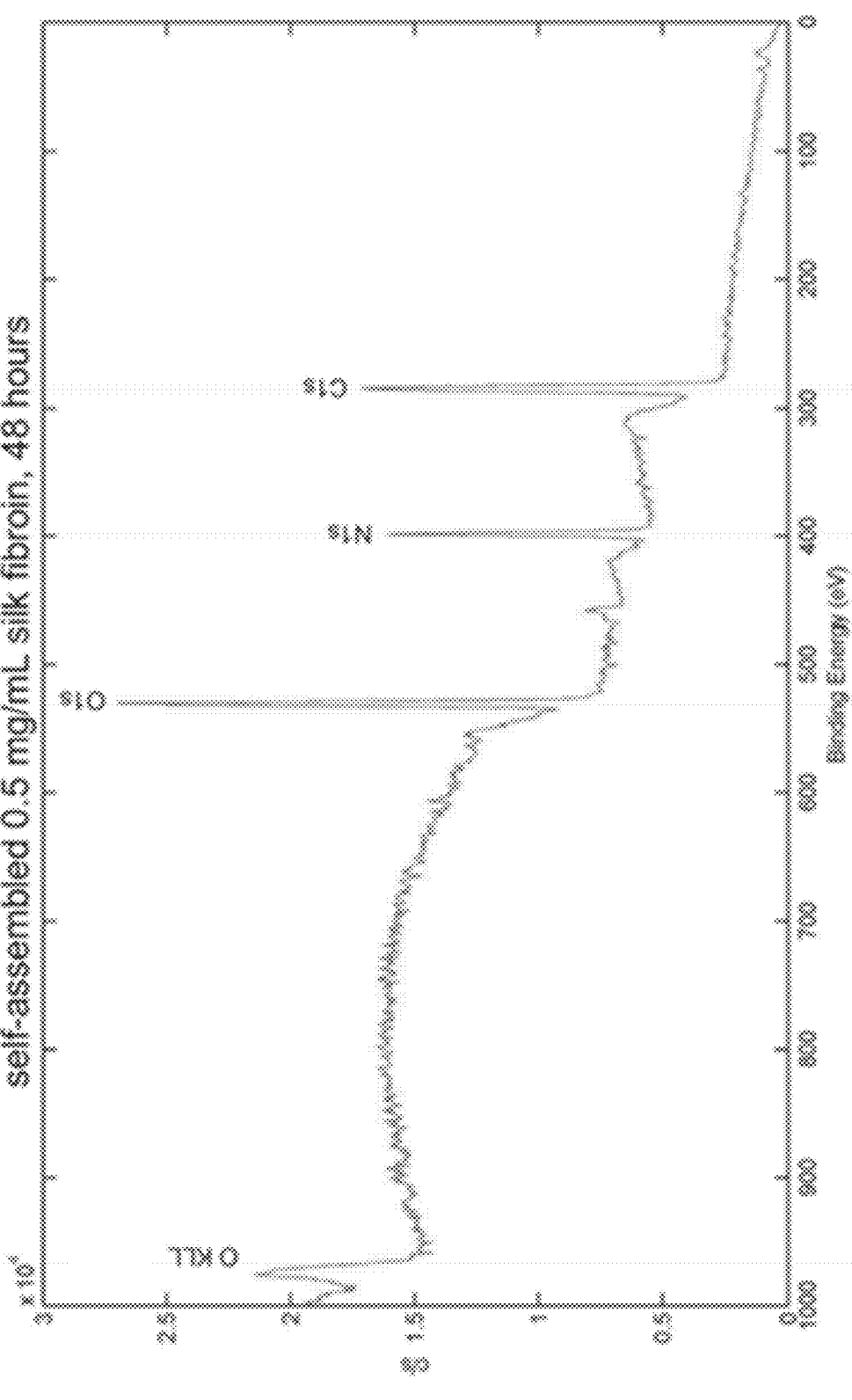
Figure 18D:
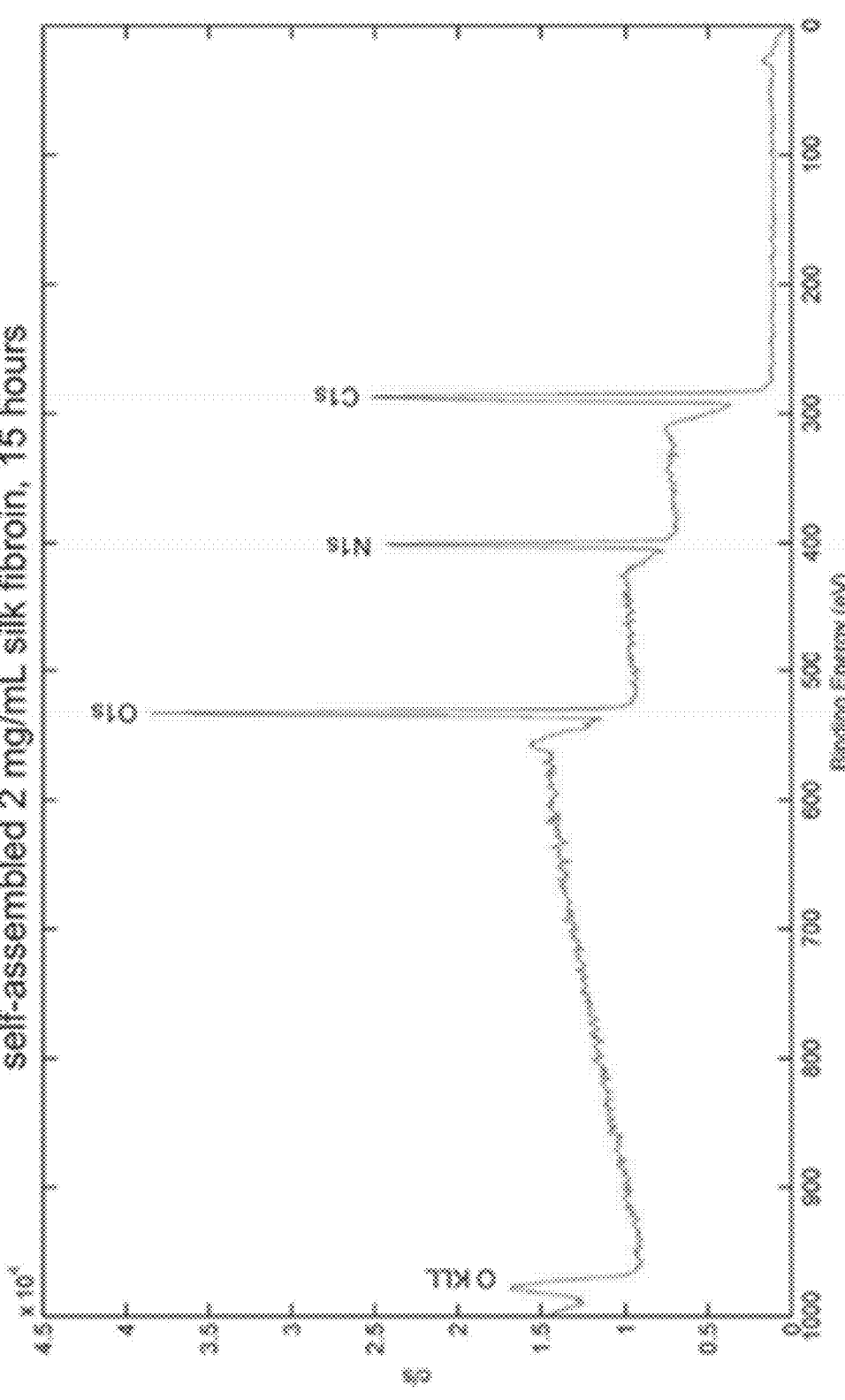

Additionally, XPS results showed that no Ti signal corresponding to the $TiO_2$ substrate was observed for self-assembled coatings made with either 0.5 mg/mL or 2 mg/mL *Bombyx mori* silk fibroin for 48 (FIG. 18C) or 15 hours (FIG. 18D), respectively (see FIGS. 18A-18B for comparison), suggesting that the silk fibroin completely covered the surfaces with a coating layer at least 10 nm thick.

Figure 19:
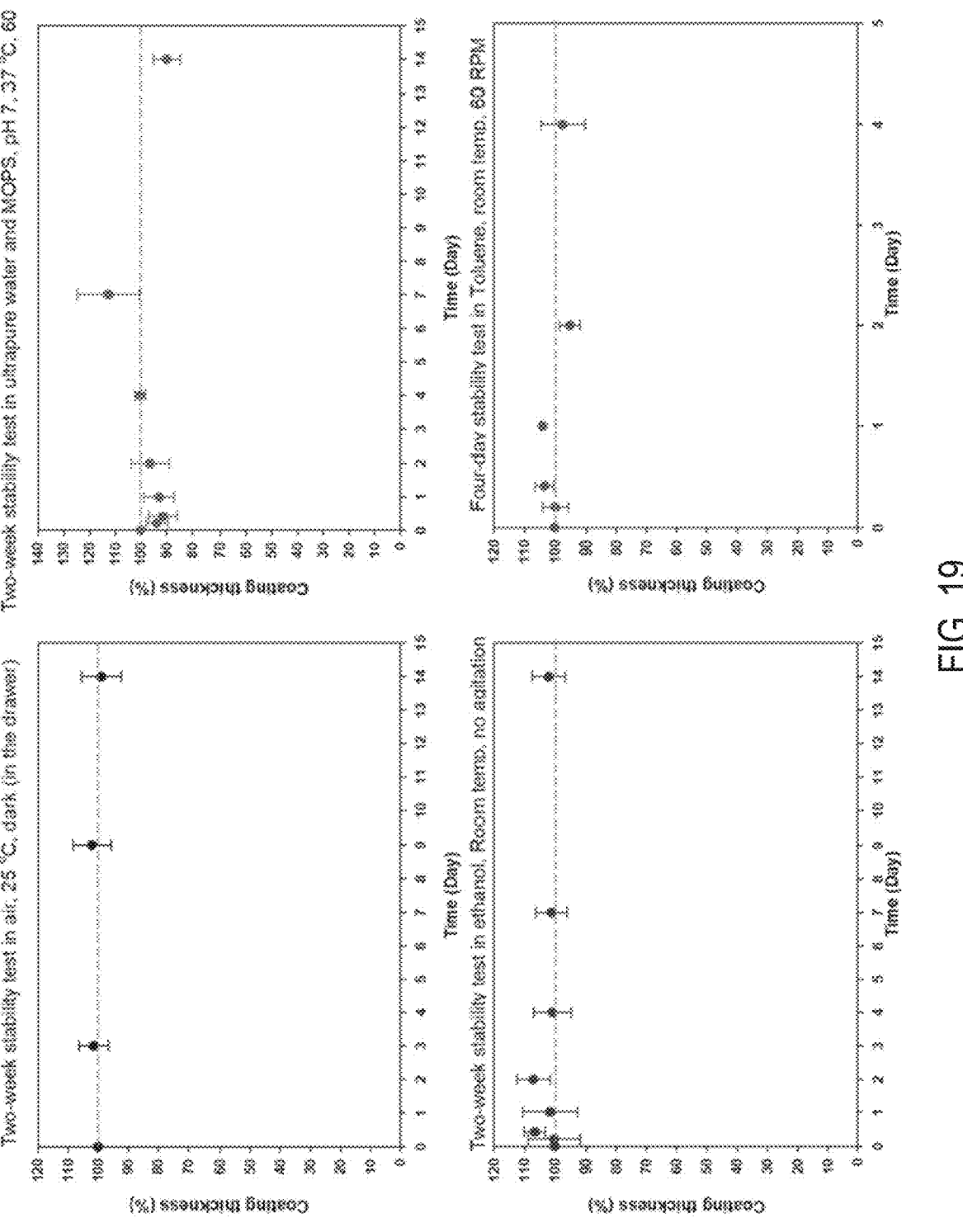
FIG. 19 portrays graphs of ellipsometry measurements of coatings according to some embodiments of the present disclosure.

Example 10: Stability of Silk Fibroin Coatings in Organic and Aqueous Solvents. The resistance of silk coatings to degradation in ambient air, ethanol, toluene, and ultrapure water buffered at pH 7 was examined using ellipsometry. Coatings on $TiO_2$-coated Si wafer substrates were made in which the substrate was immersed in a composition including 0.5 mg/mL *Bombyx mori* silk fibroin with 200 mM potassium phosphate, as provided by a mixture of $KH_2PO_4$ and $K_2HPO_4$ that kept the solution buffered at pH 5, in aqueous solution for 24 hours at 25° C. on an orbital shaker set at 60 RPM. Initial coating thicknesses were measured by ellipsometry. Coated substrates were then immersed in solvent and set to agitate in a 60 RPM orbital shaker at 25° C. for toluene and at 37° C. for buffered water, or left in a covered petri dish in ambient air. At each timepoint, coated substrates (n=3) were removed from the solvents, gently dipped in ultrapure water to remove excess solvent, then dried with a stream of nitrogen gas. Referring now to FIG. 19, ellipsometry was then used to measure the coating thickness and reported as a percentage normalized to the initial thickness. Results showed that silk fibroin coatings are resistant to significant mass loss, even when exposed to buffered water or ethanol for 14 days. Results also showed that coatings are stable in toluene for at least 4 days. Furthermore, no degradation was found for coatings stored in ambient air over 14 days.

Figure 20:
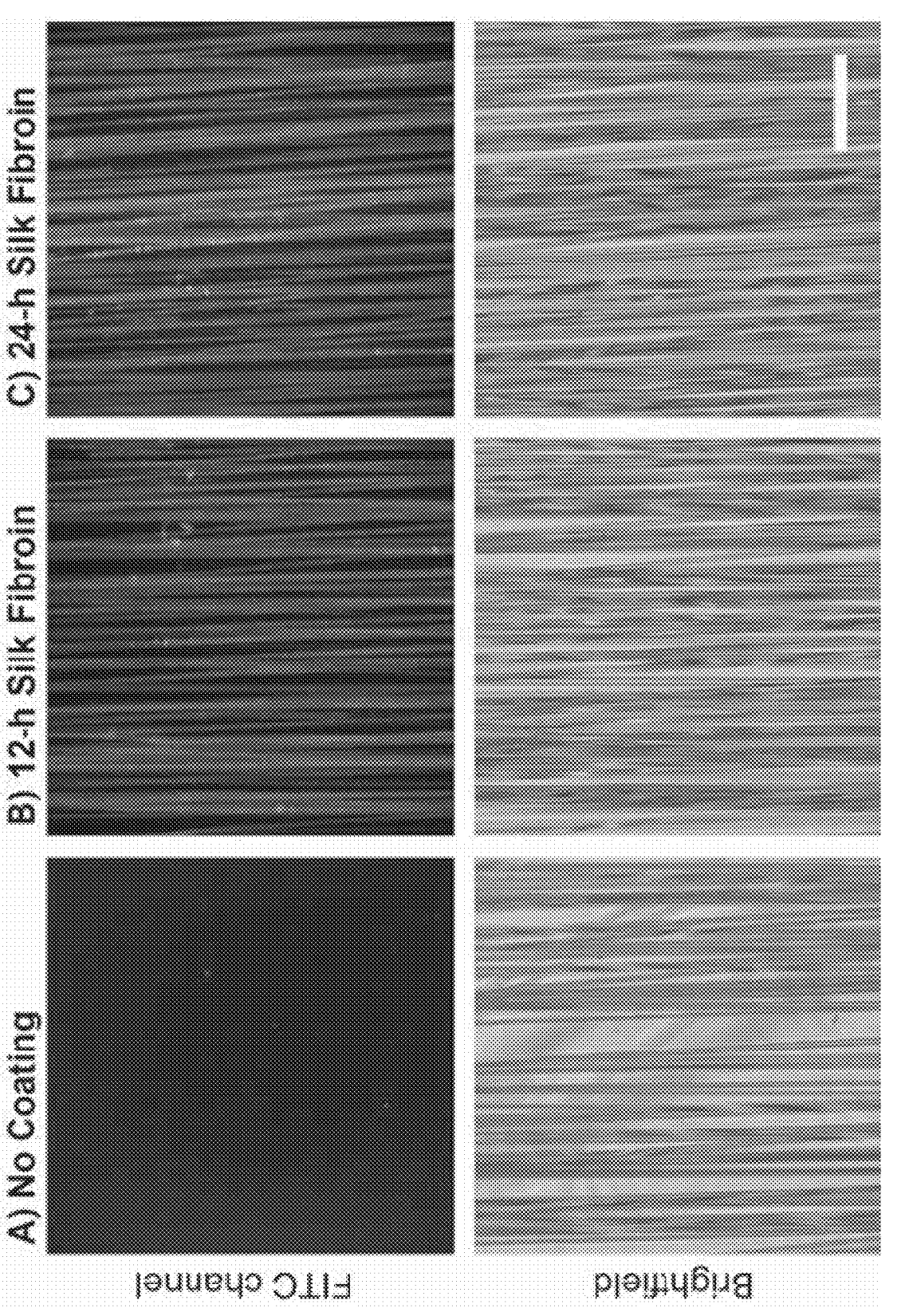
FIG. 20 portrays images of brightfield and confocal fluorescence microscopy analysis of electrospun poly-L-lactic acid scaffolds with and without coatings according to some embodiments of the present disclosure.
Figure 21A:
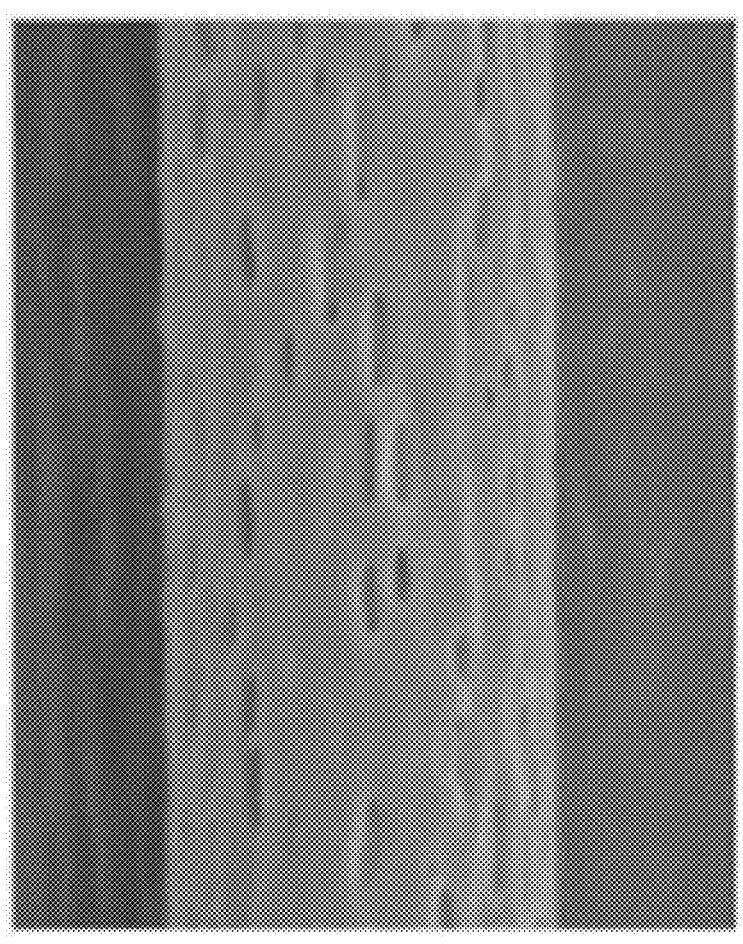
FIGS. 21A and 21B are images of scanning electron microscopy analysis of electrospun poly-L-lactic acid scaffolds with (FIG. 21B) and without (FIG. 21A) coatings according to some embodiments of the present disclosure.
Figure 21B:
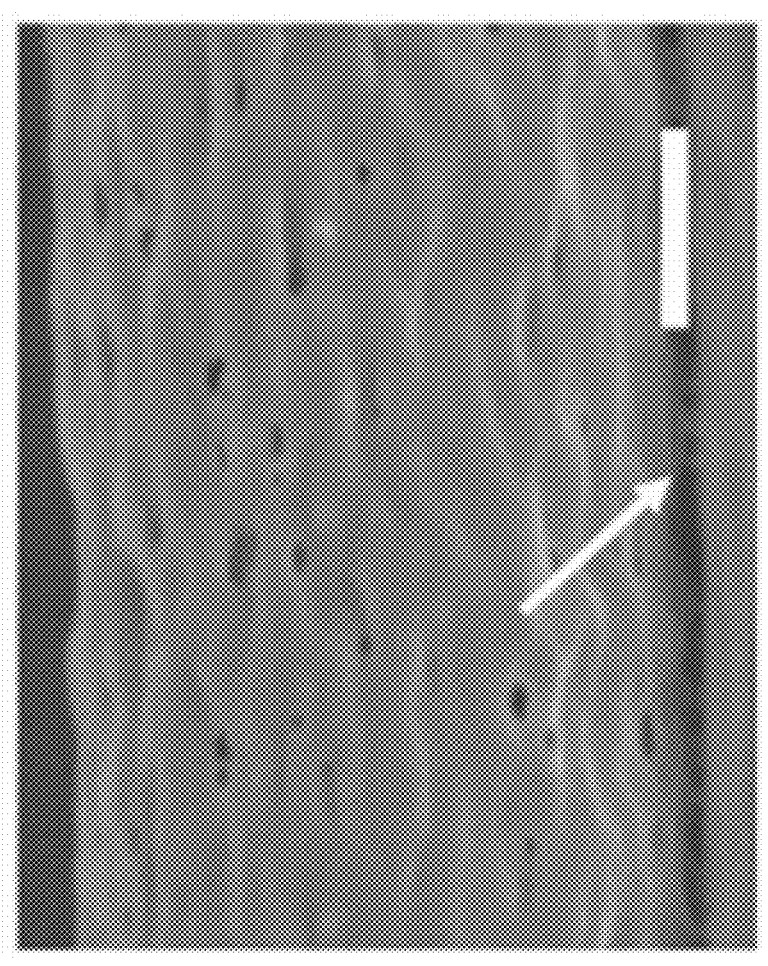

Example 11: Growth of Silk Fibroin Coatings on Topographically Complex Substrates. The ability of the method provided by embodiments of the present disclosure to coat non-planar, geometrically complex substrates was explored using electrospun poly-L-lactic acid fiber scaffolds as a substrate. These scaffolds have aligned fibers several microns in diameter and furthermore exhibit nanoscale topographies, such as divots and pits, on their surfaces to enhance nerve cell attachment. Scaffolds were coated in which the scaffold was immersed in a composition including 0.5 mg/mL Bombyx mori silk fibroin with 200 mM potassium phosphate in aqueous solution at 22° C. on an orbital shaker set at 60 RPM. To visualize the uniformity of coatings, scaffolds with and without coatings were labeled with FITC, a fluorophore that reacts with primary amines of proteins. As shown in FIG. 20, confocal fluorescence and brightfield images of uncoated scaffolds showed no FITC labeling, as expected due to the lack of primary amines on poly-L-lactic acid. Images of scaffolds coated for 12 or 24 hours showed homogeneous fluorescence on the scaffold fibers, indicating that the silk fibroin coatings were conformal and evenly applied to fibers in the scaffold. SEM was additionally utilized to image the fidelity of the coatings to fine nanoscale topographical features on the fiber surface, such as pits 50-200 nm long. These images showed that the pitted morphology is still retained after coating self-assembly (see FIGS. 21A-21B).

Figure 22:
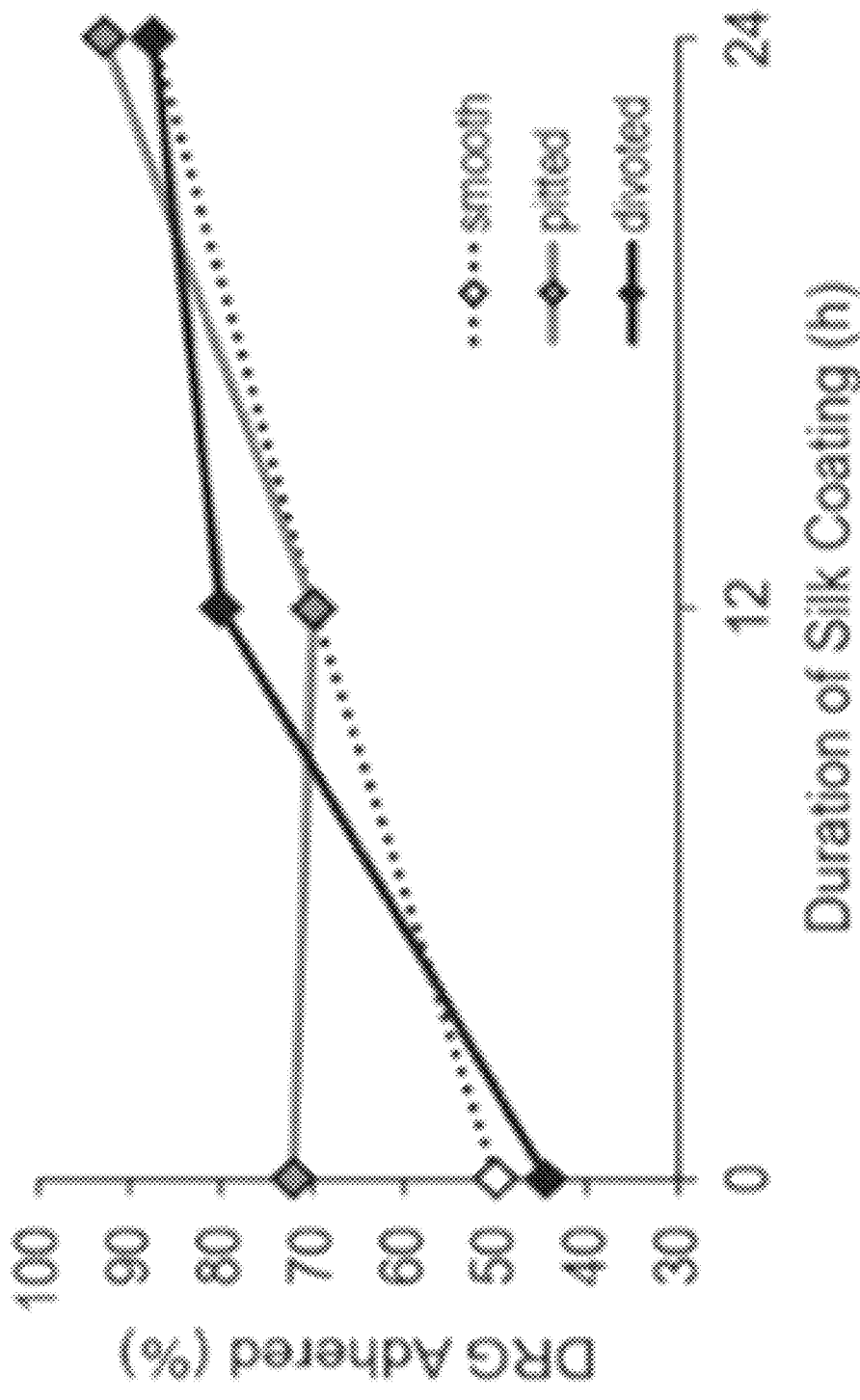
FIG. 22 is a graph portraying adhesion of rat Dorsal Root Ganglia (DRG) to electrospun poly-L-lactic acid scaffolds with and without coatings according to some embodiments of the present disclosure.
Figure 23A:
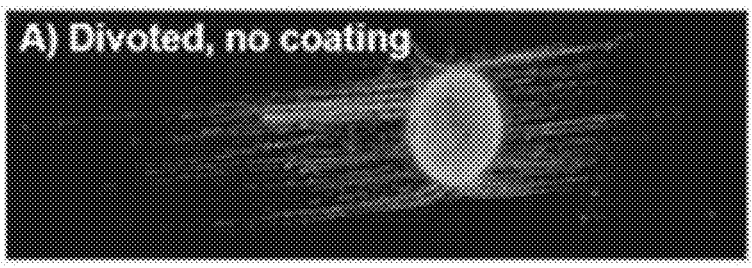
FIGS. 23A-23C are images of confocal microscopy analysis of DRG cultured on poly-L-lactic acid scaffolds without coating (FIG. 23A) and with coating (FIG. 23B-23C) according to some embodiments of the present disclosure.
Figure 23B:
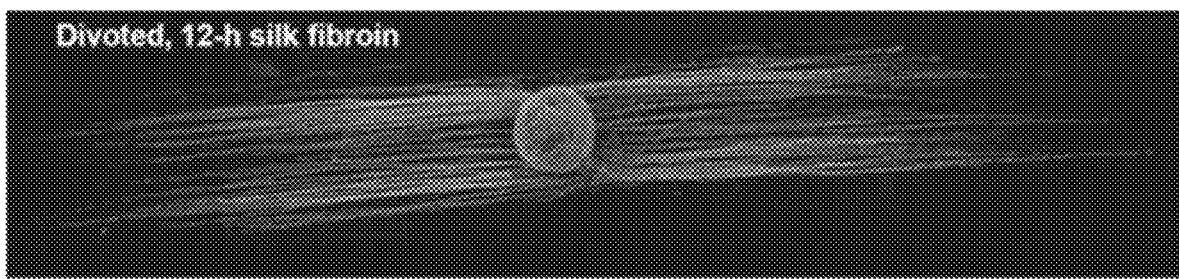
Figure 23C:
Figure 23D:
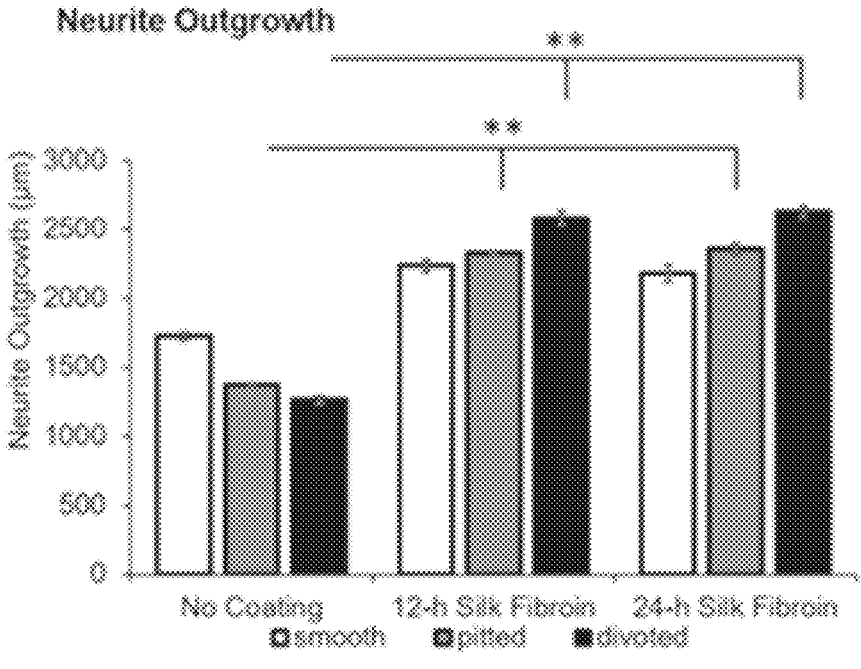
FIGS. 23D-23E are graphs quantifying neurite outgrowth (FIG. 23D) and DRG aspect ratio (FIG. 23E) on uncoated and coated scaffolds according to some embodiments of the present disclosure.
Figure 23E:
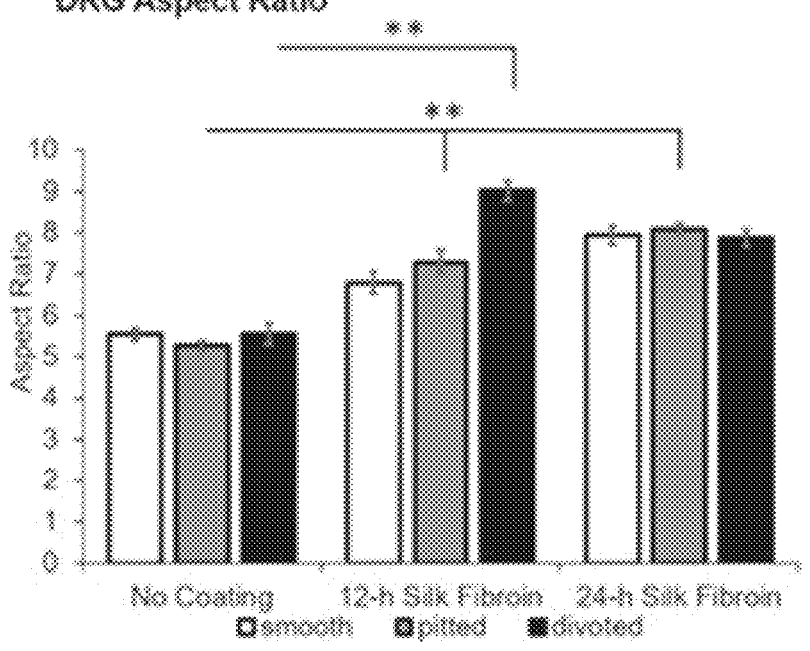
Figure 24A:
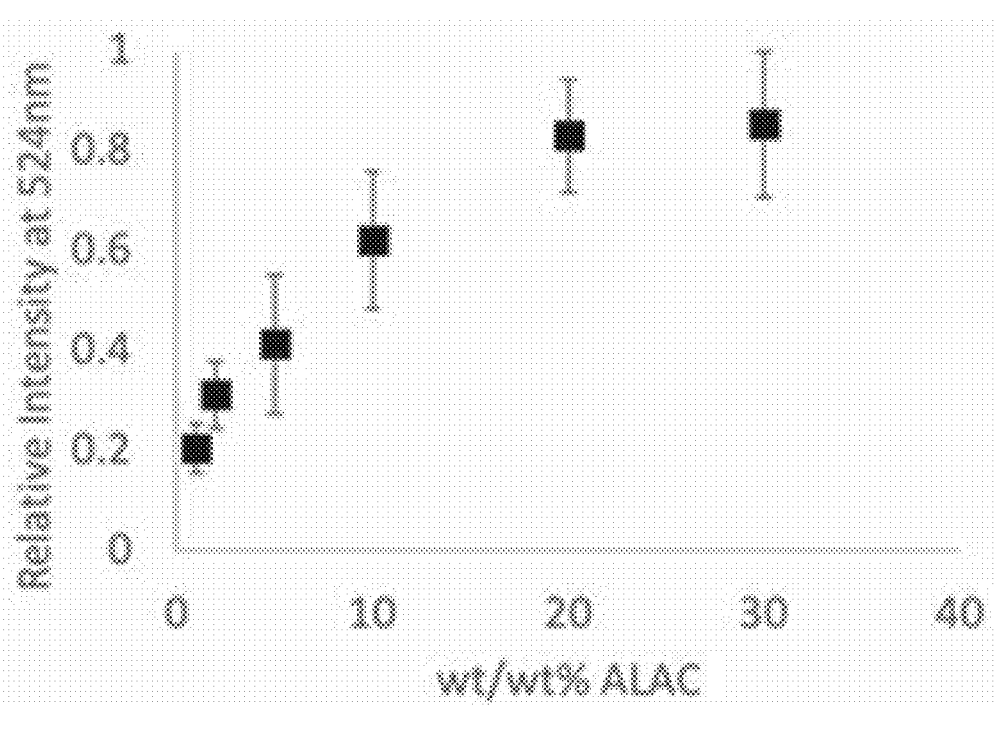
FIGS. 24A-24D are graphs showing fluorescence intensity to quantify integration by co-assembly of various non-silk fibroin proteins into the coatings according to some embodiments of the present disclosure.
Figure 24B:
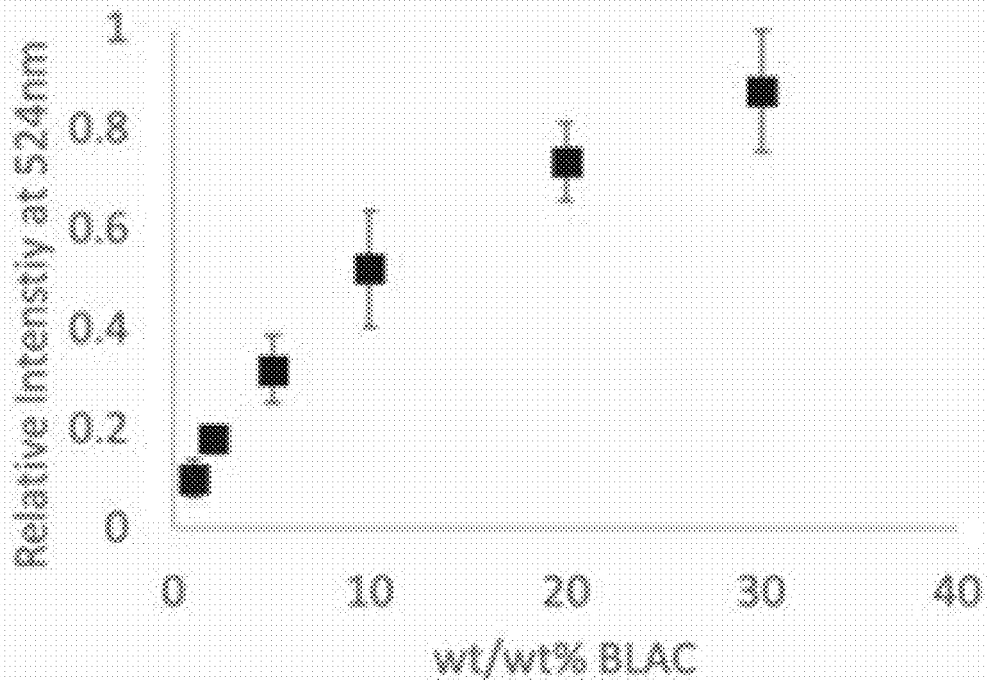
Figures 24C, 24D:
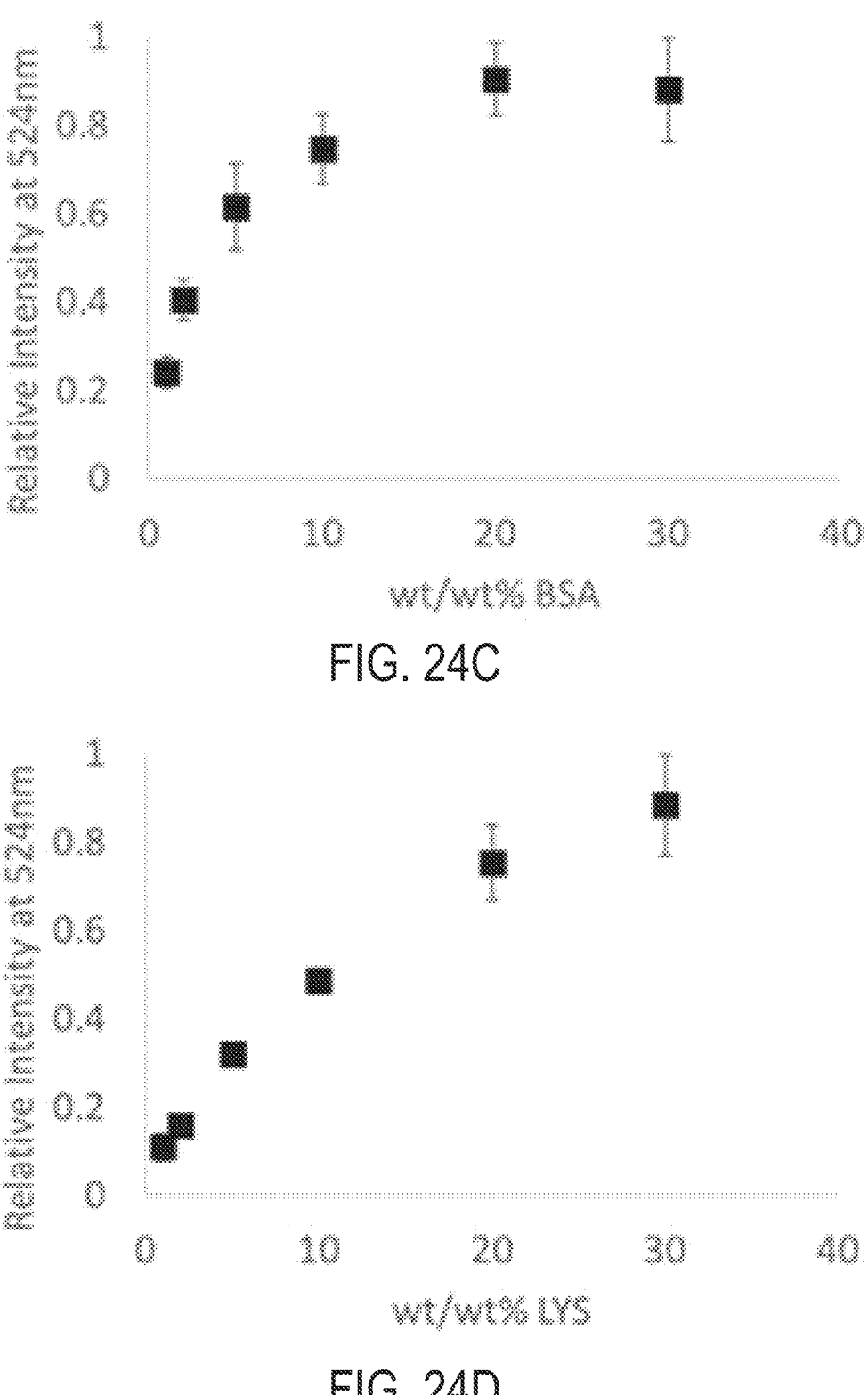

Example 12. Silk Fibroin Coatings Improve Nerve Cell Attachment and Neurite Extension on Scaffolds. The ability of silk fibroin coatings to improve nerve cell attachment and neurite outgrowth was explored using coated and uncoated electrospun poly-L-lactic acid scaffolds. These scaffolds have aligned nanofibers that encourage directional neurite extension and nanoscale surface topographies, such as pits and divots, to improve nerve cell adhesion. Scaffolds were coated in which scaffolds were immersed in a composition including 0.5 mg/mL Bombyx mori silk fibroin with 200 mM $KH_2PO_4$ in aqueous solution at 22° C. on an orbital shaker set at 60 rpm. Referring now to FIG. 22, coated scaffolds demonstrated a significant increase in adhesion of rat DRG for all surface topographies examined. Furthermore, neurite extension was significantly increased on coated scaffolds, especially for scaffolds with pitted or divoted surface nanotopographies (see FIGS. 23A-23E). These results indicate that self-assembled silk fibroin coatings can modify the surfaces of biomedical materials to improve biocompatibility and efficacy in nerve tissue regeneration.

Example 13: Integration of Non-Silk Fibroin Proteins in the Coating by Co-Assembly. Fluorimetry was used to quantify integration of various non-silk fibroin proteins into the silk coatings by co-assembly during coating growth. To generate these coatings, fluorescein-labeled bovine serum albumin (FITC-BSA), fluorescein-labeled α-lactalbumin (FITC-ALAC), fluorescein-labeled β-lactoglobulin (FITC-BLAC), or fluorescein-labeled lysozyme (FITC-LYS) was dissolved in an aqueous composition with 0.5 mg/mL Bombyx mori silk fibroin and 200 mM potassium phosphate, as provided by a mixture of $KH_2PO_4$ and $K_2HPO_4$ that kept the solution buffered at pH 5. Glass coverslips were immersed in the composition for 3 hours at 22° C. on an orbital shaker set at 60 RPM, rinsed with ultrapure water for 30 seconds, then dried. The fluorescence intensity arising from non-silk fibroin proteins loaded into the coating was measured by fluorimetry. Referring now to FIGS. 24A-24D, the concentration of FITC-BSA, FITC-ALAC, FITC-BLAC, and FITC-LYS in the composition was varied, and the results showed that increasing the ratio of non-silk fibroin protein to silk fibroin yields increased quantity loaded into the coating. For FITC-BSA and FITC-ALAC, which are hydrophobic and close to their isoelectric points in the composition, the amount that can be loaded into the silk fibroin coating plateaued at 20 wt/wt % protein to silk fibroin ratio.

Figure 25:
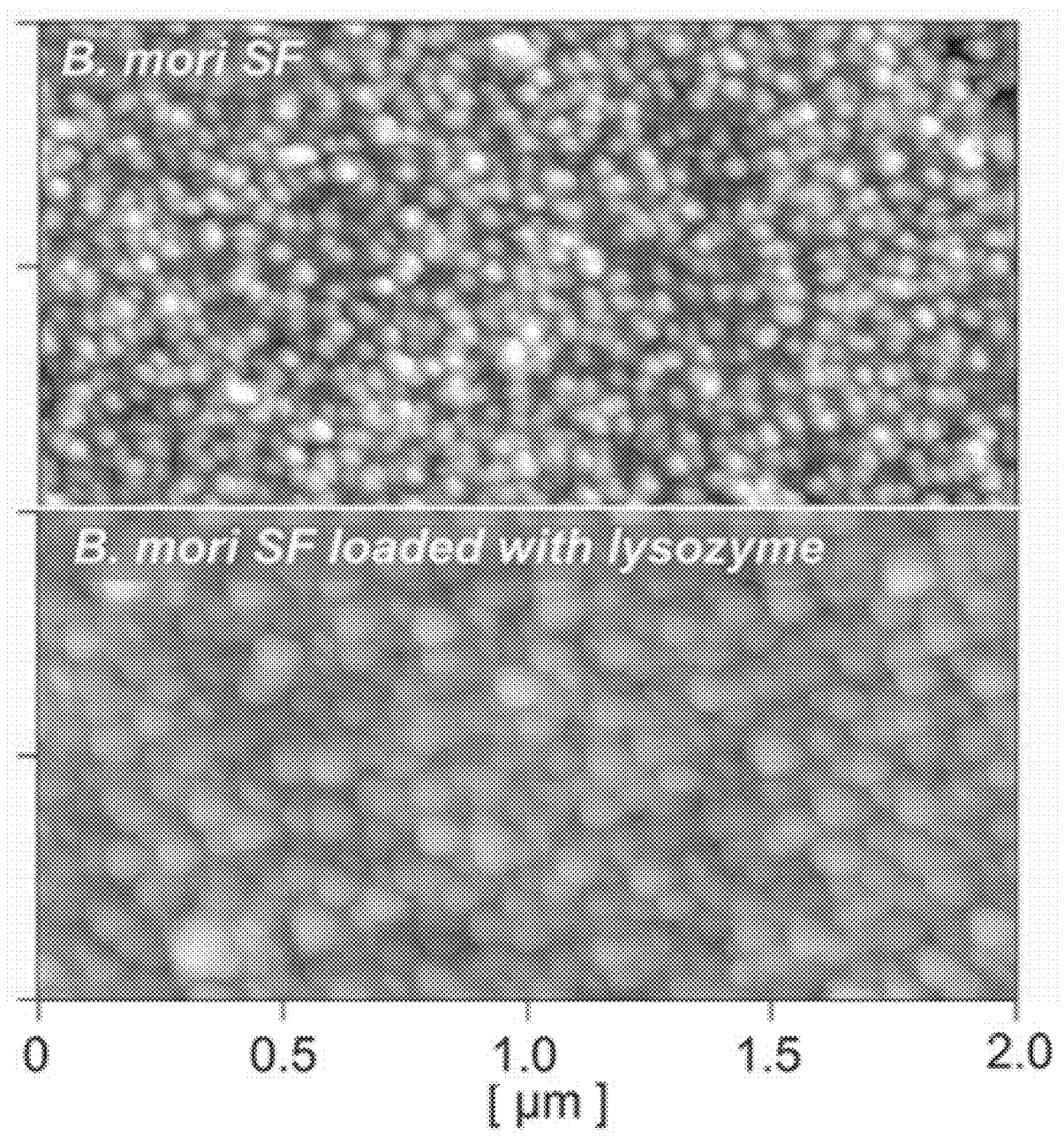
FIG. 25 portrays AFM images of coatings according to some embodiments of the present disclosure with and without FITC-lysozyme.

Referring now to FIG. 25, AFM imaging of silk fibroin coatings loaded with FITC-LYS showed that the size of globular structures observed in the coating is increased compared to coatings without FITC-LYS. This finding suggested that the fluorescent protein partitions to the interior of globular aggregates formed by silk fibroin during co-assembly. Without wishing to be bound by theory, loading of proteins into the coating by co-assembly may depend on hydrophobic interactions, size, and electrostatic forces between silk fibroin and the desired protein.

Figure 26:
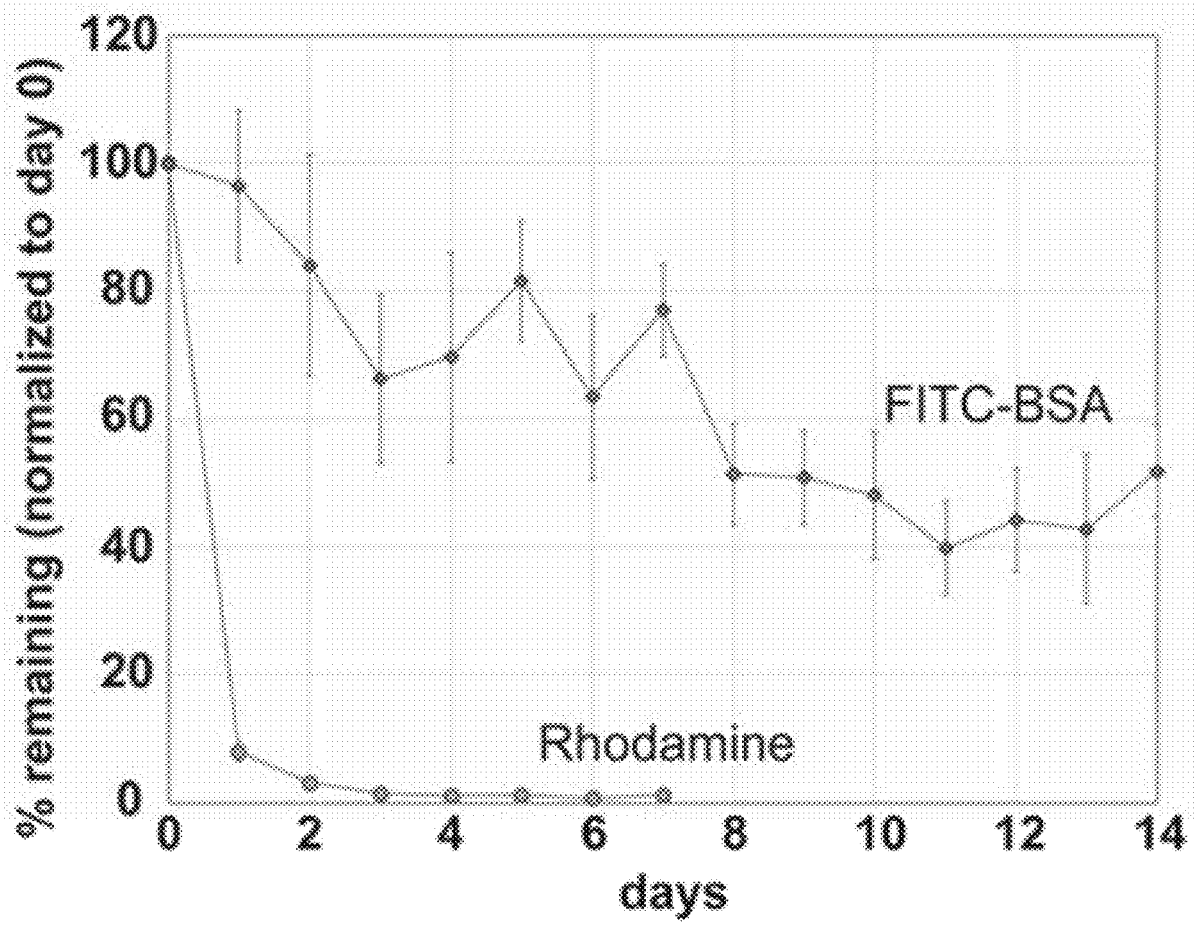
FIG. 26 is a graph showing sustained release of bovine serum albumin and rhodamine from coatings according to some embodiments of the present disclosure.

Example 13: Sustained Release of Proteins Integrated into Silk Fibroin Coatings by Co-Assembly. To examine the ability of molecules loaded into silk fibroin coatings by co-assembly to be retained and released over time, the release kinetics of Rhodamine B and FITC-BSA over 14 days was investigated. Coatings loaded with Rhodamine B or FITC-BSA were made where the molecule was dissolved in the composition with 0.5 mg/mL Bombyx mori silk fibroin and 200 mM potassium phosphate, as provided by a mixture of $KH_2PO_4$ and $K_2HPO_4$ that kept the solution buffered at pH 5. The concentration of Rhodamine B in the composition was 20 μM and the concentration of the FITC-BSA was 20/o by mass of the silk fibroin. Glass coverslips were coated by immersing in the composition for 3 hours at 22° C. while shaking at 60 RPM on an orbital shaker. The coated coverslips were then placed in a release media consisting of 150 mM NaCl at pH 7.2 with agitation on an orbital shaker at 60 RPM at 37° C. At each time point, coated coverslips were removed from the release media, dried using a stream of air, and the remaining fluorescence in the coating was measured using fluorimetry. Referring now to FIG. 26, results showed that Rhodamine B, a small molecule dye, was release rapidly within the first day, while FITC-BSA, a large protein was released gradually from the silk fibroin coating over more than 14 days. Thus, co-assembly with silk fibroin can generate coatings which enable sustained release of macromolecules from a substrate surface.

Figure 27A:
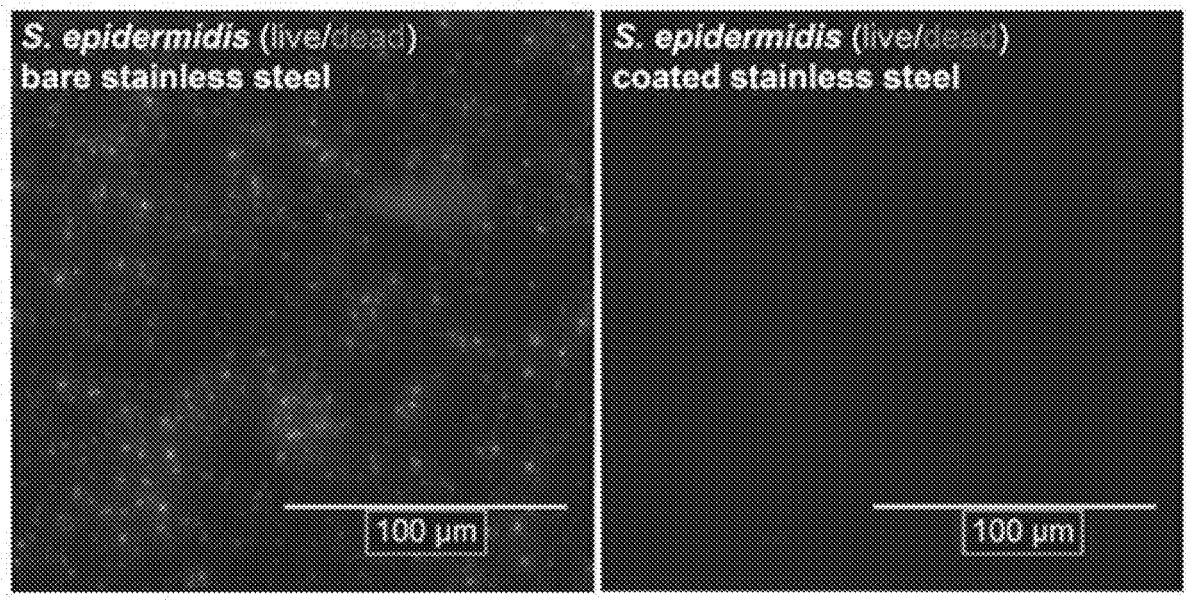
FIGS. 27A-27B portray results of experiments quantifying adhesion of bacteria on stainless steel with and without coatings according to some embodiments of the present disclosure.
Figure 27B:
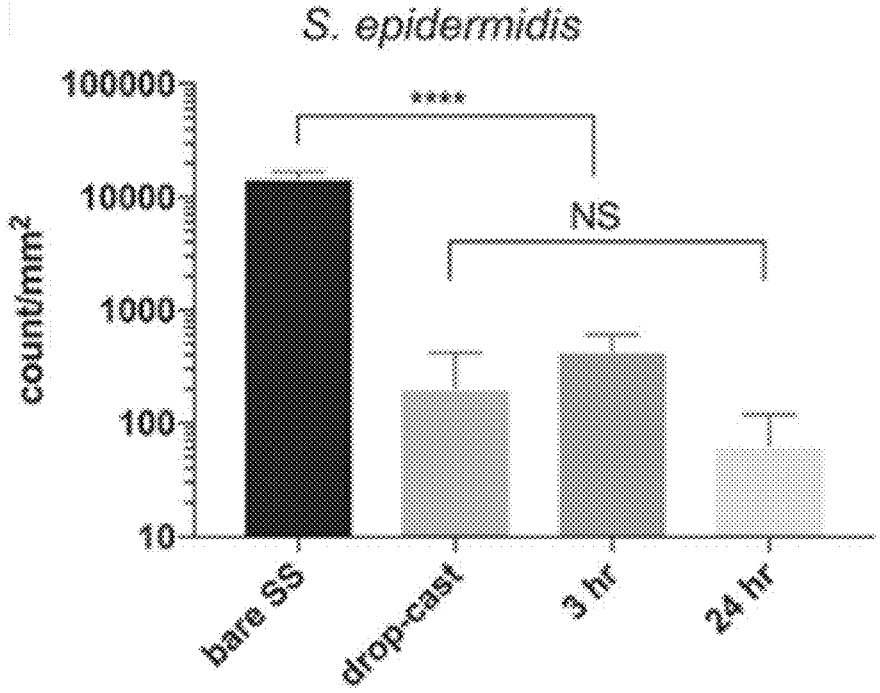

Example 14: Recombinant Silk Fibroin Coatings Decrease Bacterial Attachment. Referring now to FIGS. 27A-27B, stainless steel substrates were coated by recombinant silk fibroin where substrates were immersed in a composition including 0.5 mg/mL eADF4(C16) with 200 mM $KH_2PO_4$, 25 mM bicine, and 100 mM NaCl for 3 or 24 hours at 22° C. on an orbital shaker set at 60 RPM. Coated and uncoated substrates were then submerged in media including $10^8$ CFU/mL Staphylococcus epidermidis for 24 hours. Substrates were then gently rinsed and stained with a propidium iodide/SYTO9 LIVE/DEAD BacLight Bacterial Viability Kit and imaged using a fluorescent microscope (see FIG. 27A). Red and green fluorescence images, corresponding respectively to dead and live cells, were taken at 40× magnification from at least 10 random locations on each sample, and 3 samples were examined per condition. The number of live bacteria was counted manually using ImageJ software (see FIG. 27B). Statistical analysis was performed in GraphPad Prism software using one-way ANOVA (alpha=0.05) with Tukey's multiple comparisons post hoc test. Results showed that the self-assembled coatings, which were nanoscale in thickness, significantly reduced bacterial attachment to the surface by at least at least 97%, which is comparable to the reduction of bacterial attachment by thick drop-cast eADF4(C16) films. However, in contrast to drop-cast films, self-assembled coatings were highly adherent and did not show any evidence of delamination or defects that can potentially trap bacteria underneath the silk material.

Figure 28A:
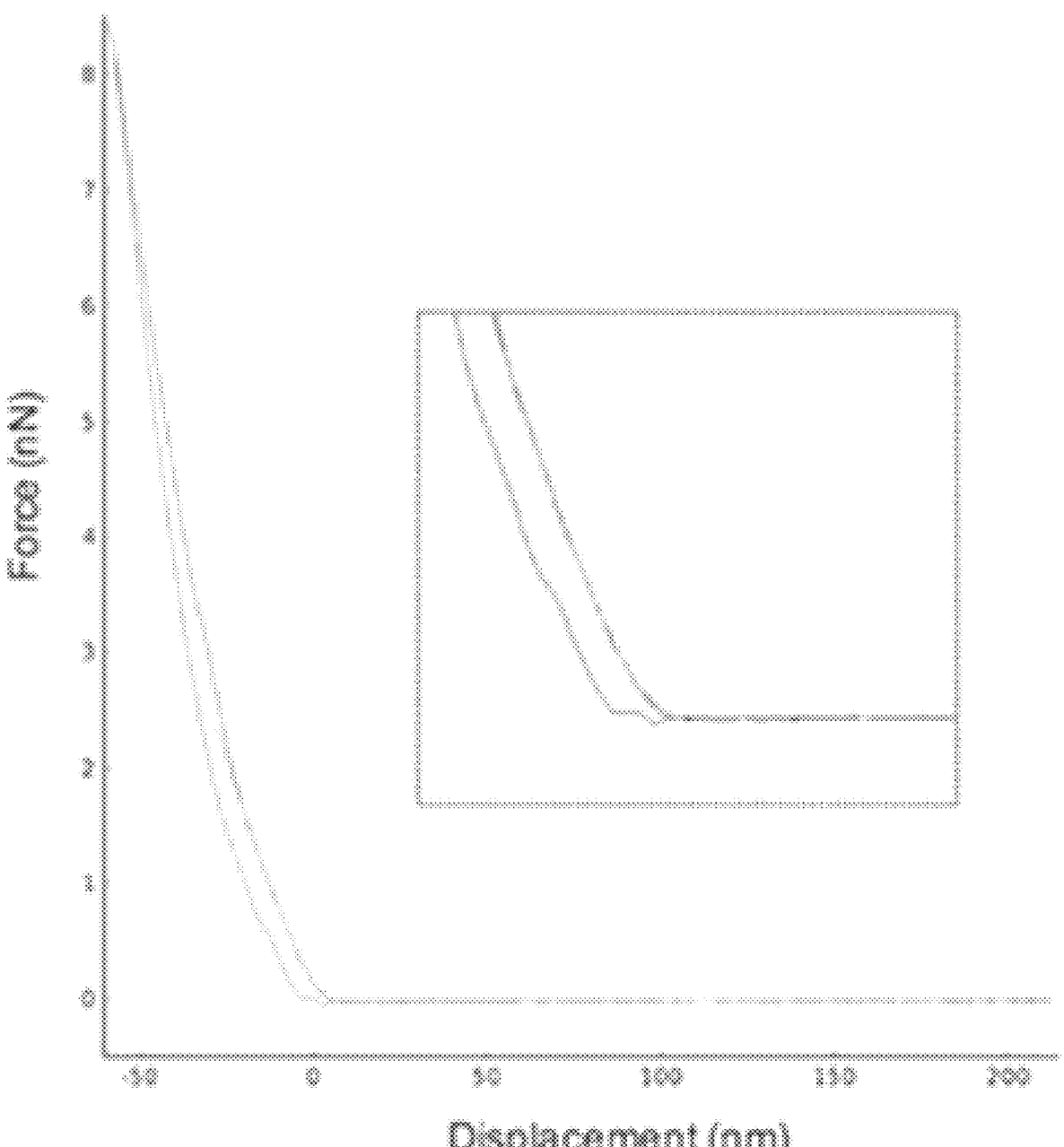
FIG. 28A is a graph including force-displacement curve obtained by nanoindentation $TiO_2$ substrates coated by recombinant silk fibroin in the wet state according to some embodiments of the present disclosure.
Figure 28B:
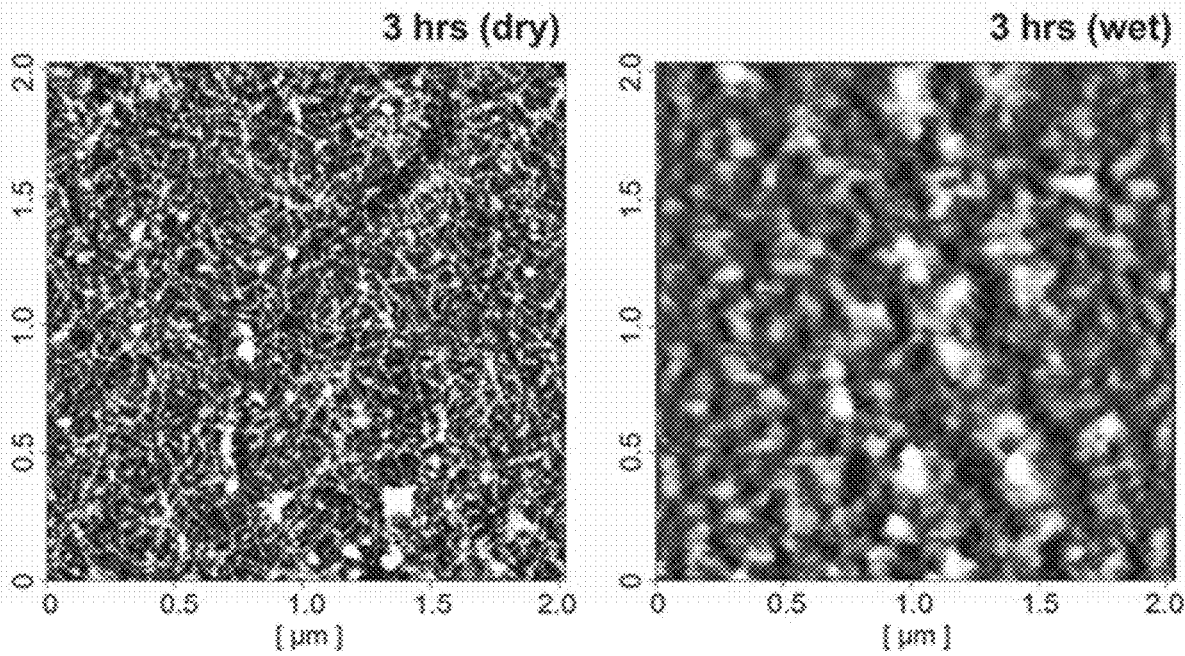
FIG. 28B portray AFM images of $TiO_2$ substrates coated by recombinant silk fibroin in the dry and wet state according to some embodiments of the present disclosure.

Example 15. Recombinant Silk Fibroin Coatings Create Hydrogel-Like Surface. Referring now to FIGS. 28A-28B, AFM nanoindentation in water was used to measure the stiffness of hydrated eADF4(C16) coatings made by self-assembly on $TiO_2$-coated Si wafer substrates. Coatings were made by immersing substrates in an aqueous solution including 0.5 mg/mL eADF4(C16) with 200 mM $KH_2PO_4$, 25 mM bicine, and 100 mM NaCl at 22° C. on an orbital shaker set at 60 RPM. A soft silicon cantilever with a spring constant of 0.2 N/m and a spherical probe tip 23 nm in diameter was used to indent the self-assembled coatings at of 1000 nm/s. Loading and unloading force-distance curves were fitted to a Hertz model with a Poisson's ratio of 0.5 (for incompressible rubber-like materials) to extract the Young's modulus of the coating. A Young's modulus of 2.9±1.4 MPa was found in water, which is comparable to the range of values expected for a hydrogel-like material. In comparison, native dragline silk threads are expected to have stiffness close to 10 GPa. Thus, these results suggest that the eADF4 (C16) coatings formed by self-assembly are able to modify the substrate with a layer of hydrogel-like material, thus significantly changing the mechanical properties of its surface. These findings are consistent with hydrated AFM images suggesting that self-assembled eADF4(C16) coatings exist in aqueous environments as a hydrated layer bound to the substrate surface.

Methods and systems of the present disclosure are advantageous to leverage the bioinspired self-assembly phenomenon of silk fibroin and silk fibroin-like macromolecules to generate nano-thin coatings with adhesive and cohesive stability. These coatings result from one-pot concurrent adsorption and supramolecular assembly controlled by kosmotropic components. The coating methods according to present disclosure differ from top-down coating methods, such as dip coating, spray coating, spin coating, or casting, in that the coating is molecularly grown from the substrate surface and does not utilize drying or removal of solvent to fix the macromolecules to the surface. The coating method also differs from covalent approaches, such as chemical grafting, in that no covalent chemistries are utilized to create the coating or fix the coating to the surface. The coating method also differs from layer-by-layer methods, in that only one composition is required and the substrate does not need to be transferred to more than one solution for continuous coating growth.

The coating methods are able to produce coatings that can completely cover the substrate surface with substantially no defects. The coatings generated are smooth on the nanometer scale and are free of inhomogeneities, such as the presence of adhered particulates or other features significantly larger than the typical feature size of the coating. Since the formation of these coatings by controlled self-assembly occurs in mild, aqueous conditions without the use of chemical crosslinkers, the coating method can be a potential strategy towards biomedical surface functionalizing. The coating methods according to the present disclosure can generate coatings on a variety of organic and inorganic substrates that are hydrophilic or hydrophobic, such as nylon, polypropylene, polycarbonate, polylactic acid, polyethylene, polyethylene terephthalate, or polytetrafluoroethylene, glass, stainless steel, $TiO_2$, and $SiO_2$.

Because the methods of coating according to the present disclosure grows the coating from the surface in a bottom-up approach, it is suitable for substrates that have high curvature or complex geometry, such as tissue engineering scaffolds consisting of an array of fibers with nano or micronscale diameters or porous materials. The coatings generated are several to tens of nanometers in thickness and have conformal fidelity to the surface, topographically complex surfaces can also be readily accommodated without significantly disrupting the geometrical features of the original surface. In contrast, materials with complex geometry or surface topography typically present significant challenges to top-down coating methods, primarily due to large inhomogeneities in solvent removal and drying across the surface.

Although the invention has been described and illustrated with respect to exemplary embodiments thereof, it should be understood by those skilled in the art that the foregoing and various other changes, omissions and additions may be made therein and thereto, without parting from the spirit and scope of the present invention.

What is claimed is:

1. A method of providing a coating to a surface, comprising:
   preparing a composition including a solvent and a silk component, wherein the silk component is chosen from the group consisting of a silk fibroin, a silk fibroin-like macromolecule, recombinant silk fibroin, and combinations thereof;
   adding a kosmotropic component to the composition; and
   contacting the composition with a portion of the surface, such that the composition does not dry on the surface, thereby forming the coating on the surface, the growth of the coating being continuous and indefinite without saturation in amount for a time period selected from the greater of:
   a time period of more than about one hour and less than about 24 hours, and
   a time period equal to the time required for the concentration of the silk component to drop below 0.05 mg/ml.

2. The method according to claim 1, further comprising:
   adjusting the pH of the composition to a value closer to the isoelectric point of the silk component.

3. The method according to claim 1, wherein the pH of the composition is between about 4 and 6.

4. The method according to claim 1, wherein the pH of the composition is below about 5.5.

5. The method according to claim 4, further comprising:
   adding one or more acids to the composition to reduce the pH of the composition to a value below about 5.5.

6. The method according to claim 1, further comprising:
   adding one or more additives to the composition, the one or more additives including a small molecule, peptide, protein, polymer, nanoparticle, pharmaceutical compound, nutraceutical compound, or combinations thereof.

7. The method according to claim 6, wherein the one or more additives are provided in the composition at a concentration of less than about 30% by weight of the silk component.

8. The method according to claim 6, wherein the kosmotropic component is added to the composition after adding the one or more additives.

9. The method according to claim 1, wherein the kosmotropic component includes phosphate, hydrogen phosphate, dihydrogen phosphate, $KH_2PO_4$, $K_2HPO_4$, or combinations thereof.

10. The method according to claim 1, wherein the concentration of silk component in the composition is about 0.1 mg/mL to about 2 mg/mL.

11. The method according to claim 10, wherein the concentration of silk component is about 0.5 mg/ml.

12. The method according to claim 1, wherein the concentration of kosmotropic component in the composition is between about 150 mM and about 300 mM.

13. The method according to claim 12, wherein the concentration of kosmotropic component is about 200 mM.

14. The method according to claim 1, wherein the temperature of the composition is between about 20° C. to about 25° C.

15. The method according to claim 1, wherein the coating has a thickness in the dry state of greater than about 10 nm.

16. The method according to claim 1, wherein the solvent is water.

17. The method according to claim 1, wherein the recombinant silk fibroin is a recombinant spidroin.

18. A method of generating a surface coating on a surface, comprising:

preparing a composition including a solvent and a silk component, wherein the silk component includes a silk fibroin, a silk fibroin-like macromolecule, a recombinant silk fibroin, or combinations thereof;

adding a kosmotropic component to the composition;

contacting the composition with a portion of the surface to initiate coating of the portion;

maintaining the portion in contact with the composition, thereby forming the coating on the surface, the growth of the coating being continuous and indefinite without saturation; and removing the composition from the portion to halt coating of the portion.

19. The method according to claim 18, wherein contacting the composition with the surface to initiate coating of the portion includes:

agitating the composition.

20. The method according to claim 19, wherein removing the composition from the surface to halt coating of the portion includes:

rinsing the portion with a solution.

21. The method according to claim 18, wherein the kosmotropic component includes $KH_2PO_4$, $K_2HPO_4$, or combinations thereof.

22. The method according to claim 21, further comprising:

adding one or more acids to the composition to reduce the pH of the composition to a value below about 5.5.

23. The method according to claim 18, wherein the concentration of silk component is about 0.5 mg/ml.

24. The method according to claim 18, wherein the concentration of kosmotropic component is about 200 mM.

25. A method of providing a coating to a surface, comprising:

preparing a composition including a solvent comprising an aqueous solution and a silk component, wherein the silk component includes a silk fibroin, a silk fibroin-like macromolecule, a recombinant silk fibroin, or combinations thereof;

adding a kosmotropic component to the composition, wherein adding the kosmotropic component to the composition results in entities selected from the group consisting of nanofibers, micelles, aggregates, and combinations thereof, wherein the entities have at least one characteristic dimension smaller than 100 nm, and wherein the entities do not precipitate from the aqueous solution;

contacting the composition with a portion of the surface; and maintaining the portion of the surface contact in with the composition, in a manner such that the composition does not dry on the surface, thereby providing the coating to the surface.

* * * * *